(12) United States Patent
Ayyub et al.

(10) Patent No.: US 10,591,495 B2
(45) Date of Patent: Mar. 17, 2020

(54) DEVICE AND METHODS OF USING DEVICE FOR DETECTION OF HYPERAMMONEMIA

(71) Applicants: University of Maryland, College Park, College Park, MD (US); CHILDREN'S NATIONAL MEDICAL CENTER, Washington, DC (US)

(72) Inventors: Omar Bilal Ayyub, Potomac, MD (US); Adam Michael Behrens, Olney, MD (US); Peter Kofinas, North Bethesda, MD (US); Marshall Lynn Summar, II, Washington, DC (US); Juan Manuel Cabrera-Luque, Rockville, MD (US); Gary Cunningham, Washington, DC (US)

(73) Assignees: University of Maryland, College Park, College Park, MD (US); Children's National Medical Center, Washington, DC (US)

( * ) Notice: Subject to any disclaimer, the term of this patent is extended or adjusted under 35 U.S.C. 154(b) by 293 days.

(21) Appl. No.: 15/570,269

(22) PCT Filed: Apr. 27, 2016

(86) PCT No.: PCT/US2016/029623
§ 371 (c)(1),
(2) Date: Oct. 27, 2017

(87) PCT Pub. No.: WO2016/176366
PCT Pub. Date: Nov. 3, 2016

(65) Prior Publication Data
US 2018/0143210 A1 May 24, 2018

Related U.S. Application Data

(60) Provisional application No. 62/153,409, filed on Apr. 27, 2015.

(51) Int. Cl.
*G01N 33/84* (2006.01)
*G01N 33/68* (2006.01)
(Continued)

(52) U.S. Cl.
CPC ........... *G01N 33/84* (2013.01); *A61K 31/216* (2013.01); *A61P 3/00* (2018.01); *B01L 3/502715* (2013.01);
(Continued)

(58) Field of Classification Search
CPC ........... G01N 21/78; G01N 2021/7759; G01N 2021/775; G01N 2800/00;
(Continued)

(56) References Cited

U.S. PATENT DOCUMENTS 4,963,814 A  10/1990  Parks et al.
4,970,172 A  11/1990  Kundu
(Continued)

FOREIGN PATENT DOCUMENTS

| IN | 1871/DEL/2008 | 4/2010 |
| WO | 2015031911 A1 | 3/2015 |
| WO | WO-2015031911 A1 * | 3/2015 |

OTHER PUBLICATIONS

Ayyub Omar B et al: "Simple and inexpensive quantification of ammonia in whole blood", Molecular Genetics and Metabolism, vol. 115, No. 2, 2015, pp. 95-100, XP029130368, ISSN: 1096-7192, 001: 10.1016/J.YMGME.2015.04.004.
(Continued)

*Primary Examiner* — Dennis White
(74) *Attorney, Agent, or Firm* — Ballard Spahr LLP

(57) ABSTRACT

The present disclosure relates to a biosensor capable of measuring the total concentration of one or a plurality of ammonia or ammonium ions with the use of indophenol reagents in the presence of an ionomer. In some embodi-
(Continued)

ments, the biosensor comprises a perflurinated membrane that comprises an ionomer in contact with an alkali buffer in a vessel configured to receive a sample, such as whole blood. The disclosure also relates to a method of detecting or quantifying the ammonia or ammonium ion concentration in whole blood in a point of care bio sensor without reliance on gas chromatography or any measurement that takes more than about twenty minutes.

31 Claims, 21 Drawing Sheets

Specification includes a Sequence Listing.

(51) Int. Cl.
*A61P 3/00* (2006.01)
*A61K 31/216* (2006.01)
*B01L 3/00* (2006.01)
*G01N 21/78* (2006.01)
*G01N 21/77* (2006.01)

(52) U.S. Cl.
CPC .......... *G01N 21/78* (2013.01); *G01N 33/6806* (2013.01); *B01L 2200/16* (2013.01); *B01L 2300/0636* (2013.01); *G01N 2021/775* (2013.01); *G01N 2021/7759* (2013.01); *G01N 2800/04* (2013.01)

(58) Field of Classification Search
CPC ....... B01L 3/502715; B01L 2300/0636; B01L 2200/16; A61K 31/216; A61P 3/00
See application file for complete search history.

(56) References Cited

U.S. PATENT DOCUMENTS

| | | | |
|---|---|---|---|
| 4,999,582 A | 3/1991 | Parks et al. | |
| 4,999,632 A | 3/1991 | Parks | |
| 5,128,015 A | 7/1992 | Szuminsky et al. | |
| 5,243,516 A | 9/1993 | White | |
| 5,352,351 A | 10/1994 | White et al. | |
| 5,366,609 A | 11/1994 | White et al. | |
| 5,405,511 A | 4/1995 | White et al. | |
| 5,438,271 A | 8/1995 | White et al. | |
| 5,624,537 A | 4/1997 | Turner et al. | |
| 5,670,031 A | 9/1997 | Hintsche et al. | |
| 5,698,083 A | 12/1997 | Glass | |
| 5,762,770 A | 6/1998 | Pritchard et al. | |
| 5,981,203 A | 11/1999 | Meyerhoff et al. | |
| 6,645,359 B1 | 11/2003 | Bhullar et al. | |
| 6,662,439 B1 | 12/2003 | Bhullar | |
| 6,720,164 B1 | 4/2004 | Shinozuka et al. | |
| 7,150,975 B2 | 12/2006 | Tamada et al. | |
| 2004/0186359 A1 | 9/2004 | Beaudoin et al. | |
| 2005/0245844 A1 | 11/2005 | Mace et al. | |
| 2008/0242738 A1 | 10/2008 | Marks et al. | |
| 2008/0289962 A1 | 11/2008 | Prohaska et al. | |

OTHER PUBLICATIONS

Martina Baumgartner et al: "Evaluation of flow injection analysis for determination of urea in sheep's and cow's milk", Acta Veterinaria Hungarica .• vol. 50. No. 3. Jul. 1, 2002 (Jul. 1, 2002). pp. 263-271. XP055354034. HU ISSN: 0236-6290. 001: 10.1556/AVet.50.2002.3.2.

EP Extended Search report dated Mar. 3, 2017 from EP Application No. EP14841207.5.

Eggenstein et al., "A desposable biosensor for urea determination in blood based on an ammonium-sensitive transducer", Biosensors & Bioelectronics 1999 14:33-41.

Eijgelshoven et al., "The time consuming nature of phenylketonuria: a cross-sectional study investigating time burden and costs of phenylketonuria in the Netherlands", Mol Genet Metab 2013 109(3):237-242.

Poordad, "Review article: the burden of hepatic encephalopathy", Aliment Pharmacol Ther 2007 52(Suppl):3-9 Abstract only submitted.

Sezonov et al., "*Escherichia coli* physiology in Luria-Bertani broth", J Bacteriol 189(23):8746-8749, 2007.

Summar et al., "The incidence of urea cycle disorders", Mol Genet Metab 2013 110(1-2):179-180.

Weatherburn, "Phenol-hypochlorite reaction for determination of ammonia", Anal Chem 39(8);971-974, 1967.

* cited by examiner

SEQUENCE LISTING

<160> NUMBER OF SEQ ID NOS: 24

<210> SEQ ID NO 1
<211> LENGTH: 1068
<212> TYPE: DNA
<213> ORGANISM: Artificial Sequence
<220> FEATURE:
<223> OTHER INFORMATION: phenylalanine dehydrogenase

<400> SEQUENCE: 1

```
atggaaatct tcgaggaaat caaacggcgg ggacacgagc aaattctgtt caattatgat      60
cgggcttccg gtttgaaagc aattatcgcc attcacaata ctacgttggg gccggcgttg     120
ggcgggtgcc gaatgttacc gtatcaaacg gaagaggcgg ccctcgagga tgcgctgcgg     180
ttgtcggaag ggatgaccta taaagcggcc gccgccgggc tcgatttcgg cggggggcaaa    240 acggtgatta tcggggatcc gatgaaagac aagtccgagg ccctgtttcg tgcgctcggg     300
cgttttatcg agaccttgaa aggccgttac cttacgggag aagacgtagg aaccaacgaa     360
gaagattttg tctgggctcg tcgggaaacc cgttatgttg tcggattgcc gccggcttat     420
ggcgggtccg gcgatacggg tgacaatacc gcgcgcggcg tcattcaagc gatgcgcgcc     480
gcgttgatgc accggtacgg ttcgccggat ctccagggcc ggcggattgc cgtccaaggg     540
ctgggcaaag taggctatca tgtggcgcga cgggccatcg aggccggcgc tcgagtgatt     600
gcggccgata tcaatccgca tgtagtcggc cgagtggcgt ccgcttgggg gattgaagcc     660
accgatccgt gggctgtggt ggaaaccccc tgcgatattt tcgcccctg tgcgttgggt      720 aacgtcatta cggaacggac cgtgtccgcc ctccaatgtc aggtggtggc cggttcggcc     780
aacaatcagc tggcggatga tcgactggcc gatgatttag ctgcccgcgg cattctctat     840
gcgccggatt ttattgcgaa tgccggcgga ttgattcagg tggcggatga aattcgggga     900
tatcatgaag aacgggtccg tcatcaaata gacgggattt atgacgtcct gctcgagatt     960
tttcggaagg cggacgcctc cggccgatca accgtggcgg ttgcggtaga cgaggcgcgt    1020
```
cgccgtttgg acaccattca ggccatccac cgcctgtacg gatcatag          1068

<210> SEQ ID NO 2
<211> LENGTH: 3939
<212> TYPE: DNA
<213> ORGANISM: Artificial Sequence
<220> FEATURE:
<223> OTHER INFORMATION: phenylalanine ammonia-lyase

<400> SEQUENCE: 2

```
ctgcaggtca acggatcata ttctacacat atataatgca ctccaattga cataatacat    60
aacgtgacat atgatacatt tattaatatt aattgtcaca tttacacttc acatattaaa   120
atactctcgt atgaatgcaa tttgaaacat attttaaatt aattgattga tatatattga   180
acaaaaccta acaaaaatgc accctcttgg ttcacaaaga aactttcttc tatttctcac   240
ttatttctgc tagtgtcttt cctattcaaa gccatcattt ccatcaacct tcacaatacc   300
atgtttaaaa agtcattaaa aatcaatttt taaatagaa aaaacaaga agatggaaat     360
cacttggttg gtactatata tttagttgtt aagtttgact cataccgtgt attgaccaat   420
ataaataaaa tcttatttca ataaaattca aaagttcaat aaatatatat tcgttcataa   480
cttataataa aattgattat acatagtcct ccccccattca cttttactga tcaattattt  540
ctaaaatata ttattacttt tacttgttat ttttaataaa ttaagaaaat ataatactcc   600
cttcgttttt aaaaaaatac ctagtttgac ttgaaacgga gtttaataaa agaaagaaga   660
cttgttaatc ttgtgattct aaattaaagt tatgtcaaat gtaccaaaat gtcctttaat   720
cttgtggtct taaacatgtc acatgaaaaa ttaaagtgtt tccaaaaaaa gaaaggggtc   780
aatgtcattc ttttttaaac agactaaaaa agaaataaac tcattctttt tgaaacggag   840
agagtaatttt tttccacgtt ttactcatta atattaaata ttattctcta gatcatccta   900
taagatctaa tagtggacat caattaatac ctatgtcact tattattatt ttaataattg    960
tatcaagtca aataataaca agtaaaaatg gagtacctac tattaatctt caacaaccac  1020
aatttactag tttttttccta gcaacccccct ctcacatatt tcaccattta ctggttttt   1080
cctagcaacc ccctctcaca tattttgttt accaaccatc atttgttcct ctatatatac  1140
tcaccacatg atagatacat atatatacca caaccaaaac aaaaggttt taagttcac    1200
aacatttttt atatacatac aaataaactc taaccatttt ctcttcacta aaatttcttc  1260
attacaaatc taacaattta cttgatccaa tggcaccatc aattgcacaa atggacata    1320
ttaatggaga agtagctatg gatttgtgca agaaatcaat caatgatcca ttgaattggg  1380
aaatggctgc tgattcttta agaggcagcc atttggatga agtgaaaaag atggtggatg  1440
aatttagaaa gccaattgtg aaacttgggg gtgaactttt gtcagttgca caagttgcat  1500
ccattgcaaa tgttgatgac aaaagtaatg gggttaaagt ggaactttct gaaagtgcaa  1560
gggctggtgt gaaagctagt agtgattggg ttatggatag tatgagtaaa ggtacagata  1620
gttatggtgt tactgctgga tttggagcaa catctcatag aagaacaaaa aatggtggtg  1680
ctcttcaaaa agaacttatt aggtaaacaa actatttttt ttcgttatat atactaacaa  1740
tgtaaagaat ttaatatttt tttgttatat atactaacaa tgtaaaaaat ttaatatttt  1800
tttgttatat atactaacaa tgtaaagaat ttaatatttt tttgttatac atagcttatc  1860
gactacttaa gtgctccatt gataaagatt ttttttgtt tttacgcgaa ggggattcgg   1920
atgaattcag ttaaaatgtg atcttaatga attatgatat tttttgtag gttcttgaat   1980
gctggagttt ttggtaatgg aatagaatca tttcacacat tgccacattc agcaacaagg  2040
```

```
gcagctatgc ttgttaggat caacactctg cttcaaggct actctggcat tagatttgag    2100
atcttggaag caatcactaa gttgatcaat agcaacatca ccccgtgttt gcctctccgt    2160
ggcacgatca ctgcctcggg tgatctcgtc cctttgtcct atattgctgg tttgctcact    2220
ggcagaccta attccaaggc tgttggaccc aatggtgaga acttaatgc tgaggaagct     2280 ttctgcgtgg ctggtattag tggtggattt ttcgagttgc agcctaagga aggacttgca    2340
cttgtgaatg gcacagcagt tggttctgct atggcatcaa tagtcctgtt tgagtccaat    2400
atctttgctg ttatgtctga agttttatca gcgattttta ctgaagtgat gaacggaaag    2460
cccgaattca ctgactattt gacacacaag ttgaagcatc accctggtca gattgaggct    2520
gctgctatta tggaacacat tttggatgga agctcttatg tgaaggtagc tcagaagctc    2580
catgaaatgg atcctcttca aaaccaaag caagatcgtt atgctctccg aacatctcca    2640
caatggcttg gacctcagat tgaagtcatt cgtgctgcaa ctaagatgat cgagagggag    2700
attaactcag tgaacgacaa tccattgatc gatgtttcaa gaaacaaggc cttacatggt    2760
ggcaacttcc aaggaacccc tattggtgtc tccatggata atacaagatt ggcccttgca    2820
tcaattggta aattgatgtt tgcccaattc tcagagcttg tcaacgacta ttacaacaac    2880
gggttgccat ctaatctgac agcaggaagg aatccaagct tggactatgg tttcaagggc    2940
gctgaaatcg cgatggcttc ttactgctcg gaacttcaat tcttggcaaa tccagtgact    3000
aaccatgtct aaagtgctga gcaacacaac caagatgtga attccttggg cttaatttca    3060
gccaggaaaa cagctaaggc tgttgatatc ttgaagataa tgtcatcaac ctatctcgtg    3120
gctctttgcc aagctattga cttacgacat ttggaggaaa acttgaagag tgttgtcaag    3180
aacacagtta gccaagtagc taagagaact ttgacaatgg gtgctaatgg tgaacttcat    3240
ccagcaagat tcagcgaaaa agaattgctt cgagtcgtgg atagagaata cttgtttgcc    3300
tatgctgatg atccctgcag ctccaactac cctttgatgc agaagctgag acaagtcctt    3360
gttgatcaag caatgaagaa tggtgaaagt gagaagaatg tcaacagctc aatcttccaa    3420
aagattggag ctttcgagga cgaattaatc gctgtgttgc ctaaagaagt tgagagtgta    3480
agagctgttt ttgaaagtgg caacccttta attcgtaaca ggatcacaga atgcagatca    3540
tatccattgt acaggttggt gagagaagaa cttggaacag aattgttgac gggtgaaaaa    3600
gttcgatcac ctggtgagga gattgataaa gtgtttacag caatatgtaa tggacagatt    3660
attgatccat tgttggagtg tctgaagagc tggaatggtg ctcctcttcc aatctgctaa    3720
atgtgttatt cttttcaagtt ctttttttgt accttttagt gaattactag aattataatg    3780
atgttatgaa cttatattaa aaaaaatat ttttgactat aaaatttagt tttgttattg     3840
aaattaaagg ctcaatctgt gttctttcct tctgttatct gaatattata agaattcaag    3900
taatctttta gctttgtgaa catgatgaca tgctttctt                           3939
```

<210> SEQ ID NO 3
<211> LENGTH: 1521
<212> TYPE: DNA
<213> ORGANISM: Artificial Sequence
<220> FEATURE:
<223> OTHER INFORMATION: histidine ammonia-lyase

<400> SEQUENCE: 3

```
atgatcacgc ttaccccgg ccacctgacc ctcccgcaac tgcgccagat cgcgcgcgag     60
cccgtgcagc tgacgctgga tccggccagc ttcgcgaaga tcgacgcggg cgcgaaggcc    120
```

```
gtgtccgaca tcgccgcgaa gggcgagccg gcgtacggca tcaacacggg cttcggtcgt    180
ctggccagca cgcatatccc gcacgatcag ctcgaattgc tgcagaagaa cctcgtgctg    240
tcgcatgcag tcggtgtcgg cgagccgatg gcgcgttcgt cggtgcgtct gctgatcgcg    300
ctgaagctgt cgagcctcgg ccgcggccat tcgggcattc gccgcgaagt gatggacgcg    360
ctgatcaagc tgttcaacgc cgacgtgctg ccgctgattc cggtgaaggg ctcggtcggc    420
gcatcgggcg acctcgcgcc gctcgcgcac atgtcggccg tgctgctcgg cgtcggcgaa    480
gtgttcattc gcggcgagcg cgcgagcgcg gtggacgggt tgcgcgtcgc gggcctcgcg    540
ccgctgacgc tgcaggcgaa ggaaggcctc gcgctgctga acggtacgca ggcgtcgacg    600
gcgctcgcgc tcgacaacct gttcgcgatc gaagacctgt accgcacggc gctcgtcgcc    660
ggcgcgctgt cggtcgatgc ggcggccggc tcggtgaagc cgttcgacgc gcgcatccac    720
gaactgcgcg ccatcgcgg ccagatcgat gcggcggccg cgtatcgcga gctgctcgaa    780
ggctcggcga tcaacctctc gcatcgcgac tgcggcaagg tgcaggatcc gtacagcctg    840
cgctgccagc cgcaggtgat gggcgcgtgc ctggaccaga tgcgtcatgc ggccgacgtg    900
ctgctcgtcg aggcgaacgc ggtatcggac aacccgctga tcttcccgga taccggcgaa    960
gtgctgtcgg gcggcaattt ccatgcggag cccgtcgcgt tcgcggccga caacctcgcg   1020
ctcgcggctg cggaaatcgg cgcgctggcc gagcgccgca tcgcgctgct gatcgacgcg   1080
acgctgtcgg gcctgccgcc gttcctcgtg aaggatggcg gcgtgaactc gggcttcatg   1140
attgcgcacg tgacggcagc tgcgctcgca tcggagaaca agacgctcgc gcatccggcg   1200
tcggtcgatt cgctgccgac ctcggcgaac caggaagacc acgtgtcgat ggcgacgttc   1260
gcggcacgca agctggccga catcgccgac aacacgaagc acatcctcgc gatcgaactg   1320
ctcgcggccg cgcagggcgt cgatctgcgc gagaacgaga cgagcccgaa gctcgcggaa   1380
gtgatgaaga cgattcgcag caaggtcgcg cattacgagc tcgaccacta ctttgcgccg   1440
gacatcgccg tgatcgcgaa gctcgtcgtc gagcgcgcgt tcgcgaagca ctgcccgttc   1500
gccttcgcat cggagcagta a                                             1521
```

<210> SEQ ID NO 4
<211> LENGTH: 1533
<212> TYPE: DNA
<213> ORGANISM: Artificial Sequence
<220> FEATURE:
<223> OTHER INFORMATION: tyrosine ammonia-lyase

<400> SEQUENCE: 4

```
gtgacgcagg tcgtggaacg tcaggctgat cggctcagca gcagggagta cctggcccgg     60
gtcgtgcgca cgccgggtg gacgccggt ctcacctcgt gcaccgacga ggagatcgtc     120
cggatgggcg cgagcgcgcg caccatcgag gagtacctga agtccgacaa gcccatctac    180
ggcctgacgc agggcttcgg tccgctggtg ctgttcgacg ccgactcgga gctggagcag    240
ggcggctcgc tgatctcgca cctgggcacc ggccagggcg cgccactggc cccggaggtg    300
tcgcggctga tcctctggct gcgcatccag aacatgcgca aggggtactc ggcggtctcg    360
ccggtgttct ggcagaagct cgccgacctg tggaacaagg ggttcacccc ggcgatcccc    420
cggcacggca cggtcagcgc gagcggcgac ctgcaaccgc tggcgcacgc cgcgctcgcc    480
ttcaccggtg tcgcgaggc gtggacccgg acgccgacg gccggtggtc accgtgccg      540
gccgtggacg cgctcgccgc gctggggcg gagccgttcg actggccggt gcgcgaggcg    600
ctggcgttcg tcaacgggac cggcgcgagc ctcgcggtgg ctgtgctcaa ccaccggtcc    660
```

```
gccctgcggc tggtccgcgc ctgcgccgtg ctctccgcgc ggctggcgac cctgctgggg      720
gccaatcccg agcactacga cgtggggcac ggtgtcgcgc gcggccaggt cggtcagctg      780
accgcggcgg agtggatccg gcaggggctg ccccggggca tggtgcgcga cggcagccgc      840
ccgctccagg agccgtacag cctgcggtgc gcgccgcagg tgctcggcgc ggtgctcgac      900
cagctcgacg gcgcgggcga cgtgctggcg cgggaggtcg acggctgcca ggacaacccg      960
atcacctacg agggcgagct gctgcacggc ggcaacttcc acgccatgcc ggtgggtttc     1020
gcctccgacc agatcgggtt ggccatgcac atggccgcct acctggccga gcgccagctg     1080
ggtctgctgg tcagcccggt gaccaacggc gacctgccgc ccatgctcac cccgcgcgcc     1140
gggcgcggtg ccgggctggc cggggtgcag atcagcgcga cctcgttcgt ctcgcggatc     1200
cggcagctgt tgttccccgc ctcgctgacc accctgccga ccaacggctg gaaccaggac     1260
cacgtgccga tggcgctcaa cggggcgaac tcggtgttcg aggcgttgga gctcggctgg     1320
ctgacggtcg ggtcgctggc ggtgggcgtc gcgcagctcg cggccatgac cggccacgcc     1380
gcggagggcg tctgggcgga gctggccggg atctgcccgc cgctggacgc cgaccgcccg     1440
ctgggcgccg aggtgcgcgc cgcgcgcgac ctgctgtccg cgcacgcgga ccaactgctc     1500
gtcgacgagg cagacgggaa ggatttcgga tga                                  1533
```

```
<210> SEQ ID NO 5
<211> LENGTH: 1275
<212> TYPE: DNA
<213> ORGANISM: Artificial Sequence
<220> FEATURE:
<223> OTHER INFORMATION: glutamate dehydrogenase

<400> SEQUENCE: 5
```

```
atgtcagcaa agcaagtctc gaaagatgaa gaaaagaaag ctcttaactt atttctgtct       60
acccaaacaa tcattaagga agcccttcgg aagctgggtt atccgggaga tatgtatgaa      120
ctcatgaaag agccgcagag aatgctcact gtccgcattc cggtcaaaat ggacaatggg      180
agcgtcaaag tgttcacagg ctaccggtca cagcacaatg atgctgtcgg tccgacaaag      240
gggggcgttc gcttccatcc agaagttaat gaagaggaag taaaggcatt atccatttgg      300
atgacgctca aatgcgggat tgccaatctt ccttacggcg gcgggaaggg cggtattatt      360
tgtgatccgc ggacaatgtc atttggagaa ctggaaaggc tgagcagggg gtatgtccgt      420
gccatcagcc agatcgtcgg tccgacaaag gatattccag ctcccgatgt gtacaccaat      480
tcgcagatta tggcgtggat gatggatgag tacagccggc tgcgggaatt cgattctccg      540
ggctttatta caggtaaacc gcttgttttg ggaggatcgc aaggacggga acagcgacg       600 gcacagggcg tcacgatttg tattgaagag gcggtgaaga aaaagggat caagctgcaa       660 aacgcgcgca tcatcataca gggctttgga aacgcgggta gcttcctggc caaattcatg     720
cacgatgcgg gcgcgaaggt gatcgggatt tctgatgcca tggcgggct ctacaaccca      780 gacggccttg atatccctta tttgctcgat aaacgggaca gctttggtat ggtcaccaat      840
ttatttactg acgtcatcac aaatgaggag ctgcttgaaa aggattgcga tattttagtg      900
cctgccgcga tctccaatca atcacagcc aaaaacgcac ataacattca ggcgtcaatc      960
gtcgttgaag cggcgaacgg cccgacaacc attgatgcca ctaagatcct gaatgaaaga     1020
ggcgtgctgc ttgtgccgga tatcctacg agtgccggcg cgtcacggtt tcttatttt      1080 gaatgggtgc aaaacaacca aggatattat tggtcggaag aagaggttgc agaaaaactg     1140
```

| | |
|---|---|
| agaagcgtca tggtcagctc gttcgaaaca atttatcaaa cagcggcaac acataaagtg | 1200 |
| gatatgcgtt tggcggctta catgacgggc atcagaaaat cggcagaagc atcgcgtttc | 1260 |
| cgcggatggg tctaa | 1275 |

<210> SEQ ID NO 6
<211> LENGTH: 1419
<212> TYPE: DNA
<213> ORGANISM: Artificial Sequence
<220> FEATURE:
<223> OTHER INFORMATION: glutamate ammonia-lyase

<400> SEQUENCE: 6

| | |
|---|---|
| atgtccatca aagacgctgt aaaactgatt gaagaaagcg aagcccgctt tgtcgatttg | 60 |
| cgctttaccg ataccaaagg caagcagcac cactttaccg tgcctgcgcg catcgtgttg | 120 |
| gaagaccccg aagagtggtt cgaaaacgga caggcgtttg acggttcgtc catcggcggc | 180 |
| tggaaaggca ttcaggcttc cgatatgcag cttcgccccg atcccgccac ggcgtttatc | 240 |
| gatccttttt atgatgatgt taccgtcgtc attacctgcg acgttatcga tcccgccgac | 300 |
| ggtcagggtt acgaccgcga cccgcgctcc atcgcacgcc gcgccgaagc ctatttgaaa | 360 |
| tcttccggta tcggcgacac ggcatacttc ggtcccgaac ccgagttttt cgtcttcgac | 420 |
| ggcgtagaat ttgaaaccga tatgcacaaa acccgttacg aaatcacgtc cgaaagcggc | 480 |
| gcatgggcca gcggcctgca tatggacggt caaaacaccg gccaccgccc tgccgtcaaa | 540 |
| ggcggttacg cgcccgtcgc gccgattgac tgcggtcagg atttgcgttc cgcgatggta | 600 |
| aacattttgg aaggactcgg catcgaagtc gaagtgcacc acagcgaagt cggtaccggc | 660 |
| agccaaatgg aaatcggcac gcgcttcgcc accttggtca acgcgccga ccaaacccaa | 720 |
| gacatgaaat atgtgattca aaatgtcgcc cacaacttcg gcaaaaccgc caccttcatg | 780 |
| cccaaaccca ttatgggcga caacggcagc ggtatgcacg ttcaccaatc catctggaaa | 840 |
| gacggtcaaa acctgttcgc aggcgacggc tatgccggct tgagcgacac cgcgctctac | 900 |
| tacatcggcg gcatcatcaa acacgccaaa gccctgaacg cgattaccaa tccgtccacc | 960 |
| aactcctaca acgccttgt gccgcacttt gaagcgccga ccaaactggc atattccgcc | 1020 |
| aaaaaccgtt ccgcttccat ccgtattccg tctgtgaaca gcagcaaggc gcgccgcatc | 1080 |
| gaagcgcgtt tccccgaccc gaccgccaac ccgtacttgg cgttcgctgc cctgctgatg | 1140 |
| gcgggtttgg acggcattca aaacaaaatc catccgggcg atcctgccga taaaaatctc | 1200 |
| tacgacctgc cgccggaaga gacgcgctc gtcccgaccg tttgcgcttc tttagaagaa | 1260 |
| gccctcgccg cgctcaaagc cgaccacgaa ttcctcttac gcggcggcgt gttcagcaaa | 1320 |
| gactggatcg acagctacat cgcctttaaa gaggaagatg tccgccgcat ccgtatggcg | 1380 |
| ccgcatccgc tggaatttga aatgtattac agcctgtaa | 1419 |

<210> SEQ ID NO 7
<211> LENGTH: 1075
<212> TYPE: DNA
<213> ORGANISM: Artificial Sequence
<220> FEATURE:
<223> OTHER INFORMATION: threonine dehydrogenase

<400> SEQUENCE: 7

| | |
|---|---|
| aggaggtgtt ttaataatga aaggttttgc aatgctcagt atcggtaaag tcggttggat | 60 |
| tgaaaaagaa aagcctactc ccggcccttt tgacgctatt gtaagacctc tagctgtggc | 120 |
| cccttgcact tcggacgttc ataccgtttt tgaaggtgct attggcgaaa gacataacat | 180 |

```
gatactcggt cacgaagctg taggtgaagt agttgaagta ggtagtgagg taaaagattt    240
taaacctggt gatcgcgttg tggtaccagc tattacccct gattggcgaa cctctgaagt    300
gcaaagagga tatcaccaac actctggtgg aatgctggca ggctggaaat tttcgaatat    360
aaaagatggt gttttttggtg aattttttca tgtgaacgat gctgatatga atttagcaca   420
```

```
gatactcggt cacgaagctg taggtgaagt agttgaagta ggtagtgagg taaaagattt    240
taaacctggt gatcgcgttg tggtaccagc tattacccct gattggcgaa cctctgaagt    300
gcaaagagga tatcaccaac actctggtgg aatgctggca ggctggaaat tttcgaatat    360
aaaagatggt gttttttggtg aattttttca tgtgaacgat gctgatatga atttagcaca   420
tctgcctaag gaaattccat tggaagctgc agttatgatt cccgatatga tgactactgg    480 cttttcacgga gccgaactgg cagatataga attaggtgcg acggtagcgg ttttgggtat   540
tggcccagta ggtcttatgg cagtcgctgg tgccaaattg cggggtgctg aaggattat    600 cgcagtaggc agtagaccag tttgtgtaga tgctgcaaaa tactatggag ctactgatat    660
tgtaaactat aaagatggtc ctatcgacag tcagattatg gatttaacgg aaggcaaagg   720
tgttgatgct gccatcatcg ctggaggaaa tgttgacatc atggctacag cagttaagat    780
tgttaaacct ggtggcacca tcgctaatgt aaattacttt ggcgaaggag atgttttgcc    840
tgttcctcgt cttgaatggg gttgcggcat ggctcataaa actataaaag gcgggctatg    900
ccccggtgga cgtctaagaa tggaaagact gattgacctt gttgtttata agcgtgtcga    960
tccttctaag ctcgtcactc acgttttccg gggatttgac aatattgaaa agcctttat    1020 gttgatgaaa gacaaaccaa aagacctaat caaacctgtt gtaatattag cataa         1075

<210> SEQ ID NO 8
<211> LENGTH: 1545
<212> TYPE: DNA
<213> ORGANISM: Artificial Sequence
<220> FEATURE:
<223> OTHER INFORMATION: threonine ammonia-lyase

<400> SEQUENCE: 8
atggctgact cgcaacccct gtccggtacc ccggaaggtg ccgaatattt aagagcggtg     60
ctgcgcgcgc cggtctacga agcggcgcag gtcacgccgc tacagaaaat ggaaaaactg    120
tcgtcgcgtc tcgataacgt gattctggtg aagcgcgaag atcgccagcc agttcatagc    180
tttaagttgc gcggcgcata cgccatgatg gcgggcctga cggaagaaca aaaagcacac    240
ggcgtgatta ccgcttctgc aggtaaccac gcgcagggcg tcgcgttttc ttccgcacgg    300
ttaggcgtga aggcgctgat cgtcatgcca accgccaccg ccgatatcaa agttgatgcg    360
gtgcgcggct ttggcggcga agtgctgctt cacggcgcaa atttcgatga agcgaaagcg    420
aaagcgatcg aactgtcaca gcagcagggt ttcacctggg taccgccgtt cgatcatccg    480
atggtgatcg ccgggcaagg cacgctggcg ctggaactgc tccagcagga cgcccatctc    540
gaccgcgtat ttgtaccggt cggcggcggc ggtctggcag cgggtgtggc ggtgctgatc    600
aaacaactga tgccgcaaat caaagtaatc gccgtggaag cggaagattc cgcctgcctg    660
aaagcggcgc tggatgcggg tcatcccgtt gatctgcccc gcgtggggct gtttgctgaa    720
ggcgtcgcgg taaaacgcat cggcgatgaa accttccgtt tgtgccagga gtatcttgac    780
gacatcatca ccgtcgatag cgatgccatc tgtgcggcga tgaaagatct gttcgaagat    840
gtgcgcgcgg tggcggaacc ttccggcgcg ctggcgctgg cggggatgaa aaaatacatc    900
gcccagcaca acattcgcgg tgaacggctg gcgcatattc tttccggtgc taacgtgaac    960
tttcacggtc tgcgctacgt ctcggaacgc tgcgaactgg cgaacagcg tgaagcgttg   1020 ttggcggtga ccattccgga agaaaaaggc agcttcctca aattctgcca actgcttggc   1080
gggcgttcgg tcaccgagtt caactaccgt tttgccgatg ccaaaaacgc ctgcatcttt   1140
```

| | |
|---|---|
| gtcggcgtgc gcttaagccg tggcctcgaa gagcgcaaag aaattttgca gatgctcaac | 1200 |
| gacggtggct acagcgtggt tgatctctcc gacgacgaaa tggcgaagct gcatgtgcgc | 1260 |
| tatatggttg gcgggcgtcc atcgcatccg ttgcaggaac gcctatacag cttcgaattc | 1320 |
| ccggaatcac cgggcgcgct gctgcgcttc ctcaacacgc tgggtacgca ctggaacatc | 1380 |
| tcgctgttcc attatcgcag ccacggtacc gactacgggc gcgtactggc ggcgttcgag | 1440 |
| cttggcgatc atgaaccgga ttttgaaacc cggttgaatg aactgggcta cgattgccac | 1500 |
| gacgaaacca ataacccggc gttcaggttc tttttggcgg gttag | 1545 |

<210> SEQ ID NO 9
<211> LENGTH: 750
<212> TYPE: DNA
<213> ORGANISM: Artificial Sequence
<220> FEATURE:
<223> OTHER INFORMATION: serine dehydrogenase

<400> SEQUENCE: 9

| | |
|---|---|
| atgagcggta ccatcctcat caccggcgcc acgtccggct tcggacaggc cacggcgcgg | 60 |
| cgtttcgtca aggaaggctg gaaggtcatc ggcacaggtc ggcgggcgga acggctggag | 120 |
| gcgctggcgc aagaactcgg ctccgccttt cacgcgctg ccttcgatgt taccgacgaa | 180 |
| gatgccacta gaaaggcact tgcggctttg ccggaaggtt ccgggacat cgatattctc | 240 |
| gtcaacaatg cggggcttgc gctcggcacc gcacctgcac cgcaggtgcc gctgaaagac | 300 |
| tggcagacca tggtgaacac caacatcacc ggtcttttga acatcaccca ccatcttttg | 360 |
| cccacgttga tcgaccgcaa gggcattgtc atcaaccttt cctcggtagc tgcgcactgg | 420 |
| ccctatgcgg gcggcaatgt ctatgccgga acgaaagcct tcctgcggca attctcgctc | 480 |
| ggtctgcgct ccgacctgca tggcaagggc gtgcgcgtca cctcgatcga accgggcatg | 540 |
| tgcgaaacgg aattcacgct tgttcgcacc ggcggcaatc aggatgcctc ggacaatctt | 600 |
| tacaagggcg tcaatccgat cacggccgag atatcgcca atacgatcca ttgggtcgcc | 660 |
| tcgcagccca acatatcaa catcaacagc ctcgaactca tgccggtcaa ccagtccttt | 720 |
| gccggttttcc aagtgcatcg ggaaagttga | 750 |

<210> SEQ ID NO 10
<211> LENGTH: 1380
<212> TYPE: DNA
<213> ORGANISM: Artificial Sequence
<220> FEATURE:
<223> OTHER INFORMATION: serine ammonia-lyase

<400> SEQUENCE: 10

| | |
|---|---|
| atgatgacca aaacgaaat ccaaaagtgg gtaaaggaat cccgctgct tgaaacgatc | 60 |
| atggcggccg aagaggtatt tggcgcaat ccaaaatatc acgcgtttgc gcaagctatt | 120 |
| cgaacgattc ctttacgcga acgcgatgtc aaggaggccg aagagcgatt gcgccgcttt | 180 |
| gccccctaca tcgcgaaagt gtttcccgag acgcgaacgg cccacggtat catcgaatcc | 240 |
| ccttttagtgc ggattccgaa catgaaacag cgtttggaaa agatgtttca gaccaacatc | 300 |
| gagggggatc tgttgctaaa atgcgacagc catcttccca tctccggatc gatcaaggcg | 360 |
| agagggggaa tctacgaggt tctgaaacat gcggaagaac tcgctctggc aaaccatatg | 420 |
| atcaccatgg gggatgacta tgcggtcatg ccagcgaag aattccggca gttcttttcc | 480 |
| cgctattcgc ttgtcgttgg ttcgacggga aatttaggct tgagtatcgg catcatcggg | 540 |
| gcgcagcttg ggttccgcgt taccgttcat atgtcagccg atgcgaaaca atggaaaaaa | 600 |

```
gacttgttgc gaagcaaagg ggttgcggtc atcgaacatc tcaccgacta caacaaggtg    660
gtggaagagg cgcgaagaca gtccgccgag gatccaacgt cgtattttat cgatgatgag    720
aactcgatcc atctgttttt aggctatgcg gtggcggcgt ttcggctgaa aaagcaatta    780
gaggacatga acatcacggt tgatgaaaac cacccgctct ttgtatatct tccttgcggc    840
gtcggcggcg gtccgggcgg ggtgacgttt gggctgaagc tcgtgtacgg cgatcatgtc    900
cattgctttt tcgctgagcc gacgcattcg ccttgcatgt tgctcggcct gatgacggga    960
cagcacgacc gcgtgtcggt gcaagatttt ggcctcgaca ataagaccga agcggacggg   1020
ctagcggtgg ggcggccgtc aaggttggtg gggaacatgc ttgagaacgt catcagcggc   1080
gtctatacgg tggacgatgc gacgctttac cgcttgctcg cggcgatggt ggaaacggag   1140
gaaatctatt tagagccgtc cgccttggcg ggggtggcgg ggcctgttcg gctgtttcgt   1200
gatttggcgg ggcaaacgta cgtagaggca aacggtttga agaaaagat gaaaaacgcc    1260 gtccatattg gctgggcgac aggcggaagc atggtgctaa aggatgtgat ggaggcctat   1320
tatcgggaag gcgtgcgcat cgaaacgatg acagggaacg gttttctga aggacgataa    1380
```

<210> SEQ ID NO 11
<211> LENGTH: 1047
<212> TYPE: DNA
<213> ORGANISM: Artificial Sequence
<220> FEATURE:
<223> OTHER INFORMATION: leucine dehydrogenase

<400> SEQUENCE: 11

```
atgctgatgt tcgaagaaat ccaggcgcgc ggccacgaga gcgtcacgct gctgcaccac     60
gcccccagcg gcctgcgcgc cgtgctcgcc gtgcactcca ccgtgctcgg ccctgccatt    120
gccggctgcc gcctgatgcc ctgcaccgag gaacgcgccg tgcgcgacgc cctcgccctc    180
agcgagtccg tcacgctcaa ggccgccctc gcgggcctga actacggcgg gggcgcgtgc    240
gtcatgctcc ccccggaagg cggcgacatc gacgggcacg cccgcgaggc gctgttccgc    300
gcgctcggcc ggcagatccg ttaccgcggt ggccgcgtca tcctcaccga ggacgtcggc    360
gtgaccggcc gcgacatcgc cttcgccgcg caggaaaccg acagcaccat gggcatgcac    420
accgacacgc ccaccgtcac cgcgtacggc gtgtaccgcg gcatcaaggc cgccgcgcgc    480
gcctacctcg gcggcgagag catgcgcggc gtgcgcgtcg cgctgctcgg cgcgggcgca    540
gtcgggcgca ccctcgcgca gcacctgcac cgcgagggcg cgcgcctcac cgtcgcagac    600
ctgatgtctg agcgcgcgca ggccctcgcg gacgacctcg gcgagcgcgt caccgtcgtg    660
agcgccgctg acatcttcga cgtgccgtgc gacgtattcg cgccgtgcgc gttcgggcac    720
agcatcaaaa gcgccgacgt gccccgcttg cagtgccggg tgatcgccgg cagcgaacac    780
cacccgctca gccacaacgg cgagacgctc gtgcgcgaag cgggcatcac atacatcccg    840
gacttcgcca tcaacagcgc cggcctgatg agccgccgcg agaacctcag catcgaaacg    900
gcggcggaac gcgtgtacga gagcgtcgcg cagatctgcg cgaccgcgca gaagtacgag    960
aagccgccgc acgtcgtcgc ccgtaaaactc gcgctgcgcc gcatcgaact gatcggctcc   1020
atcagcggcc agtacgccgg ccagtaa                                        1047
```

<210> SEQ ID NO 12
<211> LENGTH: 768
<212> TYPE: DNA
<213> ORGANISM: Artificial Sequence
<220> FEATURE:

<223> OTHER INFORMATION: aspartate dehydrogenase

<400> SEQUENCE: 12

| | | | | | |
|---|---|---|---|---|---|
| tcatgtgcca | acacgtatgt | tatcacttaa | aattttagt | aaagtgactg | ctgaatatgc | 60 |
| tgccaaaaca | cttgtttttg | gatttaattc | acacacagtg | ttttttgtta | tagatttaaa | 120 |
| ctctccaaaa | tctcctttaa | catggacttc | atggatattg | tgttcaactt | caggatctgc | 180 |
| aattatcttt | acatccgcat | ctattccaga | ggctagactt | aatgccgcag | caacgttaat | 240 |
| attcactgga | aatttttaa | cagcttctga | ggatttccct | ttaaacacga | cctcctttt | 300 |
| tttggtctta | acacctaacg | aagtaggtga | ttttctcgtt | ataagtttta | tttcttttat | 360 |
| cttacctaag | gatgcggctt | ttacaccatc | taaaccaatt | attgcaccgg | aaggtatgta | 420 |
| tatattagct | cctgattctc | tagattcctt | tatcaatctt | cttctaactt | tctcatctaa | 480 |
| tagtgcaccc | acactcataa | tcaaaacatc | tatacctcta | ctaattatat | tgggcacaat | 540 |
| ttcttttact | gcctcttgag | aagcagattc | aattatcaaa | tcaactccat | tgaacatttc | 600 |
| ttctaccttt | tttacggcag | tgccatttgt | taaatttgct | agcttcttag | cttttctaaa | 660 |
| atttctgtca | taaaaatatt | ttaattttat | ttttttgata | tcttgtttta | agacaaggtt | 720 |
| aactattgta | tttgcaattg | caccacatcc | tataatccca | catctcat | | 768 |

<210> SEQ ID NO 13
<211> LENGTH: 1425
<212> TYPE: DNA
<213> ORGANISM: Artificial Sequence
<220> FEATURE:
<223> OTHER INFORMATION: aspartate ammonia-lyase

<400> SEQUENCE: 13

| | | | | | |
|---|---|---|---|---|---|
| atgtcctcgc | ctgcatcatc | gcgcatcgaa | aaagacctgc | ttggtgttct | cgaagtacct | 60 |
| gccaacgcgt | attacggcat | ccagaccctg | cgagcggtga | acaactttca | cctctccggc | 120 |
| gtgccgcttt | cgcactaccc | gaaactggta | gtcgcgctgg | ccatggtcaa | gcaggcggca | 180 |
| gcggatgcaa | accatcagct | cggacacctc | aatgacgcca | agcatgcggc | gatcagcgag | 240 |
| gcctgtgccc | gcctgatccg | cggcgacttc | acgatcagt | tcgtggtcga | catgatccag | 300 |
| ggcggcgctg | gcacgtcgac | caacatgaat | gccaacgaag | tcatcgccaa | catcgctctg | 360 |
| gaaaccatgg | gtttcgagaa | aggcgcatac | aaacacctgc | accccaacaa | cgatgtcaac | 420 |
| atggcgcagt | cgaccaacga | cgcctacccc | acggcgatcc | gcttgggtct | gctgctgggt | 480 |
| cacgacgctc | tgctcgccag | cctttccagc | ctgattcagg | ccttcgccgc | caagggcgaa | 540 |
| gaattcaacc | atgtgctgaa | gatgggccgc | acccagttgc | aggacgccgt | tccaatgacc | 600 |
| ctgggtcagg | aattccgcgc | cttcgccacc | accctgacag | aagacctgaa | ccgcctgcgc | 660 |
| agcctggcgc | cagagctgtt | gaccgaagtg | aacctcggcg | gaaccgccat | cggcaccggc | 720 |
| atcaacgccg | accctggcta | tcagaagctg | gcagtcgatc | gtctggcact | catcagcggc | 780 |
| cagcctctgg | tgccagcagc | cgacctgatc | gaagcgacct | ccgacatggg | cgccttcgtg | 840 |
| ttgttctcgg | gcatgctcaa | gcgtactgcg | gtcaagctgt | cgaaaatctg | caacgacctg | 900 |
| cgcctgctgt | ccagcggccc | acgcaccggc | atcaacgaaa | tcaacctgcc | ggcacgtcag | 960 |
| ccaggcagct | cgatcatgcc | cggcaaggtc | aacccggtga | tcccggaagc | ggtcaatcag | 1020 |
| gttgcctcg | aaatcatcgg | caacgacctg | tcgctgacca | tggcagccga | aggaggacaa | 1080 |
| ttgcagctca | acgtgatgga | gccgctgatc | gcctacaaga | tcttcgactc | gatccgcctg | 1140 |
| ctgcagcgcg | ccatggacat | gctgcgcgag | cactgcatcg | tcggcatcac | agccaacgaa | 1200 |

```
cagcgctgcc gcgagctggt cgagcattcg atcggtctgg tcaccgccct gaacccttac    1260
atcggttacg agaactccac ccgtatcgcc cgcatcgcgc tggaaaccgg ccgcggcgtg    1320
ctggaactgg tgcgtgagga aggtctgctc gacgacgcca tgctcgacga catcctgcgc    1380
ccggaaaaca tgatcgctcc gcgtctggcc cccttgaagg cctga                   1425

<210> SEQ ID NO 14
<211> LENGTH: 1083
<212> TYPE: DNA
<213> ORGANISM: Artificial Sequence
<220> FEATURE:
<223> OTHER INFORMATION: valine dehydrogenase

<400> SEQUENCE: 14
tcagcgaccg cgggcctcgg ccatccgctg ctcggcgatc cggtcggccg ccgcggcggg      60
cggaatgccg tccgccttcg cacgtgcgaa tatttccagc gtggtgtcga agatcttcgt    120
cgccttcgcc ttgcaccggt cgaagtcgaa cccgtgcagc tcgtcggcga cctggatcac    180
gccgccggcg ttgaccacat agtcgggtgc gtagaggacc gaccggtcgg ccaggtcctt    240
ctcgacaccc gggtgggcca gctggttgtt ggccgcgccg cacaccacct cgccgtgag    300 caccggaacg gtcgcgtcgt tgagcgcgcc gccgagcgcg cagggcgcgt agatgtcgag    360
accctcggtg cggatcagcg tctcggtgtc cgccaccacg tgacctcgg ggtgcagatc    420 ggtgatccgg cgcaccgact cctcgcgtac gtcggtgatc acgacctcgg ccccgtcgga    480
gagcaggtgc tcgacgaggt ggtggcccac cttgccgacc ccggcgacgc cgaccttgcg    540
gccgcgcagc gtcgggtcgc cccacaggtg ctgggccgag gcccgcatgc cctggaagac    600
accgaacgcg gtgaggacgg aggagtcgcc ggcgccgccg ttctcggggg agcggccggt    660
ggtccagcgg cactccctgg cgacgacgtc catgtcggc acgtaggtgc cgacatcgca    720
ggcggtgacg taccggccgc cgagcgaggc gacgaaccgg ccgtaggcca ggaggagttc    780
ctccgtcttg atcttctccg ggtcgccgat gatgacggcc ttgccgccac cgtggtcgag    840
tccggccagg gcgttcttgt acgacatccc gcgcgacagg ttcagcgcgt cggcgacggc    900
ctcggcctcg gtcgcgtacg ggtagaagcg ggtgccgccg aggccgggc ccaggcggt    960 ggagtggagg gcgatgacgg ccttgaggcc ggtggcacgg tcctggcaga tcacgacttg   1020
ctcgtgaccc ccctgatccg agtggaacag ggtgtgcagg acgccgttag tcacatcggt   1080
cac                                                                1083

<210> SEQ ID NO 15
<211> LENGTH: 2910
<212> TYPE: DNA
<213> ORGANISM: Artificial Sequence
<220> FEATURE:
<223> OTHER INFORMATION: glycine dehydrogenase

<400> SEQUENCE: 15
ctagttgtaa aagtcgaggg aggcgcaact gcacatgagg tgacgatctc cgtaaacccc      60
gtcaatgcga cccacagtcg gccagtactt ttcaacgtac gagtaaggat aagggaatgc    120
cgccaaacgc cgatcatatg gtttgtccca tttatcatcg gtgacacatc ttgccgtgtg    180
tggtgcattc ttcaaaacat tgttatccac tggttgttca ccttttttcaa tggcggcaat    240 ctcacctcga atggaaatta gtgcatctgc caagcgatcc aactcccgct ggggttctga    300
ttcggtgggt tcaatcatta aagtcccggg tacaggaaac gccagtgttg gcgagtgaat    360
```

```
tccgtagtcc atcaaccgtt tggccacgtc ctccgcctca atatgagctg tcttcttgaa    420
ccgtcgaaga tcaacgataa actcatgagc gcagtagttt tctccaccca ggaaaagaat    480
cgtataatgg ttctctaggc gcttcttcaa gtagtttgca ttcaaaacgg cgtactctgt    540
acaagttttg agcccgtgtg atccaagcat taacatcaac atgtacgata tcggaagaat    600
tgatgctgat ccgtacgctg attgtgagac ttggccgaat ggctgtgaac cgccaacttt    660
ttggttgaaa acagaatttg gcaaaaaggg ggccagatgt tgacggacag ctatagggcc    720
cattccgggg ccgccaccac catggggaat tgaaaacgtc ttgtggagat taatgtggca    780
cacgtcgcca ccgatatatc cagggcctgt atagccaacc atggcgttaa gatttgcccc    840
atcaatgtag cattgtccac cgtagtagtg cgccattgat gtaatggata aaatatcctt    900
gtcaaacaag ccatacgtac ttggatatgt tatcatgata cacgacaact cctttgcgtg    960
tttttggcaa gatttctcca ggtcattgat atcaaccctg ccgttagaca agcatttcac   1020
caagacaata ttcattcctg ccaatgttgc cgaagctgga ttcgtaccat gcgcactctc   1080
tggaatcaaa cagacgttgc ggtgtccttc cttcattgat agatggtacg cacgaataac   1140
acgaagccca gcgtattcac cttgggcgcc actattaggc tgaagcgata ccgcatccag   1200
accggtaatt tcccttaact tttgctcaag atctagacac aacgcactgt accctcgcac   1260
ttggtccact ggggcaaggg gatgcacatt ggtgaattct ggccaagaga gtggtaacat   1320
agcagcggca gggttaagct tcatggtgca agatcccaac gggacgcaac catgcgtaag   1380
gccgtaatcc tttcgttgta gacgatgaat atagcgcatc agttcacttt cactcttgta   1440
cttttgaaac gttgagtgtt tcaggaaatc agacttccgc accagatcca acggtagtac   1500
cgatttctga tcggctattt tggaaagggc tgcgacgacg ggaagcttca accctgcagc   1560
ctccaaaagt gacacaatgt gtccatccgt tgttgcctca tccacagaaa tggagacagt   1620
cccattactg taatcaacaa aaacattaat acccttctca acacatcgtg tcttgtaatc   1680
ctccgctgta atgcctttta ggttcacagt aacagtgtcg aaaaatgcac tgtttaccac   1740
agagtgtcct actgattcca taccaacagc gagcactttc gccttgccgt gtatctcatt   1800
ggcaatctca tttagaccat ctggaccatg gtaggcggca taaacccac tcacgttggc   1860 caataacgct tgtgcagtac agatatttga tgtggcgcgc tcacgcttaa tatgttgttc   1920
acgtgtctgc agcgccatgc gtatggatgg ctctccggca gaatccttac tgacgccgat   1980
cacacgtccc ggcatcaacc tcttaaactg ctccttgaca gcaaagaacg cggcgtgagg   2040
acctccatat cctagtggaa caccaaaacg ctgggaggat cccacaacca catctgcatt   2100
catttcacca ggtggcttga caagaacaca agccatcaag tcggtcccac agcaactaat   2160
gacaccgtgc ttctttgcat tctcgaacag tggtgagaag tcatgaagca tgcccatcgc   2220
atctggtgtt tgtacaagga taccaaacaa ggaactgtca gtccagtcaa tcagattcgt   2280
gtcgcccacg acgacgttta tcttgagcgg ttcggctctt gtcttaacca tctcaatgca   2340
ggatggaaaa acagttttg atacgaagaa cgtattccgc tttcgttgac catgctgaaa    2400
agcaagatgc atcgcctcgg atgatgctgt cgcttggtca agaagagatg catttgccac   2460
atccatcttt gtcaaatcca taaccatggt ttggaaattc aaaagggact ccagacgtcc   2520
ttgtgcaatc tcagcttggt atggtgtgta gggtgtgtac catccaggat ttcaatgac    2580 gttgcgaagt atgacaggag gagtaatgga ctcgtagtac ccctgaccaa tcatgctttt   2640
tagtaccttg tttcgcgcac caagagagcg cacgagtgcg agagcatcca tctcactcat   2700
agccgccacc tccgtcaagg gtgggcgtac aatatcccct ggaatagcag ccgtcatcaa   2760
```

| atcagagaga ctctcttttc caaccgttcg aagcatcgac attgtctcag ccgttgttgg | 2820 |
| accaatatgg cggttaatat agctgtccgt ggcagtccat cgaacaaatg tcacgcatgg | 2880 |
| caaagagcca cgaaacaaac gacggtacat | 2910 |

<210> SEQ ID NO 16
<211> LENGTH: 1107
<212> TYPE: DNA
<213> ORGANISM: Artificial Sequence
<220> FEATURE:
<223> OTHER INFORMATION: alanine dehydrogenase

<400> SEQUENCE: 16

| atgatcattg gcctgccgaa agagatcaaa gttaaggaaa accgcgtggc actcacgccc | 60 |
| gggggcgtcg ccagcctcgt gcgccgcggc cacaccgtca tcgtggaacg cagcgccggc | 120 |
| gtgggcagcg gcatccagga caccgagtac gagcaggccg cgcgcagct cggcagcgcc | 180 |
| gccgaggcgt gggccgcgca gatggtcgtg aaggtcaagg agcccatcaa gagcgaatac | 240 |
| gggtacctcc gcccggacct gctgctgttc acgtacctgc acctcgctgc ggaccagccc | 300 |
| ctcacggacg ccctgctgag cgccggcacg accgccgttg cgtacgagac ggtgcagctc | 360 |
| gacgaccgca gcctgccgct gctcacgccc atgagtgagg tcgcgggccg cctgagcgtg | 420 |
| caggccggcg cgtaccacct gcaaaagccc atcggcgggc gcggcgtgct gctcggcggc | 480 |
| gtgccgggcg tgcaggcggg ccacgtcgtc gtgattggcg gcggcgtcgt cggcacgaac | 540 |
| gccgcgaaaa tggccatggg cctcggcgcg aaggtcacgg tgctggacgt gaaccacggg | 600 |
| cgcctctcgt acctcgacga cgtgttcttc gggaagctca ccaccatgat gagcaacgag | 660 |
| gcgaacatcc gctccatcct gcccgaagcg gacctcgtga tcggcggcgt gctgatcccc | 720 |
| ggggcgaagg cgccgcacct tgtcacgcgc gacatgctgg cgaccatgca ggaaggcagc | 780 |
| gtcatcgtcg acgtggcggt ggaccagggc ggatgcgtgg agaccattca cgcgacgacg | 840 |
| cacgacgatc ccacgtacat cgtggacggc gtgatccact acggcgtggc gaacatgccg | 900 |
| ggcgcggtgc cgcgcaccag cacgttcgcg ctcacgaacc agaccattgg gtacgtgctg | 960 |
| cagctcgcgg acaagggcgt ggaggcactc agcgccagca gccgctgct cgtggcctg | 1020 |
| aacaccatcg gcgggaagct gacgtacgcg ggcgtcgcgg aagcgttcgg cctgacgtac | 1080 |
| accgcgcctg aagtggcgct ggcgtaa | 1107 |

<210> SEQ ID NO 17
<211> LENGTH: 948
<212> TYPE: DNA
<213> ORGANISM: Artificial Sequence
<220> FEATURE:
<223> OTHER INFORMATION: proline dehydrogenase

<400> SEQUENCE: 17

| atggagccca ctatgagcca attcgaacag ctgtaccgcc aggtggccct cagtgtcgcc | 60 |
| ggcaacccgg tcgtggaaaa agtcttgagc aagcagggct gggcgctggc gcagcgtttt | 120 |
| gtatcgggcg agacggcgca ggacgccatc aaggccatca agcggctgga agcccagggc | 180 |
| atctccggca acctcgacct gctgggcgag ttcgtgaaca ccccggaacc cgccaatgcc | 240 |
| aacaccgaga tgattctggc gaccattgac caggtgcacg cggcgggcct cacgccctac | 300 |
| aacagcgtga aaatgtcggc gctgggccaa ggcagaccg cgccgacgg ccaggacctc | 360 |
| ggctacgtca acacccgccg cgtcgtggag cgggccaagc gctacggcgg cttcgtcaat | 420 |

```
ctggacatgg aagaccacac ccgcgtggac tcgactctgc agattttccg ccgcctggtc      480
aaggagttcg gccaccagca tgtgggaacg gtgttgcagg cctacctgca ccgctcggaa      540
gacgaccgcc gcagcctgga cgacctgcgc cccaacctcc gcatggtgaa gggcgcctac      600
ctggagcccg cctccgtcgc cctgcagagc aaaaccgaca ttgacgccgc ctaccgccgc      660
ctggtctacg agcacctcaa ggccggcaac tactgcaacg tggccaccca cgaccaccac      720
atcatctacg acgtgatgca ctttgcgctg gcccacggca tccctaagga ccagttcgaa      780
ttccagctgc tgtacggcat ccgcgaggac ctgcagcgcg aattggccga ggccggctac      840
acggtgcgct cgtacattcc tttcggcaag gactggtacg gctactactc gcgccgcatc      900
gccgagcgcc gcagaacgt gatgttcgtg ctgcgcggcc tgctgtaa                    948

<210> SEQ ID NO 18
<211> LENGTH: 1101
<212> TYPE: DNA
<213> ORGANISM: Artificial Sequence
<220> FEATURE:
<223> OTHER INFORMATION: lysine dehydrogenase

<400> SEQUENCE: 18
atgaaaaaca ttgtggttat cggcgcgggc aatatcggtt cggcaatcgc ctggatgctg       60
gccgcatcag gcgattatcg catcaccggtt gccgatcgtt cagccgatca gctggccaat     120
gtgccggcgc atgaacgggt cgacatcgtc gacattaccg accgtcccgc tctggaagca     180
ctgctaaaag gcaaattcgc cgtgctctcc gccgccccca ccgaattcca cctgacggcg     240
ggtattgccg aagcggccgt tgccgtcggc acgcattatc tcgatctcac cgaagacgtg     300
gaatccaccc gcaaggtcaa ggcgctggcg aaacggccg aaaccgcgct cattccgcaa      360
tgcggcctcg cccccggctt catctccatc gtcgctgccg atctcgccgt caagttcgac     420
aagctggaca gcgtgcgcat gcgcgtcggc gctctgccgc aatatccgtc caatgcgctc     480
aactacaacc tcacctggag taccgacggg ctgatcaacg aatatatcga gcccctgcgaa    540 ggattcgtcg aaggccgcct caccgccgtt ccggcccttg aggagcgcga ggagttctcg     600
ctcgatggca tcacctacga ggcgttcaac acctcgggcg gtctcggtac gctttgcgcg     660
acgctggaag gcaaggtgcg gaccatgaac taccgcacta tccgttatcc cggccatgtg     720
gcgatcatga aggcgctttt gaacgacctc aacctgcgca accgccgcga tgtgctgaag     780
gacctgttcg aaaacgccct gccccggcacc atgcaggatg tggtcatcgt cttcgtcacc     840
gtctgcggca cccgcaacgg ccgcttcctg caggaaacct atgccaacaa ggtctatgcc     900
ggcccggttt ccggccggat gatgagcgcc atccagatca ctaccgccgc cggcatctgc     960
acggttctcg acctgctcgc ggaaggcgcc ctgccgcaga agggcttcgt tcgacaggag    1020
gaagtggcgc tgccgaagtt cctcgaaaac cggtttggcc ggtattatgg ctcgcatgag    1080
ccgctggcgc gggttgggtg a                                              1101

<210> SEQ ID NO 19
<211> LENGTH: 366
<212> TYPE: PRT
<213> ORGANISM: Thermoactinomyces intermedius

<400> SEQUENCE: 19

Met Arg Asp Val Phe Glu Met Met Asp Arg Tyr Gly His Glu Gln Val
 1               5                  10                  15

Ile Phe Cys Arg His Pro Gln Thr Gly Leu Lys Ala Ile Ile Ala Leu
            20                  25                  30
```

His Asn Thr Thr Ala Gly Pro Ala Leu Gly Gly Cys Arg Met Ile Pro
            35                  40                  45

Tyr Ala Ser Thr Asp Glu Ala Leu Glu Asp Val Leu Arg Leu Ser Lys
 50                  55                  60

Gly Met Thr Tyr Lys Cys Ser Leu Ala Asp Val Asp Phe Gly Gly Gly
 65                  70                  75                  80

Lys Met Val Ile Ile Gly Asp Pro Lys Lys Asp Lys Ser Pro Glu Leu
                    85                  90                  95

Phe Arg Val Ile Gly Arg Phe Val Gly Leu Asn Gly Arg Phe Tyr
                    100                 105                 110

Thr Gly Thr Asp Met Gly Thr Asn Pro Glu Asp Phe Val His Ala Ala
            115                 120                 125

Arg Glu Ser Lys Ser Phe Ala Gly Leu Pro Lys Ser Tyr Gly Gly Lys
    130                 135                 140

Gly Asp Thr Ser Ile Pro Thr Ala Leu Gly Val Phe His Gly Met Arg
145                 150                 155                 160

Ala Thr Ala Arg Phe Leu Trp Gly Thr Asp Gln Leu Lys Gly Arg Val
                165                 170                 175

Val Ala Ile Gln Gly Val Gly Lys Val Gly Glu Arg Leu Leu Gln Leu
                180                 185                 190

Leu Val Glu Val Gly Ala Tyr Cys Lys Ile Ala Asp Ile Asp Ser Val
            195                 200                 205

Arg Cys Glu Gln Leu Lys Glu Lys Tyr Gly Asp Lys Val Gln Leu Val
    210                 215                 220

Asp Val Asn Arg Ile His Lys Glu Ser Cys Asp Ile Phe Ser Pro Cys
225                 230                 235                 240

Ala Lys Gly Gly Val Val Asn Asp Asp Thr Ile Asp Glu Phe Arg Cys
                245                 250                 255

Leu Ala Ile Val Gly Ser Ala Asn Asn Gln Leu Val Glu Asp Arg His
            260                 265                 270

Gly Ala Leu Leu Gln Lys Arg Ser Ile Cys Tyr Ala Pro Asp Tyr Leu
    275                 280                 285

Val Asn Ala Gly Gly Leu Ile Gln Val Ala Asp Glu Leu Glu Gly Phe
290                 295                 300

His Glu Glu Arg Val Leu Ala Lys Thr Glu Ala Ile Tyr Asp Met Val
305                 310                 315                 320

Leu Asp Ile Phe His Arg Ala Lys Asn Glu Asn Ile Thr Thr Cys Glu
                325                 330                 335

Ala Ala Asp Arg Ile Val Met Glu Arg Leu Lys Lys Leu Thr Asp Ile
                340                 345                 350

Arg Arg Ile Leu Glu Asp Pro Arg Asn Ser Ala Arg Arg
                355                 360                 365

<210> SEQ ID NO 20
<211> LENGTH: 721
<212> TYPE: PRT
<213> ORGANISM: Solanum lycopersicum

<400> SEQUENCE: 20

Met Ala Ser Ser Ile Val Gln Asn Gly His Val Asn Gly Glu Ala Met
 1               5                  10                  15

Asp Leu Cys Lys Lys Ser Ile Asn Val Asn Asp Pro Leu Asn Trp Glu
                20                  25                  30

Met Ala Ala Glu Ser Leu Arg Gly Ser His Leu Asp Glu Val Lys Lys

```
                35                  40                  45
Met Val Asp Glu Phe Arg Lys Pro Ile Val Lys Leu Gly Glu Thr
 50                  55                  60

Leu Thr Val Ala Gln Val Ala Ser Ile Ala Asn Val Asp Asn Lys Ser
 65                  70                  75                  80

Asn Gly Val Lys Val Glu Leu Ser Glu Ser Ala Arg Ala Gly Val Lys
                 85                  90                  95

Ala Ser Ser Asp Trp Val Met Asp Ser Met Gly Lys Gly Thr Asp Ser
                100                 105                 110

Tyr Gly Val Thr Thr Gly Phe Gly Ala Thr Ser His Arg Arg Thr Lys
            115                 120                 125

Asn Gly Gly Ala Leu Gln Lys Glu Leu Ile Arg Phe Leu Asn Ala Gly
        130                 135                 140

Val Phe Gly Asn Gly Thr Glu Ser Ser His Thr Leu Pro His Ser Ala
145                 150                 155                 160

Thr Arg Ala Ala Met Leu Val Arg Ile Asn Thr Leu Leu Gln Gly Tyr
                165                 170                 175

Ser Gly Ile Arg Phe Glu Ile Leu Glu Ala Ile Thr Lys Leu Ile Asn
            180                 185                 190

Ser Asn Ile Thr Pro Cys Leu Pro Leu Arg Gly Thr Ile Thr Ala Ser
        195                 200                 205

Gly Asp Leu Val Pro Leu Ser Tyr Ile Ala Gly Leu Leu Thr Gly Arg
210                 215                 220

Pro Asn Ser Lys Ala Val Gly Pro Asn Gly Glu Lys Leu Asn Ala Glu
225                 230                 235                 240

Glu Ala Phe Arg Val Ala Gly Val Thr Ser Gly Phe Phe Glu Leu Gln
                245                 250                 255

Pro Lys Glu Gly Leu Ala Leu Val Asn Gly Thr Ala Val Gly Ser Gly
            260                 265                 270

Met Ala Ser Met Val Leu Phe Glu Ser Asn Ile Leu Ala Val Met Ser
        275                 280                 285

Glu Val Leu Ser Ala Ile Phe Ala Glu Val Met Asn Gly Lys Pro Glu
290                 295                 300

Phe Thr Asp Tyr Leu Thr His Lys Leu Lys His His Pro Gly Gln Ile
305                 310                 315                 320

Glu Ala Ala Ala Ile Met Glu His Ile Leu Asp Gly Ser Ser Tyr Val
                325                 330                 335

Lys Ala Ala Gln Lys Leu His Glu Met Asp Pro Leu Gln Lys Pro Lys
            340                 345                 350

Gln Asp Arg Tyr Ala Leu Arg Thr Ser Pro Gln Trp Leu Gly Pro Gln
        355                 360                 365

Ile Glu Val Ile Arg Ala Ala Thr Lys Met Ile Glu Arg Glu Ile Asn
            370                 375                 380

Ser Val Asn Asp Asn Pro Leu Ile Asp Val Ser Arg Asn Lys Ala Leu
385                 390                 395                 400

His Gly Gly Asn Phe Gln Gly Thr Pro Ile Gly Val Ser Met Asp Asn
                405                 410                 415

Thr Arg Leu Ala Leu Ala Ser Ile Gly Lys Leu Met Phe Ala Gln Phe
            420                 425                 430

Ser Glu Leu Val Asn Asp Tyr Tyr Asn Asn Gly Leu Pro Ser Asn Leu
        435                 440                 445

Thr Ala Gly Arg Asn Pro Ser Leu Asp Tyr Gly Leu Lys Gly Ala Glu
    450                 455                 460
```

```
Ile Ala Met Ala Ser Tyr Cys Ser Glu Leu Gln Phe Leu Ala Asn Pro
465                 470                 475                 480

Val Thr Asn His Val Gln Ser Ala Glu Gln His Asn Gln Asp Val Asn
            485                 490                 495

Ser Leu Gly Leu Ile Ser Ala Arg Lys Thr Ala Glu Ala Val Asp Ile
        500                 505                 510

Leu Lys Leu Met Ser Ser Thr Tyr Leu Val Ala Leu Cys Gln Ala Ile
            515                 520                 525

Asp Leu Arg His Leu Glu Glu Asn Leu Arg Ser Ala Val Lys Asn Thr
    530                 535                 540

Val Ser Gln Val Ala Lys Arg Thr Leu Thr Met Gly Ala Asn Gly Glu
545                 550                 555                 560

Leu His Pro Ala Arg Phe Cys Glu Lys Glu Leu Leu Arg Val Val Asp
                565                 570                 575

Arg Glu Tyr Val Phe Ala Tyr Ala Asp Asp Pro Cys Ser Ser Thr Tyr
            580                 585                 590

Pro Leu Met Gln Lys Leu Arg Gln Val Leu Val Asp His Ala Met Lys
        595                 600                 605

Asn Gly Glu Ser Glu Lys Asn Val Asn Ser Ser Ile Phe Gln Lys Ile
    610                 615                 620

Val Ala Phe Glu Asp Glu Leu Lys Ala Val Leu Pro Lys Glu Val Glu
625                 630                 635                 640

Ser Ala Arg Ala Val Val Glu Ser Gly Asn Pro Ala Ile Pro Asn Arg
                645                 650                 655

Ile Thr Glu Cys Arg Ser Tyr Pro Leu Tyr Arg Leu Val Arg Gln Glu
            660                 665                 670

Leu Gly Ser Glu Leu Leu Thr Gly Glu Lys Val Arg Ser Pro Gly Glu
        675                 680                 685

Glu Ile Asp Lys Val Phe Thr Ala Met Cys Asn Gly Gln Ile Ile Asp
    690                 695                 700

Pro Leu Leu Glu Cys Leu Lys Ser Trp Asn Gly Ala Pro Leu Pro Ile
705                 710                 715                 720

Cys

<210> SEQ ID NO 21
<211> LENGTH: 1101
<212> TYPE: DNA
<213> ORGANISM: Thermoactinomyces intermedius

<400> SEQUENCE: 21
atgcgcgacg tgtttgaaat gatggaccgc tatggccacg agcaggtcat tttttgccgt      60
catccgcaaa ccgtctcaa agcgatcatc gccttgcata atacaaccgc ggggccggct     120
ttgggtggat gccgcatgat cccgtatgct tcgacggacg aagccttgga ggatgttttg     180
cggttgtcca aggcatgac ctataaatgc agtctggcgg atgtggactt ggcgggggga     240
aaaatggtta tcatcggcga tccgaaaaaa gataaatcgc cggagttgtt tcgcgtgatc     300
ggccgttttg tgggcgggtt aaacggccgt ttctataccg aaccgacat gggaaccaat     360
ccggaagatt ttgtccatgc cgccagggaa tcgaaatctt ttgccggatt gccgaaatcg     420
tacggcggaa aggggacac atccattccc accgcgctcg gggtgtttca cggaatgcgg     480
gccaccgccc ggtttttatg ggggacggat cagctgaaag gcgtgtggt tgccatccaa     540
ggagtcggca aggtgggaga cgcttgttg cagctttgg tcgaagtggg ggcttactgc     600
```

-continued

```
aaaattgccg acatcgattc ggtgcgatgc gaacagctga agaaaagta tggcgacaag    660 gtccaattgg tggatgtgaa ccggattcac aaggagagtt gcgatatttt ctcgccttgc    720
gccaaaggcg gcgtggtcaa tgatgacacc attgacgagt tccgttgcct ggccattgtc    780
ggatccgcca acaaccaact ggtggaagac cggcatgggg cactgcttca aaaacggagc    840
atttgttatg cacccgatta tctggtgaat gccggcgggc tgattcaagt ggctgatgaa    900
ctggaaggct tccatgaaga gagtgctc gccaaaaccg aagcgattta tgacatggtc      960 ctggatatt ttcaccgggc gaaaaatgag aatattacca cttgtgaggc agcggaccgg    1020
atcgtgatgg agcgtttgaa aaagttaacc gatattcgcc ggatcttgtt ggaggatccc    1080
cgcaacagcg caaggaggta a                                              1101
```

<210> SEQ ID NO 22
<211> LENGTH: 352
<212> TYPE: PRT
<213> ORGANISM: Caenorhabditis remanei

<400> SEQUENCE: 22

```
Met Asp Phe Lys Ala Lys Leu Leu Ala Glu Met Ala Lys Lys Arg Lys
1               5                   10                  15

Ala Val Ser Gly Leu Glu Val Lys Glu Gly Ala Lys Phe Val Arg
            20                  25                  30

Gly Ala Asp Leu Glu Ser Lys Arg Thr Gln Glu Tyr Glu Ala Lys Gln
        35                  40                  45

Glu Glu Leu Ala Ile Lys Lys Arg Lys Ala Asp Asp Glu Ile Leu Gln
    50                  55                  60

Glu Ser Thr Ser Arg Ala Lys Ile Val Pro Glu Val Pro Glu Ala Glu
65                  70                  75                  80

Phe Asp Glu Lys Thr Pro Met Pro Glu Ile His Ala Arg Leu Arg Gln
                85                  90                  95

Arg Gly Gln Pro Ile Leu Leu Phe Gly Glu Ser Glu Leu Ser Val Arg
            100                 105                 110

Lys Arg Leu His Gln Leu Glu Ile Glu Gln Pro Glu Leu Asn Glu Gly
        115                 120                 125

Trp Glu Asn Glu Met Gln Thr Ala Met Lys Phe Ile Gly Lys Glu Met
    130                 135                 140

Asp Lys Ala Val Val Glu Gly Thr Ala Asp Ser Ala Thr Arg His Asp
145                 150                 155                 160

Ile Ala Leu Pro Gln Gly Tyr Glu Glu Asp Asn Trp Lys Ser Ile Glu
                165                 170                 175

His Ala Ser Thr Leu Leu Gly Val Gly Asp Glu Met Lys Arg Asp Cys
            180                 185                 190

Asp Ile Ile Leu Ser Ile Cys Arg Tyr Ile Leu Ala Arg Trp Ala Arg
        195                 200                 205

Asp Leu Asn Asp Arg Pro Leu Asp Val Lys Lys Thr Ala Gln Gly Met
    210                 215                 220

His Glu Ala Ala His His Lys Gln Thr Thr Met His Leu Lys Ser Leu
225                 230                 235                 240

Met Thr Ser Met Glu Lys Tyr Asn Val Asn Asn Asp Ile Arg His His
                245                 250                 255

Leu Ala Lys Ile Cys Arg Leu Leu Val Ile Glu Arg Asn Tyr Leu Glu
            260                 265                 270

Ala Asn Asn Ala Tyr Met Glu Met Ala Ile Gly Asn Ala Pro Trp Pro
        275                 280                 285
```

```
Val Gly Val Thr Arg Ser Gly Ile His Gln Arg Pro Gly Ser Ala Lys
        290                 295                 300

Ala Tyr Val Ser Asn Ile Ala His Val Leu Asn Asp Glu Thr Gln Arg
305                 310                 315                 320

Lys Tyr Ile Gln Ala Phe Lys Arg Leu Met Thr Lys Leu Gln Glu Tyr
                325                 330                 335

Phe Pro Thr Asp Pro Ser Lys Ser Val Glu Phe Val Lys Lys Ser Val
                340                 345                 350

<210> SEQ ID NO 23
<211> LENGTH: 411
<212> TYPE: PRT
<213> ORGANISM: Arabidopsis thaliana

<400> SEQUENCE: 23

Met Asn Ala Leu Ala Ala Thr Asn Arg Asn Phe Lys Leu Ala Ala Arg
1               5                   10                  15

Leu Leu Gly Leu Asp Ser Lys Leu Glu Lys Ser Leu Leu Ile Pro Phe
                20                  25                  30

Arg Glu Ile Lys Val Glu Cys Thr Ile Pro Lys Asp Asp Gly Thr Leu
            35                  40                  45

Ala Ser Phe Val Gly Phe Arg Val Gln His Asp Asn Ala Arg Gly Pro
50                  55                  60

Met Lys Gly Gly Ile Arg Tyr His Pro Glu Val Asp Pro Asp Glu Val
65                  70                  75                  80

Asn Ala Leu Ala Gln Leu Met Thr Trp Lys Thr Ala Val Ala Lys Ile
                85                  90                  95

Pro Tyr Gly Gly Ala Lys Gly Gly Ile Gly Cys Asp Pro Ser Lys Leu
            100                 105                 110

Ser Ile Ser Glu Leu Glu Arg Leu Thr Arg Val Phe Thr Gln Lys Ile
            115                 120                 125

His Asp Leu Ile Gly Ile His Thr Asp Val Pro Ala Pro Asp Met Gly
        130                 135                 140

Thr Gly Pro Gln Thr Met Ala Trp Ile Leu Asp Glu Tyr Ser Lys Phe
145                 150                 155                 160

His Gly Tyr Ser Pro Ala Val Val Thr Gly Lys Pro Ile Asp Leu Gly
                165                 170                 175

Gly Ser Leu Gly Arg Asp Ala Ala Thr Gly Arg Gly Val Met Phe Gly
            180                 185                 190

Thr Glu Ala Leu Leu Asn Glu His Gly Lys Thr Ile Ser Gly Gln Arg
        195                 200                 205

Phe Val Ile Gln Gly Phe Gly Asn Val Gly Ser Trp Ala Ala Lys Leu
    210                 215                 220

Ile Ser Glu Lys Gly Gly Lys Ile Val Ala Val Ser Asp Ile Thr Gly
225                 230                 235                 240

Ala Ile Lys Asn Lys Asp Gly Ile Asp Ile Pro Ala Leu Leu Lys His
                245                 250                 255

Thr Lys Glu His Arg Gly Val Lys Gly Phe Asp Gly Ala Asp Pro Ile
            260                 265                 270

Asp Pro Asn Ser Ile Leu Val Glu Asp Cys Asp Ile Leu Val Pro Ala
        275                 280                 285

Ala Leu Gly Gly Val Ile Asn Arg Glu Asn Ala Asn Glu Ile Lys Ala
    290                 295                 300

Lys Phe Ile Ile Glu Ala Ala Asn His Pro Thr Asp Pro Asp Ala Asp
```

```
          305                 310                 315                 320
Glu Ile Leu Ser Lys Lys Gly Val Val Ile Leu Pro Asp Ile Tyr Ala
                    325                 330                 335

Asn Ser Gly Gly Val Thr Val Ser Tyr Phe Glu Trp Val Gln Asn Ile
                340                 345                 350

Gln Gly Phe Met Trp Glu Glu Lys Val Asn Asp Glu Leu Lys Thr
                355                 360                 365

Tyr Met Thr Arg Ser Phe Lys Asp Leu Lys Glu Met Cys Lys Thr His
    370                 375                 380

Ser Cys Asp Leu Arg Met Gly Ala Phe Thr Leu Gly Val Asn Arg Val
385                 390                 395                 400

Ala Gln Ala Thr Ile Leu Arg Gly Trp Gly Ala
                    405                 410

<210> SEQ ID NO 24
<211> LENGTH: 378
<212> TYPE: PRT
<213> ORGANISM: Spirochaeta africana

<400> SEQUENCE: 24

Met Asn Thr Val Thr Asn Gln Trp Lys Ala Val Asp Ile Phe Thr Gln
1               5                   10                  15

Ile Arg Asp His Glu Gln Val Val Phe Cys Asn Asp Lys Asn Thr Gly
                20                  25                  30

Leu Lys Ala Ile Ile Ala Ile His Asp Thr Thr Leu Gly Pro Ala Leu
            35                  40                  45

Gly Gly Cys Arg Met Tyr Pro Tyr Ala Thr Val Glu Asp Ala Leu Phe
        50                  55                  60

Asp Val Leu Arg Leu Ser Lys Gly Met Thr Tyr Lys Cys Leu Ala Ala
65                  70                  75                  80

Asp Val Asp Phe Gly Gly Gly Lys Ala Val Ile Ile Gly Asp Pro His
                    85                  90                  95

Lys Asp Lys Thr Pro Glu Leu Phe Arg Ala Phe Gly Gln Phe Val Glu
                100                 105                 110

Ser Leu Asn Gly Arg Phe Tyr Thr Gly Thr Asp Met Gly Thr Thr Pro
            115                 120                 125

Asp Asp Phe Val His Ala Met Lys Glu Thr Asn Cys Ile Val Gly Val
        130                 135                 140

Pro Glu Glu Tyr Gly Gly Ser Gly Asp Ser Ser Val Pro Thr Ala Leu
145                 150                 155                 160

Gly Val Ile Tyr Gly Ile Gln Ala Thr Asn Lys Val Ile Trp Gly Ser
                165                 170                 175

Asp Glu Leu His Gly Lys Thr Tyr Ala Ile Gln Gly Leu Gly Lys Val
            180                 185                 190

Gly Arg Lys Val Ala Glu Arg Leu Leu Lys Glu Gly Ala Asp Leu Tyr
        195                 200                 205

Val Cys Asp Ile His Pro Thr Ala Ile Glu Ala Ile Val Ser Tyr Ala
    210                 215                 220

Lys Lys Leu Gly Ala Asn Val Lys Val Gln Gly Thr Glu Ile Tyr
225                 230                 235                 240

Arg Thr Asp Ala Asp Ile Phe Val Pro Cys Ala Phe Gly Asn Val Val
                245                 250                 255

Asn Asp Asn Thr Ile His Val Leu Lys Val Lys Ala Ile Val Gly Ser
            260                 265                 270
```

-continued

```
Ala Asn Asn Gln Leu Leu Asp Val Arg His Gly Gln Leu Leu Lys Glu
    275                 280                 285

Lys Gly Ile Leu Tyr Ala Pro Asp Tyr Ile Val Asn Ala Gly Gly Leu
    290                 295                 300

Ile Gln Val Ala Asp Glu Leu Tyr Gly Leu Asn Lys Glu Arg Val Leu
305                 310                 315                 320

Gln Lys Thr Lys Ala Ile Tyr Ser Thr Leu Leu His Ile Tyr Ser Arg
                325                 330                 335

Ala Glu Ala Asp His Ile Thr Thr Ile Glu Ala Ala Asn Arg Phe Cys
            340                 345                 350

Glu Glu Arg Leu Gln Gln Arg Ser Arg Arg Asn Asp Phe Phe Thr His
        355                 360                 365

Arg Lys Gln Pro Lys Trp Asp Ile Arg Arg
    370                 375
```

US 10,591,495 B2

DEVICE AND METHODS OF USING DEVICE FOR DETECTION OF HYPERAMMONEMIA

CROSS-REFERENCE TO RELATED APPLICATIONS

This application is a U.S. National Stage entry under 35 U.S.C. § 371, of International Application No. PCT/US2016/029623, filed on Apr. 27, 2016, which claims priority to U.S. Provisional Ser. No. 62/153,409, filed on Apr. 27, 2015, each of which is herein incorporated by reference in its entirety.

GOVERNMENT SUPPORT

This disclosure was made jointly by the NIH and with government support under HHSN268201200360P awarded by the NIH. The United States government has certain rights in the disclosure.

FIELD OF THE DISCLOSURE

The disclosure relates generally to devices that quantify and identify the presence or absence of ammonia or ammonium ion in a sample of bodily fluid, water, or other environmental sample. In some embodiments, the disclosure relates to diagnosing a subject with an hyperammonemia by detecting the presence, absence, or quantity of ammonia or ammonium ion in a sample of bodily fluid. In some embodiments, the device is a bio sensor only requiring a sample of whole bodily fluid for detection and/or quantification of ammonia or ammonium ion.

BACKGROUND OF THE DISCLOSURE

Elevated ammonia levels, oftentimes called hyperammonemia, is a potentially fatal symptom associated with a variety of diseases such as cirrhosis of the liver and urea cycle disorders found in neonatal infants. Left untreated, hyperammonemia can lead to cognitive developmental issues, seizures, other neurological problems, and death. The current testing methods include fluorometry and tandem mass spectroscopy performed by central laboratories, which could take multiple days to produce a reliable diagnosis. These methods involve large, cumbersome, and expensive machinery, which prevents testing of ammonia levels at the bedside or home once the disorder has been identified. Therefore, a system for a point of care testing device may be desired, as this may allow administration of treatment to occur more rapidly, in turn improving the neurological development of infants as well as making cirrhosis more manageable. Devices able to test for hyperammonemia may also be modified inexpensively to detect amino acid levels for applications in diagnosing and treating aminoacidopathies and other diseases.

SUMMARY OF DISCLOSURE

The present disclosure encompasses the recognition that hyperammonemia can be identified and/or characterized by identifying the levels or quantities of ammonia or ammonium ion in any sample, including a bodily fluid and, in some embodiments, including human and non-human whole blood samples. In some embodiments, the present disclosure relates to identifying the quantity, presence, or absence of ammonia or ammonium ion in bodily fluids by contacting a bodily fluid to a device disclosed herein. In some embodiments, the methods disclosed herein do not comprise contacting the bodily fluid with any reagent or external stimuli prior to identifying or quantifying whether or how much one or more ammonia or ammonium ion are present in the bodily fluid.

The present disclosure relates to a biosensor comprising: at least a first and second vessel; a fluid exchange opening positioned between the first and the second vessel; a membrane positioned across or over the fluid exchange opening; and a catalyst in solid phase within the second vessel or within a conduit in fluid communication with the second vessel; wherein the membrane comprises an ionomer.

The present disclosure also relates to a biosensor comprising: at least a first and second vessel; a fluid exchange opening positioned between the first and the second vessel; a membrane positioned across or over the fluid exchange opening; and a phenolic reagent stored in solid phase within the second vessel or within a conduit in fluid communication with the second vessel; wherein the membrane comprises an ionomer.

The present disclosure also relates to a biosensor comprising: at least a first and second vessel configured for receiving a volume of a sample from a point exterior to the biosensor; a fluid exchange opening positioned between the first and the second vessel; a membrane positioned across or over the fluid exchange opening; and a catalyst in liquid phase or solid phase a hypohalite in liquid phase; an alkali buffer in liquid phase; a phenolic reagent in liquid phase or solid phase; and a fluid circuit comprising, in fluid communication: the first and second vessel; a reagent conduit; and a detection vessel positioned distal from the first and second vessel; wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than about 7 μm.

The present disclosure also relates to a system comprising the biosensor disclosed herein in operable connection to at least one computer storage memory. In some embodiments, the system comprises at least a first and second vessel configured for receiving a volume of a sample from a point exterior to the biosensor; a fluid exchange opening positioned between the first and the second vessel; a membrane positioned across or over the fluid exchange opening; and a catalyst in liquid phase or solid phase a hypohalite in liquid phase; an alkali buffer in liquid phase; a phenolic reagent in liquid phase or solid phase; and a fluid circuit comprising, in fluid communication: the first and second vessel; a reagent conduit; and a detection vessel positioned distal from the first and second vessel; wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than about 7 μM; in operable connection to at least one computer storage memory. In some embodiments, the system comprises a computer processor in operable connection with the at least one: light emitting diode (LED), amplification circuit, battery, or stepper motor. In some embodiments, the system comprises a digital display in operable connection to at least one electrically conductive support by an electrical circuit capable of carrying an a electrical signal corresponding to a measurement of a wavelength, current, and/or voltage differential from a diode, spectrophotometer, voltmeter and/or amperoeter to the digital display, wherein the digital display is a configured to display concentration value of ammonia, ammonium ion and/or an amino acid in a sample when the at least one electrically conductive support is in contact with the sample for a time period sufficient for the at least one catalyst to catalyze the indophenol reaction. In some embodiments, the system comprises a solid support, such as a test strip or a chip or cartridge comprising a fluid circuit comprising: a reaction vessel in fluid communication with a reagent conduit and a detection vessel. Each reagent disclosed herein may be added to the sample at the reaction vessel, mixing takes place in the reagent conduit and detection occurs at the detection vessel. The chipr, cartridge or test strip may be inserted into a handheld device or tabletop device comprising diode, spectrophotometer, voltmeter and/or amperometer and a digital display such that, when the test strip, cartridge or chip is contacted to the device, the first and second electrodes become operably connected to a closed electrical circuit comprising the voltmeter and/or amperometer and the digital display, and, upon contact with a sample, hypohalite, an alkali buffer, catalyst and at least one indophenol reagent or indophenol related compound catalyze an indophenol reaction resulting in a current on the first electrode corresponding to a concentration value of ammonia in the sample, such concentration value readable on the display of the device. In some embodiments, the reaction vessel is in fluid communication with a conduit configured to receive a sample from a point exterior to the test strip, cartridge, chip or device. In some embodiments, the reaction vessel is bifurcated laterally or vertically by a membrane comprising or consisting of an ionomer, such that the reaction vessel is split into a first and second vessel.

The present disclosure also relates to a kit comprising a biosensor or test strip comprising: at least a first and second vessel; a fluid exchange opening positioned between the first and the second vessel; at least one conduit in fluid communication with the at least first vessel, the at least one conduit configured to receive a fluid from a point external to the biosensor; and a membrane positioned at the fluid exchange opening; a catalyst in liquid phase or solid phase a hypohalite in liquid phase; an alkali buffer in liquid phase; a phenolic reagent in liquid phase or solid phase; and a fluid circuit comprising, in fluid communication: the first and second vessel; a reagent conduit; and a detection vessel positioned distal from the first and second vessel; wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than about 7 µM; and wherein the membrane comprises an ionomer.

The present disclosure also relates to a kit comprising a solid support that comprises: at least a first and second vessel; a fluid exchange opening positioned between the first and the second vessel; at least one conduit in fluid communication with the at least first vessel, the at least one conduit configured to receive a fluid from a point external to the biosensor; and a membrane positioned at the fluid exchange opening; a catalyst in liquid phase or solid phase; a hypohalite in liquid phase; an alkali buffer in liquid phase; a phenolic reagent in liquid phase or solid phase; and a fluid circuit comprising, in fluid communication: the first and second vessel; a reagent conduit; and a detection vessel positioned distal from the first and second vessel; wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than about 7 µM; and wherein the membrane comprises an ionomer.

The present disclosure also relates to a method of determining or identifying a concentration of an ammonia or ammonium ion in a sample comprising: contacting a sample to any biosensor disclosed herein, or any system disclosed herein; or any test strip disclosed herein; and determining a quantity of ammonia or ammonium ion in the sample.

The present disclosure also relates to a method of quantifying a concentration of ammonia or ammonium ion in a comprising contacting a sample of bodily fluid to any biosensor disclosed herein, or any system disclosed herein; or any test strip disclosed herein.

The present disclosure also relates to a method of diagnosing a metabolic disease in a subject comprising: (a) contacting a sample of bodily fluid to the to any biosensor disclosed herein, or any system disclosed herein; or any test strip disclosed herein; (b) quantifying one or more concentration values of ammonia in the sample; (c) comparing the one or more concentration values of ammonia in the sample to a threshold value of ammonia concentration identified as being in a healthy range; and (d) identifying the subject as having a metabolic disease if the one or more concentration values of ammonia in the sample exceed or fall below the threshold value.

The present disclosure also relates to a method of determining patient responsiveness to a therapy comprising: (a) contacting a sample of bodily fluid to any biosensor disclosed herein, or any system disclosed herein; or any test strip disclosed herein; (b) quantifying one or more ammonia or ammonium ion concentration values; (c) comparing the one or more concentration values to one or more threshold values associated with a metabolic disease.

The present disclosure also relates to a test strip comprising a solid support comprising: at least a first and second vessel configured for receiving a sample from a point exterior to the biosensor; a fluid exchange opening positioned between the first and the second vessel; a membrane positioned across or over the fluid exchange opening; and a catalyst in liquid phase or solid phase; a hypohalite in liquid phase; an alkali buffer in liquid phase; a phenolic reagent in liquid phase or solid phase; and a fluid circuit comprising, in fluid communication: the first and second vessel; a reagent conduit; and a detection vessel positioned distal from the first and second vessel; wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than about 7 µM; and wherein the membrane comprises an ionomer.

The present disclosure also relates to a method of manufacturing any biosensor disclosed herein, or any system disclosed herein; or any test strip disclosed herein comprising affixing the membrane between the first and/or second vessel.

The present disclosure also relates to a method of detecting the presence, absence, or quantity of amino acid in a sample comprising: (a) contacting a sample of bodily fluid to any biosensor disclosed herein, or any system disclosed herein; or any test strip disclosed herein; or any cartridge disclosed herein; (b) quantifying one or more ammonia or ammonium ion concentration values; (c) correlating the one or more ammonia or ammonium ion concentration values to one or more quantities of an amino acid.

The present disclosure also relates to a method of treating a metabolic disease comprising: (a) contacting a sample of bodily fluid to the to any biosensor disclosed herein, or any system disclosed herein; or any test strip disclosed herein; (b) quantifying one or more concentration values of ammonia in the sample; (c) comparing the one or more concentration values of ammonia in the sample to a threshold value of ammonia concentration identified as being in a healthy range; and (d) identifying the subject as having a metabolic disease if the one or more concentration values of ammonia in the sample exceed or fall below the threshold value; (e) administering a therapeutically effective amount of a therapeutic agent to treat metabolic disease.

The disclosure relates to a method of detecting or quantifying ammonia in a blood sample from a subject comprising: wiping a portion of the subject from which the blood will be drawn with saline solution; inserting a sharp device into the portion of the body from which blood will be drawn at a an angle and depth in the skin sufficient to draw at least a droplet of blood from the point of insertion; contacting at least a droplet of blood from the surface of the body to a sensor surface. In some embodiments, the method of detecting or quantifying ammonia in a blood sample from a subject is free of wiping the portion of the subject from which the blood will be drawn with a pad, swab or solution comprising iodine or alcohol. In some embodiments, wiping a portion of the body from which the blood will be drawn with a swab, wipe, or solution comprising saline but free of iodine, detergent or alcohol.

BRIEF DESCRIPTION OF THE DRAWINGS

Advantages of embodiments of the present invention will be apparent from the following detailed description of the exemplary embodiments. The following detailed description should be considered in conjunction with the accompanying figures in which:

FIG. 5A depicts a diagram of the cartridge, comprising three blister packs. FIG. 5B depicts a sample cartridge reader.

DETAILED DESCRIPTION OF THE DISCLOSURE

Figure 1:
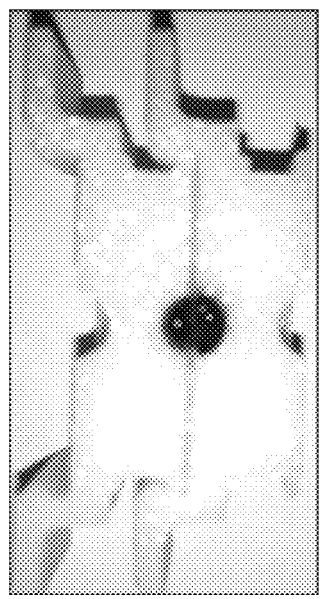
FIG. 1 depicts a photograph of 3D printed modular pieces snapped together around Nafion to form the bisected well.

Various terms relating to the methods and other aspects of the present disclosure are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the terms "attach," "attachment," "adhere," "adhered," "adherent," or like terms generally refer to immobilizing or fixing, for example, a group, a compound or enzyme, to a surface, such as by physical absorption, chemical bonding, and like processes, or combinations thereof.

As used herein, the terms "biopsy" means a cell sample, collection of cells, or bodily fluid removed from a subject or patient for analysis. In some embodiments, the biopsy is a bone marrow biopsy, punch biopsy, endoscopic biopsy, needle biopsy, shave biopsy, incisional biopsy, excisional biopsy, or surgical resection. In any of the methods disclosed herein, the method may comprise a step of isolating a section of tissue by any biopsy technique described above and grinding the tissue or extracting blood from the tissue to create fluid sample.

As used herein, the terms "bodily fluid" means any fluid from a isolated from a subject including, but not necessarily limited to, blood sample, serum sample, a whole blood sample, urine sample, mucus sample, saliva sample, and sweat sample. The sample may be obtained from a subject by any means such as intravenous puncture, biopsy, swab, capillary draw, lancet, needle aspiration, collection by simple capture of excreted fluid.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation. In addition, those skilled in the art may appreciate the wide variations in sizing scales that may be incorporated into the disclosed or related designs for use with samples many orders of magnitude larger or smaller than those disclosed.

As used herein, the term "aminoacidopathy" is meant to refer to those diseases and disorders characterized by dysfunction of a metabolic catalysis of amino acids that results in over production or under production of amino acids in the body of a subject. Examples of aminoaciopathies are listed in the definition of a metabolic disease, terms that are used interchangeably in this application.

As used herein the terms "electronic medium" mean any physical storage employing electronic technology for access, including a hard disk, ROM, EEPROM, RAM, flash memory, nonvolatile memory, or any substantially and functionally equivalent medium. In some embodiments, the software storage may be co-located with the processor implementing an embodiment of the disclosure, or at least a portion of the software storage may be remotely located but accessible when needed.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). To use the term "homologus to" is synonymous with a measured "sequence identity." In some embodiments, if an embodiment comprises a nucleic acid sequence or amino acid sequence with a percent sequence identity the term refers to a disclosed nucleic acid sequence or amino acid sequence possessing a homology to a disclosed sequence over its entire length.

The term "subject" is used throughout the specification to describe an animal from which a sample of bodily fluid is taken. In some embodiment, the animal is a human. For diagnosis of those conditions which are specific for a specific subject, such as a human being, the term "patient" may be interchangeably used. In some instances in the description of the present disclosure, the term "patient" will refer to human patients suffering from a particular disease or disorder. In some embodiments, the subject may be a human suspected of having or being identified as at risk to develop a metabolic disease, such as hyperammonemia. In some embodiments, the subject may be diagnosed as having at least one aminoacidopathy. In some embodiments, the subject is suspected of having or has been diagnosed with hyperammonemia. In some embodiments, the subject may be a human suspected of having or being identified as at risk to develop hyperammonemia. In some embodiments, the subject may be a mammal which functions as a source of the isolated sample of bodily fluid. In some embodiments, the subject may be a non-human animal from which a sample of bodily fluid is isolated or provided. The term "mammal" encompasses both humans and non-humans and includes but is not limited to humans, non-human primates, canines, felines, murines, bovines, equines, and porcines. Any methods disclosed herein may comprise testing a blood sample from a mammal, human, non-human, or any other non-human animal disclosed herein.

As used herein, "conservative" amino acid substitutions may be defined as set out in Tables A, B, or C below. Metabolic enzymes include those amino acid sequences wherein conservative substitutions have been introduced by modification of polynucleotides encoding polypeptides disclosed herein. Amino acids can be classified according to physical properties and contribution to secondary and tertiary protein structure. A conservative substitution, which may be a part of any amino acid disclosed herein, is recognized in the art as a substitution of one amino acid for another amino acid that has similar properties. Exemplary conservative substitutions are set out in Table A.

TABLE A

Conservative Substitutions I

| Side Chain Characteristics | Amino Acid |
|---|---|
| Aliphatic | |
| Non-polar | G A P I L V F |
| Polar-uncharged | C S T M N Q |
| Polar-charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | Amino Acid |
|---|---|
| Non-polar (hydrophobic) | |
| Aliphatic: | A L I V P |
| Aromatic: | F W Y |
| Sulfur-containing: | M |
| Borderline: | G Y |
| Uncharged-polar | |
| Hydroxyl: | S T Y |
| Amides: | N Q |
| Sulfhydryl: | C |
| Borderline: | G Y |

TABLE B-continued

Conservative Substitutions II

| Side Chain Characteristic | Amino Acid |
|---|---|
| Positively Charged (Basic): | K R H |
| Negatively Charged (Acidic): | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides comprising polypeptide sequences associated with the extracellular matrix described herein are intended to include polypeptides bearing one or more insertions, deletions, or substitutions, or any combination thereof, of amino acid residues as well as modifications other than insertions, deletions, or substitutions of amino acid residues.

As used herein, the term "prognosing" means determining the probable course and/or outcome of a disease.

As used herein, the terms "indophenol related compound" mean a small chemical compound that is a reaction product of an indophenol reaction. In some embodiment, it comprises at least one carbon atom in a 4, 5, 6-membered ring and emits a visible wavelength of light upon excitation of the small chemical compound by light emitted by from light source. In some embodiments, the small chemical compound is a product of the indophenol reaction and emits a wavelength of light visible to the human eye upon excitation of the chemical compound by light emitted from a light source. In some embodiments, the small chemical compound emits a wavelength from about 400 nm to about 700 nm when it is excited by light from a light source. In some embodiments, the small chemical compound emits a wavelength of about 635 nm when it is excited by light from a light source. In some embodiments, the biosensor, device, and/or system comprises a light source and at least one diode and/or spectrophotometer, or other device capable of measuring the light emitted by the indophenol or the indophenol related compound when said indophenol or indophenol related compound is exposed to light.

The term "vessel" as used herein is any chamber, indentation, container, receptacle, or space. In some embodiments, a vessel is a well capable of holding no more than about 1,000, 900, 800, 700, 600, 500, 400, 300, 200, 100, 90, 80, 70, 60, 50, 40, 30, 20, 15, 12, 10, 9, 8, 7, 6, 5, 4, 3, 2, or 1 µL of total volume. In some embodiments, the reaction vessel comprises the first and second vessels separated by a membrane and each of the first or second vessels is no more than 100, 90, 80, 70, 60, 50, 40, 30, 20, 15, 12, 10, 9, 8, 7, 6, 5, 4, 3, 2, or 1 µL of total volume. In some embodiments, the total volume of the first and second vessels combined is no more than 100, 90, 80, 70, 60, 50, 40, 30, 20, 15, 12, 10, 9, 8, 7, 6, 5, 4, 3, 2, or 1 µL of total volume. The biosensor, chip, cartridge, test strip or solid support disclosed herein can include multiple vessels in fluid communication with each other. In some embodiments, the biosensor, chip, cartridge, test strip or solid support comprises a reaction vessel which is configured to receive a sample or portion of a sample. In some embodiments, the biosensor, chip, cartridge, test strip or solid support comprises a a detection vessel, which is configured to be near to substantially near a diode or some other disclosed device capable of stimulating the contents of the detection vessel and enabling detection of the amount of ammonia in the vessel. In some embodiments, the biosensor, chip, cartridge, test strip or solid support comprises a reagent conduit, which may be branched or unbranched, linear, curved, or not linear, that connects the reaction vessel to the detection vessel. In some embodiments, at least a portion of the reagent conduit comprises at least one, two or more components of the indophenol reaction in solid phase, such as a powder. In some embodiments, at least a portion of the reagent conduit comprises a nonlinear portion which has two or more parallel paths of fluid flow before fluid passing through the reagent conduit reaches the detection vessel. The parallel portions of fluid path enable mixing of all of the reagents and completion of a sufficient number of indophenol reaction prior to detection of the ammonia in a sample. In some embodiments, the biosensor, chip, cartridge, test strip or solid support comprises a conduit, which may be branched or unbranched, linear, curved, or not linear, that connects the reaction vessel to one, two, three, four, five or more reagent storage vessels. The reagent storage vessels may be from about 5 microliters to about 100 microliters in volume and store any of the disclosed reagents in liquid phase. In some embodiments, the reagent storage vessel is from about 5 microliters to about 50 microliters in volume. In some embodiments, the reagent storage vessel is from about 5 microliters to about 40 microliters in volume. In some embodiments, the reagent storage vessel is from about 5 microliters to about 30 microliters in volume. In some embodiments, the reagent storage vessel is from about 5 microliters to about 20 microliters in volume. In some embodiments, the reagent storage vessel is from about 5 microliters to about 10 microliters in volume.

The term "membrane" means any monomer or polymer in a solid phase. In some embodiments, the membrane comprises an ionomer. In some embodiments, the membrane is incapable of gas chromatography. In some embodiments, the membrane comprises an ionomer and is formed in the shape of a sheet which is capable of extension over or between one or more openings.

The terms "point of care" disclosed herein refer to a device, biosensor, system, test strip, or cartridge, either individually or configured to function with one or more additional components, capable of analyzing the presence, absence, or quantity of a reaction product, such as ammonia, and/or a sample component, such as an amino acid, within a time period no more than about 1, 2, 3, 4, 5, 6, 7, 8, 9, 10, 15, 20, 25, or 30 minutes. In some embodiments, the terms refer to a device, biosensor, system, chip, test strip, or cartridge, either individually or configured to function with one or more additional components, capable of analyzing the presence, absence, or quantity of ammonia and/or an amino acid within a time period no more than about 1, 2, 3, 4, 5, 6, 7, 8, 9, 10, 15, 20, 25, 30 or 40 minutes, or capable analyzing the presence, absence, or quantity of ammonia and/or an amino acid at or substantially near the point from which the sample was taken. For instance, in some embodiments, the sample may be taken from a subject suspected of or previously diagnosed with hyperammonemia or a hyperammonemia-related disorder. Without sending and analyzing the ammonia content of a sample to a different location from the source of the sample, in some embodiments, the point of care device or biosensor or system is a point of care device which is capable of detecting the presence, absence, or quantity of ammonia or ammonium ion in a sample.

The term "fluid exchange opening" means any space or void through which a fluid may pass from one vessel to an adjacent vessel or another vessel in fluid communication with the one vessel.

The terms "individually comprise" in respect to a claimed element or elements mean that only one claimed element comprises each of the listed elements and not in combination with any other element named.

The terms "a compound comprising a phenol substituent" means any molecule comprising a phenyl group attached to a 4, 5, 6, or more-membered atomic ring comprising at least one carbon atom.

The term "ionomer" as used herein refers to any polymer comprising an ion. In some embodiments, the ionomer is a perflurinated ionomer. In some embodiments, the ionomer comprises Formula I or a salt thereof.

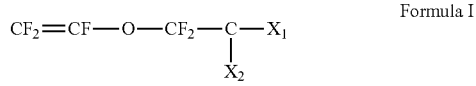

Formula I

Where $X_1$=F—O—$CF_2$—Y, $F_2$—$SO_2$, or $F_2$—$CF_2$—$CO_2CH_3$
$X_2$=$CF_3$, or, if $X_1$ is $F_2$, $X_2$ is null
Where Y=$CF_2$—$SO_2F$, $CF_2$—CF—$SO_2F$, or $CF_3$—$CO_2CH_3$
In some embodiments, the ionomer comprises one or a combination of:

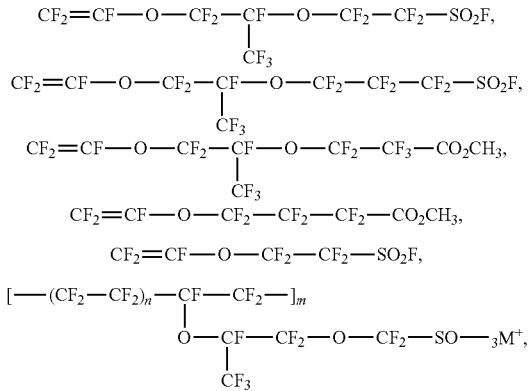

or a salt thereof, wherein n and m are any positive integer. In some embodiments, n and/or m are 1, 2, 3, 4, 5, 6, 7, 8, 9, or 10 or more. In some embodiments, n and/or m are independently variable and any positive integer from about 1 to about 1000. In some embodiments, n and/or m are independently variable and any positive integer from about 1 to about 500.

The term "bodily fluid" means any sample taken from an animal including a human, or non-human animal.

As used herein, the term "functional fragment" means any portion of a disclosed polypeptide that is of a sufficient length to retain at least partial biological function that is similar to or substantially similar to the function of the wild-type polypeptide upon which the fragment is based. In some embodiments, a functional fragment of a polypeptide associated with the function of a metabolic enzyme is a polypeptide that comprises at least 70%, 75%, 80, 85, 90, 95, 96, 97, 98, or 99% sequence identity of any polypeptides disclosed herein and has sufficient length to retain at least partial binding affinity to one or a plurality of substrates that bind to the polypeptide. In some embodiments, the fragment is a fragment of any polypeptide disclosed herein and has a length of at least about 10, about 20, about 30, about 40, about 50, about 60, about 70, about 80, about 90, or about 100 contiguous amino acids. In some embodiments, the fragment is a fragment of any polypeptide disclosed herein and has a length of at least about 50 amino acids. In some embodiments, the fragment is a fragment of any polypeptide disclosed herein and has a length of at least about 100 amino acids. In some embodiments, the fragment is a fragment of any polypeptide disclosed herein and has a length of at least about 150 amino acids. In some embodiments, the fragment is a fragment of any polypeptide disclosed herein and has a length of at least about 200 amino acids. In some embodiments, the fragment is a fragment of any polypeptide disclosed herein and has a length of at least about 250 amino acids.

As used herein, the terms "polypeptide sequence associated with the metabolic enzyme" means any polypeptide or fragment thereof, modified or unmodified by any macromolecule (such as a sugar molecule or macromolecule), that is a metabolic enzyme as disclosed herein or a functional fragment thereof. In some embodiments the polypeptide sequence is is synthetic or recombinantly produced in any multicellular or unicellular organism. In some embodiments, a polypeptide sequence associated with the extracellular matrix is any polypeptide which sequence comprises any of the polypeptides disclosed in Table 2. In some embodiments, a polypeptide sequence associated with the metabolic enzyme is any polypeptide sequence comprising any of the polypeptides disclosed in Table 2 or a sequence that shares 85, 90, 95, 96, 97, 98, or 99% sequence identity with the polypeptides disclosed in Table 2 or a functional fragment thereof. In some embodiments, a polypeptide sequence associated with the metabolic enzyme consists of any of the polypeptides disclosed in Table 2 or a sequence that shares 85, 90, 95, 96, 97, 98, or 99% sequence identity with the polypeptides disclosed in Table 2.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Salts include those formed from hydrochloric, hydrobromic, sulphuric, phosphoric, citric, tartaric, lactic, pyruvic, acetic, succinic, fumaric, maleic, methanesulphonic and benzenesulphonic acids.

In some embodiments, the device, system, membrane, or vessel, may comprise any of the disclosed reagents or formula disclosed herein or any salt. Salts may be formed by reacting the free base, or a salt, enantiomer or racemate thereof, with one or more equivalents of the appropriate acid. In some embodiments, salts of the present invention refer to salts of the disclosed reagents or formula disclosed herein having at least one basic group or at least one basic radical. In some embodiments, salts of the present invention refer to salts of the disclosed reagents or formula disclosed herein having a free amino group, a free guanidino group, a pyrazinyl radical, or a pyridyl radical that forms acid addition salts. In some embodiments, salts of the present invention refer to salts of the disclosed reagents or formula disclosed herein that are acid addition salts of the subject compounds with (for example) inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin. Salts according to the present invention may be found in their anhydrous form or as in hydrated crystalline form (i.e., complexed or crystallized with one or more molecules of water).

As used herein, the term "antibody" refers to any immunoglobulin, whether natural or wholly or partially synthetically produced. In some embodiments, an antibody is a complex comprised of 4 full-length polypeptide chains, each of which includes a variable region and a constant region, e.g., substantially of the structure of an antibody produced in nature by a B cell. In some embodiments, an antibody is a single chain. In some embodiments, an antibody is cameloid. In some embodiments, an antibody is an antibody fragment. In some embodiments, an antibody is chimeric. In some embodiments, an antibody is bi-specific. In some embodiments, an antibody is multi-specific. In some embodiments, an antibody is monoclonal. In some embodiments, an antibody is polyclonal. In some embodiments, an antibody is conjugated (i.e., antibodies conjugated or fused to other proteins, radiolabels, cytotoxins). In some embodiments, an antibody is a human antibody. In some embodiments, an antibody is a mouse antibody. In some embodiments, an antibody is a rabbit antibody. In some embodiments, an antibody is a rat antibody. In some embodiments, an antibody is a donkey antibody. In some embodiments, the biosensor or system described herein comprises an antibody or plurality of antibodies.

Characteristic: As is used herein, the term "characteristic" refers to any detectable feature of a sample of bodily fluid that allows it to be distinguished from a comparable sample of bodily fluid. In some embodiments, a characteristic is an amount or identity of ammonia or ammonium ion in bodily fluid, in an environmental sample, or water sample. In some embodiments, a characteristic is an amount, sequence of, or modification of a amino acid. In some embodiments a characteristic is an amount of a carbohydrate. In some embodiments, a characteristic is an amount of a small molecule.

Comparable: As is used herein, the term "comparable" is used to refer to two entities that are sufficiently similar to permit comparison, but differing in at least one feature.

Metabolic Enzyme: As is used herein, the term "metabolic enzyme" means an enzyme responsible for catalysis of at least one step in the metabolic pathway of one or more amino acids. In some embodiments, the metabolic enzyme is phenylalanine dehydrogenase, glutamate dehydrogenase, respective functional fragments or a combination thereof or a fusion protein thereof.

As used herein the terms "metabolic disease" is any one of a group of disorders caused by a defect in an enzymatic step in the metabolic pathway of one or more amino acids or in a protein mediator necessary for transport of certain amino acids into or out of cells. In some embodiments, the metabolic disease is chosen from: Argininemia (ARG, arginase deficiency) Argininosuccinate acidemia (ASA, argininosuccinase) Citrullinemia type I (CIT-I, argininosuccinate synthetase) Citrullinemia type II (CIT-II, citrin deficiency) Defects of biopterin cofactor biosynthesis (BIOPT-BS) Defects of biopterin cofactor regeneration (BIOPT-RG) Homocystinuria (HCY, cystathionine beta synthase) Hyperphenylalaninemia (H-PHE) Hypermethioninemia (MET) Maple syrup urine disease (MSUD, branched-chain ketoacid dehydrogenase) Phenylketonuria (PKU, phenylalanine hydroxylase) Tyrosinemia type I (TYR-1, fumarylacetoacetate hydrolase), Tyrosinemia type II (TYR-II, tyrosine aminotransferase), and Tyrosinemia type III (TYR-III, hydroxyphenylpyruvate dioxygenase) where the parenthetical phrases after each disease state represent an abbreviation for the disease accompanies by the enzyme that is generally defective in the subject suffering from the disease state. In some embodiments, the metabolic disease is a urea cycle disorder or hyperammonemia.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying or significantly reducing activity. Thus, any polypeptide that retains activity and shares at least about 30-40% overall sequence identity, often greater than about 50%, 60%, 70%, 75%, 80%, or 85%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

As used herein, the term "therapeutically effective amount" refers the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment. In some embodiments, the therapeutically effective amount comprises the amount of active compound or pharmaceutical agent that elicits the biological or medicinal response that is being sought in a tissue, system, animal, individual or human by a researcher, veterinarian, medical doctor or other clinician to treat or prevent metabolic disease, such as hyperammonemia.

As used herein, the term "threshold value" is the concentration of ammonia or ammonium ion or amino acid in a sample of bodily fluid that indicates whether the amount of ammonia or ammonium ion or amino acid in the sample is considered abnormally high or low resulting in a diagnosis or suspected diagnosis of a particular disorder, such as a metabolic disease. For instance, in the case of a blood sample, known threshold values for certain amino acidopathies are indicated in Table 1 below:

TABLE 1

Aminoacidopathies and their associated amino acid markers detectable in a sample

| Disorder | Marker | Abnormal Range |
|---|---|---|
| ARG | Arginine | >100 umol/L |
| ASA | Argininosuccinic acid | >4.0 umol/L |
|  | ASA/Arg | >0.75 |
| CIT-I and CIT-II | Citrulline | >60 umol/L |
|  | Cit/Tyr | >1.0 |
|  | Cit/Arg | >6.0 |
| HCY and MET | Methionine | >70 umol/L |
|  | Met/Phe | >1.2 |
| MSUD | Leucine | >250 umol/L |
|  | Valine | >250 umol/L |
|  | Leu/Phe | >4.0 |
|  | Val/Phe | >3.5 |
| PKU, H-PHE | Phenylalanine | >130 umol/L |
| BIOPT-BS and BIOPT-RG | Phe/Tyr | >2.0 |
| TYR-I, TYR-II, and TYR-III | Tyrosine | >250 umol/L |

In some embodiments, information about a threshold value or reference sample of bodily fluid is obtained prior to or simultaneously with information about an experimental sample of bodily fluid. In some embodiments, information about a reference cell or cell type is historical. In some embodiments, information about a threshold value or reference sample of bodily fluid is stored for example in a computer-readable storage medium. In some embodiments, comparison of a particular concentration value with a threshold value or reference sample of bodily fluid differentiates the concentration values of ammonia in an experimental sample of bodily fluid with the threshold values thereby allowing a comparison that results in diagnosing a subject with one or more metabolic diseases or a change in severity of one or more metabolic diseases.

Reference electrode: As will be understood from context, a reference electrode or control electrode is an electrically conductive support such as an electrode placed in a circuit with an at least one electrically conductive support comprising hydrogel and/or immobilized enzymes disclosed herein, to permit a relevant comparison of voltage difference between the reference or control electrode and the at least one electrically conductive support comprising hydrogel and/or immobilized enzymes disclosed herein.

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises bodily fluid. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. in some embodiments, the methods disclosed herein do not comprise a processed sample. In some embodiments, the methods disclosed herein comprise taking a sample from water or other environmental surface, processing the sample to include a known volume, and exposing the sample to the biosensor, system, or test strip disclosed herein.

As used herein "whole blood" means blood that is taken directly from the subject and unprocessed by filtration or additives prior to manipulation. in some embodiments, whole blood may comprise anti-coagulants. In some embodiments, whole blood is free of anti-coagulants.

In some embodiments, the system, test strip, device, biosensor, chip and/or cartridge comprises a concentration of any one or combination of the reagents disclosed on pages 78-84 of this disclosure.

TABLE 2

| Enzyme | Gene Sequence | Accession Numbers |
|---|---|---|
| Phenylalanine Dehydrogenase | ATGGAAATCTTCGAGGAAATCAAACGGCGGGACACGAGCAA ATTCTGTTCAATTATGATCGGGCTTCCG GTTTGAAAGCAATTATCGCCATTCACAATACTACGTTGGGGC | AEW06037.1 YP_005257709.1 AEH47572.1 |

TABLE 2-continued

| Enzyme | Gene Sequence | Accession Numbers |
|---|---|---|
| | CGGCGTTGGGCGGGTGCCGAATGTTACC<br>GTATCAAACGGAAGAGGCGGCCCTCGAGGATGCGCTGCGGTT<br>GTCGGAAGGGATGACCTATAAAGCGGCC<br>GCCGCCGGGCTCGATTTCGGCGGGGGCAAAACGGTGATTATC<br>GGGGATCCGATGAAAGACAAGTCCGAGG<br>CCCTGTTTCGTGCGCTCGGGCGTTTTATCGAGACCTTGAAAG<br>GCCGTTACCTTACGGGAGAAGACGTAGG<br>AACCAACGAAGAAGATTTGTCTGGGCTCGTCGGGAAACCCG<br>TTATGTTGTCGGATTGCCGCCGGCTTAT<br>GGCGGGTCCGGCGATACGGGTGACAATACCGCGCGCGGCGTC<br>ATTCAAGCGATGCGCGCCGCGTTGATGC<br>ACCGGTACGGTTCGCCGGATCTCCAGGGCCGGCGGATTGCCG<br>TCCAAGGGCTGGGCAAAGTAGGCTATCA<br>TGTGGCGCGACGGGCCATCGAGGCCGGCGCTCGAGTGATTGC<br>GGCCGATATCAATCCGCATGTAGTCGGC<br>CGAGTGGCGTCCGCTTGGGGGATTGAAGCCACCGATCCGTGG<br>GCTGTGGTGGAAACCCCCTGCGATATTT<br>TCGCCCCCTGTGCGTTGGGTAACGTCATTACGGAACGGACCG<br>TGTCCGCCCTCCAATGTCAGGTGGTGGC<br>CGGTTCGGCCAACAATCAGCTGGCGGATGATCGACTGGCCGA<br>TGATTTAGCTGCCCGCGGCATTCTCTAT<br>GCGCCGGATTTTATTGCGAATGCCGGCGGATTGATTCAGGTG<br>GCGGATGAAATTCGGGGATATCATGAAG<br>AACGGGTCCGTCATCAAATAGACGGGATTTATGACGTCCTGC<br>TCGAGATTTTTCGGAAGGCGGACGCCTC<br>CGGCCGATCAACCGTGGCGGTTGCGGTAGACGAGGCGCGTCG<br>CCGTTTGGACACCATTCAGGCCATCCAC<br>CGCCTGTACGGATCATAG (SEQ ID NO: 1) | YP_004587653.1<br>YP_004581770.1<br>AEH07849.1<br>ACF96938.1<br>YP_007466124.1<br>EZP75760.1<br>AGT95551.1<br>EWG09095.1<br>YP_008456272.1<br>EME23486.1<br>EJS99791.1<br>EIT85807.1<br>AAA22646.1<br>EDL64419.1<br>EAR66050.1<br>BAA08816.1 |
| Phenylalanine Ammonia-Lyase | CTGCAGGTCAACGGATCATATTCTACACATATATAATGCACTCCAATTGA<br>CATAATACATAACGTGACAT<br>ATGATACATTTATTAATATTAATTGTCACATTTACACTTCACATATTAAA<br>ATACTCTCGTATGAATGCAA<br>TTTGAAACATATTTTAAATTAATTGATTGATATATATTGAACAAAACCTA<br>ACAAAAATGCACCCTCTTGG<br>TTCACAAAGAAACTTTCTTCTATTTCTCACTTATTTCTGCTAGTGTCTTT<br>CCTATTCAAAGCCATCATTT<br>CCATCAACCTTCACAATACCATGTTTAAAAAGTCATTAAAAATCAATTTT<br>TTAAATAGAAAAAAACAAGA<br>AGATGAAATCACTTGGTTGGTACTATATATTTAGTTGTTAAGTTTGACT<br>CATACCGTGTATTGACCAAT<br>ATAAATAAAATCTTATTTCAAATAAATTCAAAAGTTCAATAAATATATAT<br>TCGTTCATAACTTATAATAA<br>AATTGATTATACATAGTCCTCCCCCATTCACTTTTACTGATCAATTATTT<br>CTAAAATATATTATTACTTT<br>TACTTGTTATTTTTAATAAATTAAGAAAATATAATACTCCCTTCGTTTTT<br>AAAAAAATACCTAGTTTGAC<br>TTGAAACGGAGTTTAATAAAAGAAAGAAGACTTGTTAATCTTGTGATTCT<br>AAATTAAAGTTATGTCAAAT<br>GTACCAAAATGTCCTTTAATCTTGTGGTCTTAAACATGTCACATGAAAAA<br>TTAAAGTGTTTCAAAAAAA<br>GAAAGGGGTCAATGTCATTCTTTTTTAAACAGACTAAAAAGAAATAAAC<br>TCATTCTTTTTGAAACGGAG<br>AGAGTAATTTTTTCCACGTTTTACTCATTAATATTAAATATTATTCTCTA<br>GATCATCCTATAAGATCTAA<br>TAGTGGACATCAATTAATACCTATGTCACTTATTATTATTTTAATAATTG<br>TATCAAGTCAAATAATAACA<br>AGTAAAAATGGAGTACCTACTATTAATCTTCAACAACCACAATTTACTAG<br>TTTTTTCCTAGCAACCCCCT<br>CTCACATATTTCACCATTTACTGGTTTTTTCCTAGCAACCCCCTCTCACA<br>TATTTTGTTTACCAACCATC<br>ATTTGTTCCTCTATATATACTCACCACATGATAGATACATATATATACCA<br>CAACCAAAACAAAAGGTTTT<br>ATAAGTTCACAACATTTTTTATATACATACAAATAAACTCTAACCATTTT<br>CTCTTCACTAAAATTTCTTC<br>ATTACAAATCTAACAATTTACTTGATCCAATGGCACCATCAATTGCACAA<br>AATGGACATATTAATGGAGA<br>AGTAGCTATGGATTTGTGCAAGAAATCAATCAATGATCCATTGAATTGGG<br>AAATGGCTGCTGATTCTTTA<br>AGAGGCAGCCATTTGGATGAAGTGAAAAAGATGGTGGATGAATTTAGAAA<br>GCCAATTGTGAAACTTGGGG<br>GTGAAACTTTGTCAGTTGCACAAGTTGCATCCATTGCAAATGTTGATGAC<br>AAAAGTAATGGGGTTAAAGT<br>GGAACTTTCTGAAAGTGCAAGGGCTGGTGTGAAAGCTAGTAGTGATTGGG<br>TTATGGATAGTATGAGTAAA<br>GGTACAGATAGTTATGGTGTTACTGCTGGATTTGGAGCAACATCTCATAG<br>AAGAACAAAAAATGGTGGTG | AAA34179.2<br>ADR78835.1<br>AAA99500.1<br>AAC18871.1<br>AAC18870.1<br>AAA33805.1<br>AIC66437.1<br>AGY49231.1<br>AEW43005.1<br>AFP24940.1<br>AER58180.1<br>ADD12041.1<br>AEE81750.1<br>AAP59440.1<br>AAP59439.1<br>AAP59438.1<br>ACG80829.1<br>ACG80828.1<br>ACG56648.1<br>ACG56647.1 |

TABLE 2-continued

| Enzyme | Gene Sequence | Accession Numbers |
|---|---|---|
| | CTCTTCAAAAAGAACTTATTAGGTAAACAAACTATTTTTTTCGTTATAT ATACTAACAATGTAAAGAAT TTAATATTTTTTGTTATATATACTAACAATGTAAAAAATTTAATATTTT TTTGTTATATATACTAACAA TGTAAAGAATTTAATATTTTTTTGTTATACATAGCTTATCGACTACTTAA GTGCTCCATTGATAAAGATT TTTTTTTGTTTTACGCGAAGGGGATTCGGATGAATTCAGTTAAAATGTG ATCTTAATGAATTATGATAT TTTTTTGTAGGTTCTTGAATGCTGGAGTTTTTGGTAATGGAATAGAATCA TTTCACACATTGCCACATTC AGCAACAAGGGCAGCTATGCTTGTTAGGATCAACACTCTGCTTCAAGGCT ACTCTGGCATTAGATTTGAG ATCTTGGAAGCAATCACTAAGTTGATCAATAGCAACATCACCCCGTGTTT GCCTCTCCGTGGCACGATCA CTGCCTCGGGTGATCTCGTCCCTTTGTCCTATATTGCTGGTTTGCTCACT GGCAGACCTAATTCCAAGGC TGTTGGACCCAATGGTGAGAAACTTAATGCTGAGGAAGCTTTCTGCGTGG CTGGTATTAGTGGTGGATTT TTCGAGTTGCAGCCTAAGGAAGGACTTGCACTTGTGAATGGCACAGCAGT TGGTTCTGCTATGGCATCAA TAGTCCTGTTTGAGTCCAATATCTTTGCTGTTATGTCTGAAGTTTTATCA GCGATTTTTACTGAAGTGAT GAACGAAAGCCCGAATTCACTGACTATTTGACACACAAGTTGAAGCATC ACCCTGGTCAGATTGAGGCT GCTGCTATTATGGAACACATTTTGGATGGAAGCTCTTATGTGAAGGTAGC TCAGAAGCTCCATGAAATGG ATCCTCTTCAAAAACCAAAGCAAGATCGTTATGCTCTCCGAACATCTCCA CAATGGCTTGGACCTCAGAT TGAAGTCATTCGTGCTGCAACTAAGATGATCGAGAGGGAGATTAACTCAG TGAACGACAATCCATTGATC GATGTTTCAAGAAACAAGGCCTTACATGGTGGCAACTTCCAAGGAACCCC TATTGGTGTCTCCATGGATA ATACAAGATTGGCCCTTGCATCAATTGGTAAATTGATGTTTGCCCAATTC TCAGAGCTTGTCAACGACTA TTACAACAACGGGTTGCCATCTAATCTGACAGCAGGAAGGAATCCAAGCT TGGACTATGGTTTCAAGGGC GCTGAAATCGCGATGGCTTCTTACTGCTCGGAACTTCAATTCTTGGCAAA TCCAGTGACTAACCATGTCT AAAGTGCTGAGCAACACAACCAAGATGTGAATTCCTTGGGCTTAATTTCA GCCAGGAAAACAGCTAAGGC TGTTGATATCTTGAAGATAATGTCATCAACCTATCTCGTGGCTCTTTGCC AAGCTATTGACTTACGACAT TTGGAGGAAAACTTGAAGAGTGTTGTCAAGAACACAGTTAGCCAAGTAGC TAAGAGAACTTTGACAATGG GTGCTAATGGTGAACTTCATCCAGCAAGATTCAGCGAAAAAGAATTGCTT CGAGTCGTGGATAGAGAATA CTTGTTTGCCTATGCTGATGATCCCTGCAGCTCCAACTACCCTTTGATGC AGAAGCTGAGACAAGTCCTT GTTGATCAAGCAATGAAGAATGGTGAAAGTGAGAAGAATGTCAACAGCTC AATCTTCCAAAAGATTGGAG CTTTCGAGGACGAATTAATCGCTGTGTGTTGCCTAAAGAAGTTGAGAGTGTA AGAGCTGTTTTTGAAAGTGG CAACCCTTTAATTCGTAACAGGATCACAGAATGCAGATCATATCCATTGT ACAGGTTGGTGAGAGAAGAA CTTGGAACAGAATTGTTGACGGGTGAAAAAGTTCGATCACCTGGTGAGGA GATTGATAAAGTGTTTACAG CAATATGTAATGGACAGATTATTGATCCATTGTTGGAGTGTCTGAAGAGC TGGAATGGTGCTCCTCTTCC AATCTGCTAAATGTGTTATTCTTTCAAGTTCTTTTTTTGTACCTTTTAGT GAATTACTAGAATTATAATG ATGTTATGAACTTATATTAAAAAAAAATATTTTTGACTATAAAATTTAGT TTTGTTATTGAAATTAAAGG CTCAATCTGTGTTCTTTCCTTCTGTTATCTGAATATTATAAGAATTCAAG TAATCTTTTAGCTTTGTGAA CATGATGACATGCTTTCTT (SEQ ID NO: 2) | |
| Histidine Ammonia- Lyase | ATGATCACGCTTACCCCCGGCCACCTGACCCTCCCGCAACTGCGCCAGAT CGCGCGCGAGCCCGTGCAGC TGACGCTGGATCCGGCCAGCTTCGCGAAGATCGACGCGGGCGCGAAGGCC GTGTCCGACATCGCCGCGAA GGGCGAGCCGGCGTACGGCATCAACACGGGCTTCGGTCGTCTGGCCAGCA CGCATATCCCGCACGATCAG CTCGAATTGCTGCAGAAGAACCTCGTGCTGTCGCATGCAGTCGGTGTCGG CGAGCCGATGGCGCGTTCGT CGGTGCGTCTGCTGATCGCGCTGAAGCTGTCGAGCCTCGGCCGCGGCCAT TCGGGCATTCGCCGCGAAGT | BAG44062.1 YP_005225923.1 CDF52938.1 ABR76232.1 AAL19728.1 AEW60321.1 AEW51583.1 ABQ54772.1 AAX64695.1 AAU27462.1 |

TABLE 2-continued

| Enzyme | Gene Sequence | Accession Numbers |
|---|---|---|
| | GATGGACGCGCTGATCAAGCTGTTCAACGCCGACGTGCTGCCGCTGATTC<br>CGGTGAAGGGCTCGGTCGGC<br>GCATCGGGCGACCTCGCGCCGCTCGCGCACATGTCGGCCGTGCTGCTCGG<br>CGTCGGCGAAGTGTTCATTC<br>GCGGCGAGCGCGCGAGCGCGGTGGACGGGTTGCGCGTCGCGGGCCTCGCG<br>CCGCTGACGCTGCAGGCGAA<br>GGAAGGCCTCGCGCTGCTGAACGGTACGCAGGCGTCGACGGCGCTCGCGC<br>TCGACAACCTGTTCGCGATC<br>GAAGACCTGTACCGCACGGCGCTCGTCGCCGGCGCGCTGTCGGTCGATGC<br>GGCGGCCGGCTCGGTGAAGC<br>CGTTCGACGCGCGCATCCACGAACTGCGCGGCCATCGCGGCCAGATCGAT<br>GCGGCGGCCGCGTATCGCGA<br>GCTGCTCGAAGGCTCGGCGATCAACCTCTCGCATCGCGACTGCGGCAAGG<br>TGCAGGATCCGTACAGCCTG<br>CGCTGCCAGCCGCAGGTGATGGGCGCGTGCCTGGACCAGATGCGTCATGC<br>GGCCGACGTGCTGCTCGTCG<br>AGGCGAACGCGGTATCGGACAACCCCGCTGATCTTCCCGGATACCGGCGAA<br>GTGCTGTCGGGCGGCAATTT<br>CCATGCGGAGCCCGTCGCGTTCGCGGCCGACAACCTCGCGCTCGCGGCTG<br>CGGAAATCGGCGCGCTGGCC<br>GAGCGCCGCATCGCGCTGCTGATCGACGCGACGCTGTCGGGCCTGCCGCC<br>GTTCCTCGTGAAGGATGCG<br>GCGTGAACTCGGGCTTCATGATTGCGCACGTGACGGCAGCTGCGCTCGCA<br>TCGGAGAACAAGACGCTCGC<br>GCATCCGGCGTCGGTCGATTCGCTGCCGACCTCGGCGAACCAGGAAGACC<br>ACGTGTCGATGGCGACGTTC<br>GCGGCACGCAAGCTGGCCGACATCGCCGACAACACGAAGCACATCCTCGC<br>GATCGAACTGCTCGCGGCCG<br>CGCAGGGCGTCGATCTGCGCGAGAACGAGACGAGCCCGAAGCTCGCGGAA<br>GTGATGAAGACGATTCGCAG<br>CAAGGTCGCGCATTACGAGCTCGACCACTACTTTGCGCCGGACATCGCCG<br>TGATCGCGAAGCTCGTCGTC<br>GAGCGCGCGTTCGCGAAGCACTGCCCGTTCGCCTTCGCATCGGAGCAGTA<br>A (SEQ ID NO: 3) | WP_021000087.1<br>YP_005185682.1<br>YP_001250118.1<br>EFC47317.1<br>AAH89809.1<br>BAH62483.1<br>XP_002680061.1<br>AAO73411.1<br>CAI79696.1<br>CAI79696.1 |
| Tyrosine Ammonia-<br>Lyase | GTGACGCAGGTCGTGGAACGTCAGGCTGATCGGCTCAGCAGCAGGGAGTA<br>CCTGGCCCGGGTCGTGCGCA<br>GCGCCGGGTGGGACGCCGGTCTCACCTCGTGCACCGACGAGGAGATCGTC<br>CGGATGGGCGCGAGCGCGCG<br>CACCATCGAGGAGTACCTGAAGTCCGACAAGCCCATCTACGGCCTGACGC<br>AGGGCTTCGGTCCGCTGGTG<br>CTGTTCGACGCCGACTCGGAGCTGGAGCAGGGCGGCTCGCTGATCTCGCA<br>CCTGGCACCGGCCAGGGCG<br>CGCCACTGGCCCCGGAGGTGTCGCGGCTGATCCTCTGGCTGCGCATCCAG<br>AACATGCGCAAGGGGTACTC<br>GGCGGTCTCGCCGGTGTTCTGGCAGAAGCTCGCCGACCTGTGGAACAAGG<br>GGTTCACCCCCGGCGATCCC<br>CGGCACGGCACGGTCAGCGCGAGCGGCGACCTGCAACCGCTGGCGCACGC<br>CGCGCTCGCCTTCACCGGTG<br>TCGGCGAGGCGTGGACCCGGGACGCCGACGGCCGGTGGTCCACCGTGCCG<br>GCCGTGGACGCGCTCGCCGC<br>GCTGGGGGCGGAGCCGTTCGACTGGCCGGTGCGCGAGGCGCTGGCGTTCG<br>TCAACGGGACCGGCGCGAGC<br>CTCGCGGTGGCTGTGCTCAACCACCGGTCCGCCCTGCGGCTGGTCCGCGC<br>CTGCGCCGTGCTGCTCTCCGCGC<br>GGCTGGCGACCCTGCTGGGGGCCAATCCCGAGCACTACGACGTGGGGCAC<br>GGTGTCGCGCGCGGCCAGGT<br>CGGTCAGCTGACCGCGGCGGAGTGGATCCGGCAGGGGCTGCCCCGGGGCA<br>TGGTGCGCGACGGCAGCCGC<br>CCGCTCCAGGAGCCGTACAGCCTGCGGTGCGCGCCGCAGGTGCTCGGCGC<br>GGTGCTCGACCAGCTCGACG<br>GCGCGGGCGACGTGCTGGCGCGGGAGGTCGACGGCTGCCAGGACAACCCG<br>ATCACCTACGAGGGCGAGCT<br>GCTGCACGGCCGGCAACTTCCACGCCATGCCGGTGGGTTTCGCCTCCGACC<br>AGATCGGGTTGGCCATGCAC<br>ATGGCCGCCTACCTGGCCGAGCGCCAGCTGGGTCTGCTGGTCAGCCCGGT<br>GACCAACGGCGACCTGCCGC<br>CCATGCTCACCCCCGCGCCGGGCGCGGTGCCGGGCTGGCCGGGGTGCAG<br>ATCAGCGCGACCTCGTTCGT<br>CTCGCGGATCCGGCAGCTGGTGTTCCCCGCCTCGCTGACCACCCTGCCGA<br>CCAACGGCTGGAACCAGGAC<br>CACGTGCCGATGGCGCTCAACGGGGCGAACTCGGTGTTCGAGGCGTTGGA<br>GCTCGGCTGGCTGACGGTCG<br>GGTCGCTGGCGGTGGGCGTCGCGCAGCTCGCGGCCATGACCGGCCACGCC<br>GCGGAGGGCGTCTGGGCGGA<br>GCTGGCCGGGATCTGCCCGCCGCTGGACGCCGACCGCCCGCTGGGCGCCG<br>AGGTGCGCGCCGCGCGCGAC | YP_007039999.1<br>Q8GMG0.1<br>WP_015103237.1<br>CCH33126.1<br>AGZ04575.1<br>GAK34477.1<br>AIG26365.1<br>WP_030814263.1<br>WP_030592622.1<br>WP_030583802.1<br>WP_030225885.1<br>WP_030107056.1<br>WP_010261615.1<br>WP_009065811.1<br>WP_029043904.1<br>WP_029027607.1<br>WP_029025670.1<br>WP_029023988.1<br>WP_029020280.1<br>WP_028673581.1 |

TABLE 2-continued

| Enzyme | Gene Sequence | Accession Numbers |
|---|---|---|
| | CTGCTGTCCGCGCACGCGGACCAACTGCTCGTCGACGAGGCAGACGGGAA<br>GGATTTCGGATGA (SEQ ID NO: 4) | |
| Glutamate<br>Dehydrogenase | ATGTCAGCAAAGCAAGTCTCGAAAGATGAAGAAAAAGAAGCTCTTAACTT<br>ATTTCTGTCTACCCAAACAA<br>TCATTAAGGAAGCCCTTCGGAAGCTGGGTTATCCGGGAGATATGTATGAA<br>CTCATGAAAGAGCCGCAGAG<br>AATGCTCACTGTCCGCATTCCGGTCAAAATGGACAATGGGAGCGTCAAAG<br>TGTTCACAGGCTACCGGTCA<br>CAGCACAATGATGCTGTCGGTCCGACAAAGGGGGGCGTTCGCTTCCATCC<br>AGAAGTTAATGAAGAGGAAG<br>TAAAGGCATTATCCATTTGGATGACGCTCAAATGCGGGATTGCCAATCTT<br>CCTTACGGCGGCGGGAAGGG<br>CGGTATTATTTGTGATCCGCGGACAATGTCATTTGGAGAACTGGAAAGGC<br>TGAGCAGGGGGTATGTCCGT<br>GCCATCAGCCAGATCGTCGGTCCGACAAAGGATATTCCAGCTCCCGATGT<br>GTACACCAATTCGCAGATTA<br>TGGCGTGGATGATGGATGAGTACAGCCGGCTGCGGGAATTCGATTCTCCG<br>GGCTTTATTACAGGTAAACC<br>GCTTGTTTTGGGAGGATCGCAAGGACGGGAAACAGCGACGGCACAGGGCG<br>TCACGATTTGTATTGAAGAG<br>GCGGTGAAGAAAAAAGGGATCAAGCTGCAAAACGCGCGCATCATCATACA<br>GGGCTTTGGAAACGCGGGTA<br>GCTTCCTGGCCAAATTCATGCACGATGCGGGCGCGAAGGTGATCGGGATT<br>TCTGATGCCAATGGCGGGCT<br>CTACAACCCAGACGGCCTTGATATCCCTTATTTGCTCGATAAACGGGACA<br>GCTTTGGTATGGTCACCAAT<br>TTATTTACTGACGTCATCACAAATGAGGAGCTGCTTGAAAAGGATTGCGA<br>TATTTTAGTGCCTGCCGCGA<br>TCTCCAATCAAATCACAGCCAAAAACGCACATAACATTCAGGCGTCAATC<br>GTCGTTGAAGCGGCGAACGG<br>CCCGACAACCATTGATGCCACTAAGATCCTGAATGAAAGAGGCGTGCTGC<br>TTGTGCCGGATATCCTAGCG<br>AGTGCCGGCGGCGTCACGGTTTCTTATTTTGAATGGGTGCAAAACAACCA<br>AGGATATTATTGGTCGGAAG<br>AAGAGGTTGCAGAAAAACTGAGAAGCGTCATGGTCAGCTCGTTCGAAACA<br>ATTTATCAAACAGCGGCAAC<br>ACATAAAGTGGATATGCGTTTGGCGGCTTACATGACGGGCATCAGAAAAT<br>CGGCAGAAGCATCGCGTTTC<br>CGCGGATGGGTCTAA (SEQ ID NO: 5) | P39633.3<br>KEG08275.1<br>NP_001233850.1<br>NP_001268039.1<br>AEW04907.1<br>YP_007161255.1<br>YP_005256579.1<br>YP_004932652.1<br>YP_004442444.1<br>YP_004412348.1<br>YP_004410986.1<br>YP_004372731.1<br>YP_004367667.1<br>YP_004366366.1<br>YP_004343968.1<br>YP_004343356.1<br>YP_004261766.1<br>YP_004270382.1<br>YP_004099961.1<br>YP_003967811.1 |
| Glutamate<br>Ammonia-Lyase | ATGTCCATCAAAGACGCTGTAAAACTGATTGAAGAAAGCGAAGCCCGCTT<br>TGTCGATTTGCGCTTTACCG<br>ATACCAAAGGCAAGCAGCACCACTTTACCGTGCCTGCGCGCATCGTGTTG<br>GAAGACCCCGAAGAGTGGTT<br>CGAAAACGGACAGGCGTTTGACGGTTCGTCCATCGGCGGCTGGAAAGGCA<br>TTCAGGCTTCCGATATGCAG<br>CTTCGCCCCGATCCCGCCACGGCGTTTATCGATCCTTTTTATGATGATGT<br>TACCGTCGTCATTACCTGCG<br>ACGTTATCGATCCCGCCGACGGTCAGGGTTACGACCGCGACCCGCGCTCC<br>ATCGCACGCCGCGCCGAAGC<br>CTATTTGAAATCTTCCGGTATCGGCGACACGGCATACTTCGGTCCCGAAC<br>CCGAGTTTTTCGTCTTCGAC<br>GGCGTAGAATTTGAAACCGATATGCACAAAACCCGTTACGAAATCACGTC<br>CGAAAGCGGCGCATGGGCCA<br>GCGGCCTGCATATGGACGGTCAAAACACCGGCCACCGCCCTGCCGTCAAA<br>GGCGGTTACGCGCCCGTCGC<br>GCCGATTGACTGCGGTCAGGATTTGCGTTCCGCGATGGTAAACATTTTGG<br>AAGGACTCGGCATCGAAGTC<br>GAAGTGCACCACGAAGTCGGTACCGGCAGCCAAATGGAAATCGGCAC<br>GCGCTTCGCCACCTTGGTCA<br>AACGCGCCGACCAAACCCAAGACATGAAATATGTGATTCAAAATGTCGCC<br>CACAACTTCGGCAAAACCGC<br>CACCTTCATGCCCAAACCCATTATGGGCGACAACGGCAGCGGTATGCACG<br>TTCACCAATCCATCTGGAAA<br>GACGGTCAAAACCTGTTCGCAGGCGACGGCTATGCCGGCTTGAGCGACAC<br>CGCGCTCTACTACATCGGCG<br>GCATCATCAAACACGCCAAAGCCCTGAACGCGATTACCAATCCGTCCACC<br>AACTCCTACAAACGCCTTGT<br>GCCGCACTTTGAAGCGCCGACCAAACTGGCATATTCCGCCAAAAACCGTT<br>CCGCTTCCATCCGTATTCCG<br>TCTGTGAACAGCAGCAAGGCGCGCCGCATCGAAGCGCGTTTCCCCGACCC<br>GACCGCCAACCCGTACTTGG<br>CGTTCGCTGCCCTGCTGATGGCGGGTTTGGACGGCATTCAAAACAAAATC<br>CATCCGGGCGATCCTGCCGA<br>TAAAAATCTCTACGACCTGCCGCCGGAAGAAGACGCGCTCGTCCCGACCG<br>TTTGCGCTTCTTTAGAAGAA | CBX22311.1 |

TABLE 2-continued

| Enzyme | Gene Sequence | Accession Numbers |
| --- | --- | --- |
| | GCCCTCGCCGCGCTCAAAGCCGACCACGAATTCCTCTTACGCGGCGGCGT<br>GTTCAGCAAAGACTGGATCG<br>ACAGCTACATCGCCTTTAAAGAGGAAGATGTCCGCCGCATCCGTATGGCG<br>CCGCATCCGCTGGAATTTGA<br>AATGTATTACAGCCTGTAA (SEQ ID NO: 6) | |
| Threonine Dehydrogenase | AGGAGGTGTTTTAATAATGAAAGGTTTTGCAATGCTCAGTATCGGTAAAG<br>TCGGTTGGATTGAAAAAGAA<br>AAGCCTACTCCCGGCCCTTTTGACGCTATTGTAAGACCTCTAGCTGTGGC<br>CCCTTGCACTTCGGACGTTC<br>ATACCGTTTTTGAAGGTGCTATTGGCGAAAGACATAACATGATACTCGGT<br>CACGAAGCTGTAGGTGAAGT<br>AGTTGAAGTAGGTAGTGAGGTAAAAGATTTTAAACCTGGTGATCGCGTTG<br>TGGTACCAGCTATTACCCCT<br>GATTGGCGAACCTCTGAAGTGCAAAGAGGATATCACCAACACTCTGGTGG<br>AATGCTGGCAGGCTGGAAAT<br>TTTCGAATATAAAGATGGTGTTTTTGGTGAATTTTTTCATGTGAACGAT<br>GCTGATATGAATTTAGCACA<br>TCTGCCTAAGGAAATTCCATTGGAAGCTGCAGTTATGATTCCCGATATGA<br>TGACTACTGGCTTTCACGGA<br>GCCGAACTGGCAGATATAGAATTAGGTGCGACGGTAGCGGTTTTGGGTAT<br>TGGCCCAGTAGGTCTTATGG<br>CAGTCGCTGGTGCCAAATTGCGGGGTGCTGGAAGGATTATCGCAGTAGGC<br>AGTAGACCAGTTTGTGTAGA<br>TGCTGCAAAATACTATGGAGCTACTGATATTGTAAACTATAAAGATGGTC<br>CTATCGACAGTCAGATTATG<br>GATTTAACGGAAGGCAAAGGTGTTGATGCTGCCATCATCGCTGGAGGAAA<br>TGTTGACATCATGGCTACAG<br>CAGTTAAGATTGTTAAACCTGGTGGCACCATCGCTAATGTAAATTACTTT<br>GGCGAAGGAGATGTTTTGCC<br>TGTTCCTCGTCTTGAATGGGGTTGCGGCATGGCTCATAAAACTATAAAAG<br>GCGGGCTATGCCCCGGTGGA<br>CGTCTAAGAATGGAAAGACTGATTGACCTTGTTGTTTATAAGCGTGTCGA<br>TCCTTCTAAGCTCGTCACTC<br>ACGTTTTCCGGGGATTTGACAATATTGAAAAAGCCTTTATGTTGATGAAA<br>GACAAACCAAAAGACCTAAT<br>CAAACCTGTTGTAATATTAGCATAA (SEQ ID NO: 7) | NP_622353.1<br>EPX86072.1<br>AFT82159.1<br>YP_006796158.1<br>EJZ15419.1<br>YP_001727630.1<br>ACA82186.1<br>AGZ44086.1<br>AEB44998.1<br>YP_008737139.1<br>EPX87740.1<br>YP_004405598.1<br>BAN60779.1<br>EPE39095.1<br>EPC57128.1<br>EME23086.1<br>ACI75705.1<br>ACI75704.1<br>ACI75703.1<br>ACI75702.1 |
| Threonine Ammonia-Lyase | ATGGCTGACTCGCAACCCCTGTCCGGTACCCCGGAAGGTGCCGAATATTT<br>AAGAGCGGTGCTGCGCGCGC<br>CGGTCTACGAAGCGGCGCAGGTCACGCCGCTACAGAAAATGGAAAAACTG<br>TCGTCGCGTCTCGATAACGT<br>GATTCTGGTGAAGCGCGAAGATCGCCAGCCAGTTCATAGCTTTAAGTTGC<br>GCGGCGCATACGCCATGATG<br>GCGGGCCTGACGGAAGAACAAAAAGCACACGGCGTGATTACCGCTTCTGC<br>AGGTAACCACGCGCAGGGCG<br>TCGCGTTTTCTTCCGCACGGTTAGGCGTGAAGGCGCTGATCGTCATGCCA<br>ACCGCCACCGCCGATATCAA<br>AGTTGATGCGGTGCGCGGCTTTGGCGGCGAAGTGCTGCTTCACGGCGCAA<br>ATTTCGATGAAGCGAAAGCG<br>AAAGCGATCGAACTGTCACAGCAGCAGGGTTTCACCTGGGTACCGCCGTT<br>CGATCATCCGATGGTGATCG<br>CCGGGCAAGGCACGCTGGCGCTGGAACTGCTCCAGCAGGACGCCCATCTC<br>GACCGCGTATTTGTACCGGT<br>CGGCGGCGGCGGTCTGGCAGCGGGTGTGGCGGTGCTGATCAAACAACTGA<br>TGCCGCAAATCAAAGTAATC<br>GCCGTGGAAGCGGAAGATTCCGCCTGCCTGAAAGCGGCGCTGGATGCGGG<br>TCATCCCGTTGATCTGCCCC<br>GCGTGGGGCTGTTTGCTGAAGGCGTCGCGGTAAAACGCATCGGCGATGAA<br>ACCTTCCGTTTGTGCCAGGA<br>GTATCTTGACGACATCATCACCGTCGATAGCGATGCCATCTGTGCGGCGA<br>TGAAAGATCTGTTCGAAGAT<br>GTGCGCGCGGTGGCGGAACCTTCCGGCGCGCTGGCGCTGGCGGGGATGAA<br>AAAATACATCGCCCAGCACA<br>ACATTCGCGGTGAACGGCTGGCGCATATTCTTTCCGGTGCTAACGTGAAC<br>TTTCACGGTCTGCGCTACGT<br>CTCGGAACGCTGCGAACTGGGCGAACAGCGTGAAGCGTTGTTGGCGGTGA<br>CCATTCCGGAAGAAAAGGC<br>AGCTTCCTCAAATTCTGCCAACTGCTTGGCGGGCGTTCGGTCACCGAGTT<br>CAACTACCGTTTTGCCGATG<br>CCAAAAACGCCTGCATCTTTGTCGGCGTGCGCTTAAGCCGTGGCCTCGAA<br>GAGCGCAAAGAAATTTTGCA<br>GATGCTCAACGACGGTGGCTACAGCGTGGTTGATCTCTCCGACGACGAAA<br>TGGCGAAGCTGCATGTGCGC<br>TATATGGTTGGCGGGCGTCCATCGCATCCGTTGCAGGAACGCCTATACAG<br>CTTCGAATTCCCGGAATCAC | EGP22802.1<br>AIL15845.1<br>KFJ14411.1<br>B22317<br>ESE06785.1<br>ESD87895.1<br>ESD77040.1<br>ESD56952.1<br>ESD26867.1<br>ESD18649.1<br>ESC98561.1<br>ESA95751.1<br>ESA86931.1<br>ESA78951.1<br>ESA72735.1<br>ESA67809.1<br>ERL21545.1<br>ERK40933.1<br>ERJ97484.1<br>ERH28800.1 |

TABLE 2-continued

| Enzyme | Gene Sequence | Accession Numbers |
|---|---|---|
| | CGGGCGCGCTGCTGCGCTTCCTCAACACGCTGGGTACGCACTGGAACATC<br>TCGCTGTTCCATTATCGCAG<br>CCACGGTACCGACTACGGGCGCGTACTGGCGGCGTTCGAGCTTGGCGATC<br>ATGAACCGGATTTTGAAACC<br>CGGTTGAATGAACTGGGCTACGATTGCCACGACGAAACCAATAACCCGGC<br>GTTCAGGTTCTTTTTGGCGG<br>GTTAG (SEQ ID NO: 8) | |
| Serine Dehydrogenase | ATGAGCGGTACCATCCTCATCACCGGCGCCACGTCCGGCTTCGGACAGGC<br>CACGGCGCGGCGTTTCGTCA<br>AGGAAGGCTGGAAGGTCATCGGCACAGGTCGGCGGGCGGAACGGCTGGAG<br>GCGCTGGCGCAAGAACTCGG<br>CTCCGCCTTTCACGGCGCTGCCTTCGATGTTACCGACGAAGATGCCACTA<br>GAAAGGCACTTGCGGCTTTG<br>CCGGAAGGTTTCCGGGACATCGATATTCTCGTCAACAATGCGGGGCTTGC<br>GCTCGGCACCGCACCTGCAC<br>CGCAGGTGCCGCTGAAAGACTGGCAGACCATGGTGAACACCAACATCACC<br>GGTCTTTTGAACATCACCCA<br>CCATCTTTTGCCCACGTTGATCGACCGCAAGGGCATTGTCATCAACCTTT<br>CCTCGGTAGCTGCGCACTGG<br>CCCTATGCGGGCGGCAATGTCTATGCCGGAACGAAAGCCTTCCTGCGGCA<br>ATTCTCGCTCGGTCTGCGCT<br>CCGACCTGCATGGCAAGGGCGTGCGCGTCACCTCGATCGAACCGGGCATG<br>TGCGAAACGGAATTCACGCT<br>TGTTCGCACCGGCGGCAATCAGGATGCCTCGGACAATCTTTACAAGGGCG<br>TCAATCCGATCACGGCCGAG<br>GATATCGCCAATACGATCCATTGGGTCGCCTCGCAGCCCAAACATATCAA<br>CATCAACAGCCTCGAACTCA<br>TGCCGGTCAACCAGTCCTTTGCCGGTTTCCAAGTGCATCGGGAAAGTTGA<br>(SEQ ID NO: 9) | ADY67207.1<br>YP_004444298.1<br>EAZ63492.1<br>XP_001387515.1<br>BAB07807.1<br>EMS96834.1<br>EKJ96295.1<br>EHJ96027.1<br>EHH03760.1<br>WP_028707025.1<br>NP_356536.1<br>AEQ50417.1<br>AAK89321.1<br>YP_004898167.1<br>YP_064393.1<br>WP_003522480.1<br>EGP55658.1<br>EGL63994.1<br>KFC62486.1<br>WP_031354348.1 |
| Serine Ammonia-Lyase | ATGATGACCAAAAACGAAATCCAAAAGTGGGTAAAGGAATTCCCGCTGCT<br>TGAAACGATCATGGCGGCCG<br>AAGAGGTATTTTGGCGCAATCCAAAATATCACGCGTTTGCGCAAGCTATT<br>CGAACGATTCCTTTACGCGA<br>ACGCGATGTCAAGGAGGCCGAAGAGCGATTGCGCCGCTTTGCCCCCTACA<br>TCGCGAAAGTGTTTCCCGAG<br>ACGCGAACGGCCCACGGTATCATCGAATCCCCTTTAGTGCGGATTCCGAA<br>CATGAAACAGCGTTTGGAAA<br>AGATGTTTCAGACCAACATCGAGGGGGATCTGTTGCTAAAATGCGACAGC<br>CATCTTCCCATCTCCGGATC<br>GATCAAGGCGAGAGGGGAATCTACGAGGTTCTGAAACATGCGGAAGAAC<br>TCGCTCTGGCAAACCATATG<br>ATCACCATGGGGGATGACTATGCGGTCATGGCCAGCGAAGAATTCCGGCA<br>GTTCTTTTCCCGCTATTCGC<br>TTGTCGTTGGTTCGACGGGAAATTTAGGCTTGAGTATCGGCATCATCGGG<br>GCGCAGCTTGGGTTCCGCGT<br>TACCGTTCATATGTCAGCCGATGCGAAACAATGGAAAAAAGACTTGTTGC<br>GAAGCAAAGGGGTTGCGGTC<br>ATCGAACATCTCACCGACTACAACAAGGTGGTGGAAGAGGCGCGAAGACA<br>GTCCGCCGAGGATCCAACGT<br>CGTATTTTATCGATGATGAGAACTCGATCCATCTGTTTTTAGGCTATGCG<br>GTGGCGGCGTTTCGGCTGAA<br>AAAGCAATTAGAGGACATGAACATCACGGTTGATGAAAACCACCCGCTCT<br>TTGTATATCTTCCTTGCGGC<br>GTCGGCGGCGGTCCGGGCGGGGTGACGTTTGGGCTGAAGCTCGTGTACGG<br>CGATCATGTCCATTGCTTTT<br>TCGCTGAGCCGACGCATTCGCCTTGCATGTTGCTCGGCCTGATGACGGGA<br>CAGCACGACCGCGTGTCGGT<br>GCAAGATTTTGGCCTCGACAATAAGACCGAAGCGGACGGGCTAGCGGTGG<br>GGCGGCCGTCAAGGTTGGTG<br>GGGAACATGCTTGAGAACGTCATCAGCGGCGTCTATACGGTGGACGATGC<br>GACGCTTTACCGCTTGCTCG<br>CGGCGATGGTGGAAACGGAGGAAATCTATTTAGAGCCGTCCGCCTTGGCG<br>GGGGTGGCGGGGCCTGTTCG<br>GCTGTTTCGTGATTTGGCGGGGCAAACGTACGTAGAGGCAAACGGTTTGA<br>AAGAAAAGATGAAAAACGCC<br>GTCCATATTGGCTGGGCGACAGGCGGAAGCATGGTGCTAAAGGATGTGAT<br>GGAGGCCTATTATCGGGAAG<br>GCGTGCGCATCGAAACGATGACGGGAACGGTTTTTCTGAAGGACGATAA<br>(SEQ ID NO: 10) | KFL14920.1<br>AIF56070.1<br>KFI03369.1<br>KFH36969.1<br>KFH35774.1<br>KFF56112.1<br>WP_031409141.1<br>KFC30598.1<br>KEZ84476.1<br>KEY95863.1<br>KER46054.1<br>WP_030024949.1<br>KEK24273.1<br>KEK22892.1<br>KEK18491.1<br>KEK12402.1<br>WP_029761212.1<br>WP_029758174.1<br>WP_029714078.1<br>WP_029598316.1 |
| Leucine Dehydrogenase | ATGCTGATGTTCGAAGAAATCCAGGCGCGCGGCCACGAGAGCGTCACGCT<br>GCTGCACCACGCCCCCAGCG<br>GCCTGCGCGCCGTGCTCGCCGTGCACTCCACCGTGCTCGGCCCTGCCATT<br>GCCGGCTGCCGCCTGATGCC | YP_004169785.1<br>ADV66120.1<br>ADY26991.1<br>AEW05136.1 |

TABLE 2-continued

| Enzyme | Gene Sequence | Accession Numbers |
|---|---|---|
| | CTGCACCGAGGAACGCGCCGTGCGCGACGCCCTCGCCCTCAGCGAGTCCG<br>TCACGCTCAAGGCCGCCCTC<br>GCGGGCCTGAACTACGGCGGGGGCGCGTGCGTCATGCTCCCCCCGGAAGG<br>CGGCGACATCGACGGGCACG<br>CCCGCGAGGCGCTGTTCCGCGCGCTCGGCCGGCAGATCCGTTACCGCGGT<br>GGCCGCGTCATCCTCACCGA<br>GGACGTCGGCGTGACCGGCCGCGACATCGCCTTCGCCGCGCAGGAAACCG<br>ACAGCACCATGGGCATGCAC<br>ACCGACACGCCCACCGTCACCGCGTACGGCGTGTACCGCGGCATCAAGGC<br>CGCCGCGCGCGCCTACCTCG<br>GCGGCGAGAGCATGCGCGGCGTGCGCGTCGCGCTGCTCGGCGCGGGCGCA<br>GTCGGGCGCACCCTCGCGCA<br>GCACCTGCACCGCGAGGGCGCGCGCCTCACCGTCGCAGACCTGATGTCTG<br>AGCGCGCGCAGGCCCTCGCG<br>GACGACCTCGGCGAGCGCGTCACCGTCGTGAGCGCCGCTGACATCTTCGA<br>CGTGCCGTGCGACGTATTCG<br>CGCCGTGCGCGTTCGGGCACAGCATCAAAAGCGCCGACGTGCCCCGCTTG<br>CAGTGCCGGGTGATCGCCGG<br>CAGCGAACACCACCCGCTCAGCCACAACGGCGAGACGCTCGTGCGCGAAG<br>CGGGCATCACATACATCCCG<br>GACTTCGCCATCAACAGCGCCGGCCTGATGAGCGCCGCGCAGAACCTCAG<br>CATCGAAACGGCGGCGGAAC<br>GCGTGTACGAGAGCGTCGCGCAGATCTGCGCGACCGCGCAGAAGTACGAG<br>AAGCCGCCGCACGTCGTCGC<br>CCGTAAACTCGCGCTGCGCCGCATCGAACTGATCGGCTCCATCAGCGGCC<br>AGTACGCCGGCCAGTAA (SEQ ID NO: 11) | YP_005256808.1<br>YP_004256608.1<br>YP_004346245.1<br>AEA45407.1<br>YP_004101992.1<br>YP_004101991.1<br>YP_003825932.1<br>ADU51265.1<br>ADU51264.1<br>ADL08309.1<br>AFY88585.1<br>YP_004054007.1<br>YP_007092454.1<br>YP_003825216.1<br>ADR21899.1<br>ADL07593.1 |
| Aspartate Dehydrogenase | TCATGTGCCAACACGTATGTTATCACTTAAAATTTTTAGTAAAGTGACTG<br>CTGAATATGCTGCCAAAACA<br>CTTGTTTTTGGATTTAATTCACACACAGTGTTTTTTGTTATAGATTTAAA<br>CTCTCCAAAATCTCCTTTAA<br>CATGGACTTCATGGATATTGTGTTCAACTTCAGGATCTGCAATTATCTTT<br>ACATCCGCATCTATTCCAGA<br>GGCTAGACTTAATGCCGCAGCAACGTTAATATTCACTGGAAATTTTTTAA<br>CAGCTTCTGAGGATTTCCCT<br>TTAAACACGACCTCCTTTTTTTTGGTCTTAACACCTAACGAAGTAGGTGA<br>TTTTCTCGTTATAAGTTTTA<br>TTTCTTTTATCTTACCTAAGGATGCGGCTTTTACACCATCTAAACCAATT<br>ATTGCACCGGAAGGTATGTA<br>TATATTAGCTCCTGATTCTCTAGATTCCTTTATCAATCTTCTTCTAACTT<br>TCTCATCTAATAGTGCACCC<br>ACACTCATAATCAAAACATCTATACCTCTACTAATTATATTGGGCACAAT<br>TTCTTTTACTGCCTCTTGAG<br>AAGCAGATTCAATTATCAAATCAACTCCATTGAACATTTCTTCTACCTTT<br>TTTACGGCAGTGCCATTTGT<br>TAAATTTGCTAGCTTCTTAGCTTTTCTAAAATTTCTGTCATAAAAATATT<br>TTAATTTTATTTTTTTGATA<br>TCTTGTTTTAAGACAAGGTTAACTATTGTATTTGCAATTGCACCACATCC<br>TATAATCCCACATCTCAT (SEQ ID NO: 12) | ADP76847.1<br>YP_004003609.1<br>ADE37476.1<br>AEH60264.1<br>AEH50568.1<br>YP_004615483.1<br>YP_004659664.1<br>YP_003543121.1<br>YP_003895891.1<br>ADN37453.1<br>ADV47603.1<br>YP_004163101.1<br>ADY50896.1<br>ABX33598.1<br>YP_004272718.1<br>ADN60949.1<br>ACL18032.1<br>ACL16745.1<br>ABX00971.1<br>ADD08173.1 |
| Aspartate Ammonia-Lyase | ATGTCCTCGCCTGCATCATCGCGCATCGAAAAAGACCTGCTTGGTGTTCT<br>CGAAGTACCTGCCAACGCGT<br>ATTACGGCATCCAGACCCTGCGAGCGGTGAACAACTTTCACCTCTCCGGC<br>GTGCCGCTTTCGCACTACCC<br>GAAACTGGTAGTCGCGCTGGCCATGGTCAAGCAGGCGGCAGCGGATGCAA<br>ACCATCAGCTCGGACACCTC<br>AATGACGCCAAGCATGCGGCGATCAGCGAGGCCTGTGCCCGCCTGATCCG<br>CGGCGACTTCCACGATCAGT<br>TCGTGGTCGACATGATCCAGGGCGGCGCTGGCACGTCGACCAACATGAAT<br>GCCAACGAAGTCATCGCCAA<br>CATCGCTCTGAAACCATGGGTTTCGAGAAAGGCGCATACAAACACCTGC<br>ACCCCAACAACGATGTCAAC<br>ATGGCGCAGTCGACCAACGACGCCTACCCCACGGCGATCCGCTTGGGTCT<br>GCTGCTGGGTCACGACGCTC<br>TGCTCGCCAGCCTTTCCAGCCTGATTCAGGCCTTCGCCGCCAAGGGCGAA<br>GAATTCAACCATGTGCTGAA<br>GATGGGCCGCACCCAGTTGCAGGACGCCGTTCCAATGACCCTGGGTCAGG<br>AATTCCGCGCCTTCGCCACC<br>ACCCTGACAGAAGACCTGAACCGCCTGCGCAGCCTGGCGCCAGAGCTGTT<br>GACCGAAGTGAACCTCGGCG<br>GAACCGCCATCGGCACCGGCATCAACGCCGACCCTGGCTATCAGAAGCTG<br>GCAGTCGATCGTCTGGCACT<br>CATCAGCGGCCAGCCTCTGGTGCCAGCAGCCGACCTGATCGAAGCGACCT<br>CCGACATGGGCGCCTTCGTG<br>TTGTTCTCGGGCATGCTCAAGCGTACTGCGGTCAAGCTGTCGAAAATCTG<br>CAACGACCTGCGCCTGCTGT | ELS44542.1<br>EXL32019.1<br>EPF69098.1<br>EDZ32290.1<br>ACC77466.1<br>ET009916.1<br>ETN58394.1<br>AGZ94384.1<br>EGU12843.1<br>AGQ54567.1<br>BAN21048.1<br>ELU36465.1<br>ELU36464.1<br>EDS31003.1<br>BAM20634.1<br>ACO48312.1<br>XP_001828833.2<br>EAU92840.2<br>XP_001849880.1<br>XP_001658988.1 |

TABLE 2-continued

| Enzyme | Gene Sequence | Accession Numbers |
|---|---|---|
| | CCAGCGGCCCACGCACCGGCATCAACGAAATCAACCTGCCGGCACGTCAG CCAGGCAGCTCGATCATGCC CGGCAAGGTCAACCCGGTGATCCCGGAAGCGGTCAATCAGGTTGCCTTCG AAATCATCGGCAACGACCTG TCGCTGACCATGGCAGCCGAAGGAGGACAATTGCAGCTCAACGTGATGGA GCCGCTGATCGCCTACAAGA TCTTCGACTCGATCCGCCTGCTGCAGCGCGCCATGGACATGCTGCGCGAG CACTGCATCGTCGGCATCAC AGCCAACGAACAGCGCTGCCGCGAGCTGGTCGAGCATTCGATCGGTCTGG TCACCGCCCTGAACCCTTAC ATCGGTTACGAGAACTCCACCCGTATCGCCCGCATCGCGCTGGAAACCGG CCGCGGCGTGCTGGAACTGG TGCGTGAGGAAGGTCTGCTCGACGACGCCATGCTCGACGACATCCTGCGC CCGGAAAACATGATCGCTCC GCGTCTGGCCCCCTTGAAGGCCTGA (SEQ ID NO: 13) | |
| Valine Dehydrogenase | TCAGCGACCGCGGGCCTCGGCCATCCGCTGCTCGGCGATCCGGTCGGCCG CCGGCGGCGGGCGGAATGCCG TCCGCCTTCGCACGTGCGAATATTTCCAGCGTGGTGTCGAAGATCTTCGT CGCCTTCGCCTTGCACCGGT CGAAGTCGAACCCGTGCAGCTCGTCGGCGACCTGGATCACGCCGCCGGCG TTGACCACATAGTCGGGTGC GTAGAGGACCGACCGGTCGGCCAGGTCCTTCTCGACACCCGGGTGGGCCA GCTGGTTGTTGGCCGCGCCG CACACCACCTTCGCCGTGAGCACCGGAACGGTCGCGTCGTTGAGCGCGCC GCCGAGCGCGCAGGGCGCGT AGATGTCGAGACCCTCGGTGCGGATCAGCGTCTCGGTGTCCGCCACCACG GTGACCTCGGGGTGCAGATC GGTGATCCGGCGCACCGACTCCTCGCGTACGTCGGTGATCACGACCTCGG CCCCGTCGGAGAGCAGGTGC TCGACGAGGTGGTGGCCCACCTTGCCGACCCCGGCGACGCCGACCTTGCG GCCGCGCAGCGTCGGGTCGC CCCACAGGTGCTGGGCCGAGGCCCGCATGCCCTGGAAGACACCGAACGCG GTGAGGACGGAGGAGTCGCC GGCGCCGCCGTTCTCGGGGGAGCGGCCGGTGGTCCAGCGGCACTCCCTGG CGACGACGTCCATGTCGGCG ACGTAGGTGCCGACATCGCAGGCGGTGACGTACCGGCCGCCGAGCGAGGC GACGAACCGGCCGTAGGCCA GGAGGAGTTCCTCCGTCTTGATCTTCTCCGGGTCGCCGATGATGACGGCC TTGCCGCCACCGTGGTCGAG TCCGGCCAGGGCGTTCTTGTACGACATCCCGCGCGACAGGTTCAGCGCGT CGGCGACGGCCTCGGCCTCG GTCGCGTACGGGTAGAAGCGGGTGCCGCCGAGGCCGGGGCCCAGGGCGGT GGAGTGGAGGGCGATGACGG CCTTGAGGCCGGTGGCACGGTCCTGGCAGATACGACTTGCTCGTGACCC CCCTGATCCGAGTGGAACAG GGTGTGCAGGACGCCGTTAGTCACATCGGTCAC (SEQ ID NO: 14) | YP_007932652.1 AGK78767.1 NP_628270.1 YP_001973234.1 AIJ14557.1 YP_007523209.1 WP_015659426.1 CCK29082.1 CAR62534.1 AGT93561.1 AEK45617.1 ADI08852.1 YP_008454282.1 ESQ05180.1 ESP98677.1 YP_005535074.1 YP_004963983.1 EOD63988.1 EME98953.1 EME52779.1 |
| Glycine Dehydrogenase | CTAGTTGTAAAAGTCGAGGGAGGCGCAACTGCACATGAGGTGACGATCTC CGTAAACCCCGTCAATGCGA CCCACAGTCGGCCAGTACTTTTTCAACGTACGAGTAAGGATAAGGGAATGC CGCCAAACGCCGATCATATG GTTTGTCCCATTTATCATCGGTGACACATCTTGCCGTGTGTGGTGCATTC TTCAAAACATTGTTATCCAC TGGTTGTTCACCTTTTTCAATGGCGGCAATCTCACCTCGAATGGAAATTA GTGCATCTGCCAAGCGATCC AACTCCCGCTTGGGTTCTGATTCGGTGGGTTCAATCATTAAAGTCCCGGG TACAGGAAACGCCAGTGTTG GCGAGTGAATTCCGTAGTCCATCAACCGTTTGGCCACGTCCTCCGCCTCA ATATGAGCTGTCTTCTTGAA CCGTCGAAGATCAACGATAAACTCATGAGCGCAGTAGTTTTCTCCACCCA GGAAAAGAATCGTATAATGG TTCTCTAGGCGCTTCTTCAAGTAGTTTGCATTCAAAACGGCGTACTCTGT ACAAGTTTTGAGCCCGTGTG ATCCAAGCATTAACATCAACATGTACGATATCGGAAGAATTGATGCTGAT CCGTACGCTGATTGTGAGAC TTGGCCGAATGGCTGTGAACCGCCAACTTTTTGGTTGAAAACAGAATTTG GCAAAAGGGGGCCAGATGT TGACGGACAGCTATAGGGCCCATTCCGGGGCCGCCACCACCATGGGGAAT TGAAAACGTCTTGTGGAGAT TAATGTGGCACACGTCGCCACCGATATATCCAGGGCCTGTATAGCCAACC ATGGCGTTAAGATTTGCCCC ATCAATGTAGCATTGTCCACCGTAGTAGTGCGCCATTGATGTAATGGATA AAATATCCTTGTCAAACAAG CCATACGTACTTGGATATGTTATCATGATACACGACAACTCCTTTGCGTG TTTTTGGCAAGATTTCTCCA | KEG12217.1 ADH66904.1 YP_003679410.1 YP_003507491.1 ADN74845.1 ADD28471.1 YP_004445203.1 YP_003911919.1 ADQ81869.1 AEH88507.1 YP_007138219.1 YP_004612601.1 YP_004170318.1 YP_004163559.1 YP_004045375.1 YP_004787190.1 YP_007142361.1 YP_007067896.1 YP_007100788.1 YP_004773043.1 |

TABLE 2-continued

| Enzyme | Gene Sequence | Accession Numbers |
|---|---|---|
| | GGTCATTGATATCAACCCTGCCGTTAGACAAGCATTTCACCAAGACAATA<br>TTCATTCCTGCCAATGTTGC<br>CGAAGCTGGATTCGTACCATGCGCACTCTCTGGAATCAAACAGACGTTGC<br>GGTGTCCTTCCTTCATTGAT<br>AGATGGTACGCACGAATAACACGAAGCCCAGCGTATTCACCTTGGGCGCC<br>ACTATTAGGCTGAAGCGATA<br>CCGCATCCAGACCGGTAATTTCCCTTAACTTTTGCTCAAGATCTAGACAC<br>AACGCACTGTACCCTCGCAC<br>TTGGTCCACTGGGGCAAGGGGATGCACATTGGTGAATTCTGGCCAAGAGA<br>GTGGTAACATAGCAGCGGCA<br>GGGTTAAGCTTCATGGTGCAAGATCCCAACGGGACGCAACCATGCGTAAG<br>GCCGTAATCCTTTCGTTGTA<br>GACGATGAATATAGCGCATCAGTTCACTTTCACTCTTGTACTTTTGAAAC<br>GTTGAGTGTTTCAGGAAATC<br>AGACTTCCGCACCAGATCCAACGGTAGTACCGATTTCTGATCGGCTATTT<br>TGGAAAGGGCTGCGACGACG<br>GGAAGCTTCAACCCTGCAGCCTCCAAAAGTGACACAATGTGTCCATCCGT<br>TGTTGCCTCATCCACAGAAA<br>TGGAGACAGTCCCATTACTGTAATCAACAAAAACATTAATACCCTTCTCA<br>ACACATCGTGTCTTGTAATC<br>CTCCGCTGTAATGCCTTTTAGGTTCACAGTAACAGTGTCGAAAAATGCAC<br>TGTTTACCACAGAGTGTCCT<br>ACTGATTCCATACCAACAGCGAGCACTTTCGCCTTGCCGTGTATCTCATT<br>GGCAATCTCATTTAGACCAT<br>CTGGACCATGGTAGGCGGCATAAAACCCACTCACGTTGGCCAATAACGCT<br>TGTGCAGTACAGATATTTGA<br>TGTGGCGCGCTCACGCTTAATATGTTGTTCACGTGTCTGCAGCGCCATGC<br>GTATGGATGGCTCTCCGGCA<br>GAATCCTTACTGACGCCGATCACACGTCCCGGCATCAACCTCTTAAACTG<br>CTCCTTGACAGCAAAGAACG<br>CGGCGTGAGGACCTCCATATCCTAGTGGAACACCAAAACGCTGGGAGGAT<br>CCCACAACCACATCTGCATT<br>CATTTCACCAGGTGGCTTGACAAGAACACAAGCCATCAAGTCGGTCCCAC<br>AGCAACTAATGACACCGTGC<br>TTCTTTGCATTCTCGAACAGTGGTGAGAAGTCATGAAGCATGCCCATCGC<br>ATCGGTGTTTGTACAAGGA<br>TACCAAACAAGGAACTGTCAGTCCAGTCAATCAGATTCGTGTCGCCCACG<br>ACGACGTTTATCTTGAGCGG<br>TTCGGCTCTTGTCTTAACCATCTCAATGCAGGATGGAAAAACAGTTTTTG<br>ATACGAAGAACGTATTCCGC<br>TTTCGTTGACCATGCTGAAAAGCAAGATGCATCGCCTCGGATGATGCTGT<br>CGCTTGGTCAAGAAGAGATG<br>CATTTGCCACATCCATCTTTGTCAAATCCATAACCATGGTTTGGAAATTC<br>AAAAGGGACTCCAGACGTCC<br>TTGTGCAATCTCAGCTTGGTATGGTGTGTAGGGTGTGTACCATCCAGGAT<br>TTTCAATGACGTTGCGAAGT<br>ATGACAGGAGGAGTAATGGACTCGTAGTACCCCTGACCAATCATGCTTTT<br>TAGTACCTTGTTTCGCGCAC<br>CAAGAGAGCGCACGAGTGCGAGAGCATCCATCTCACTCATAGCCGCCACC<br>TCCGTCAAGGGTGGGCGTAC<br>AATATCCCCTGGAATAGCAGCCGTCATCAAATCAGAGAGACTCTCTTTTC<br>CAACCGTTCGAAGCATCGAC<br>ATTGTCTCAGCCGTTGTTGGACCAATATGGCGGTTAATATAGCTGTCCGT<br>GGCAGTCCATCGAACAAATG<br>TCACGCATGGCAAAGAGCCACGAAACAAACGACGGTACAT<br>(SEQ ID NO: 15) | |
| Alanine<br>Dehydrogenase | ATGATCATTGGCCTGCCGAAAGAGATCAAAGTTAAGGAAAACCGCGTGGC<br>ACTCACGCCCGGGGGCGTCG<br>CCAGCCTCGTGCGCCGGGCCACACCGTCATCGTGGAACGCAGCGCCGGC<br>GTGGGCAGCGGCATCCAGGA<br>CACCGAGTACGAGCAGGCCGGCGCGCAGCTCGGCAGCGCCGCCGAGGCGT<br>GGGCCGCGCAGATGGTCGTG<br>AAGGTCAAGGAGCCCATCAAGAGCGAATACGGGTACCTCCGCCCGGACCT<br>GCTGCTGTTCACGTACCTGC<br>ACCTCGCTGCGGACCAGCCCCTCACGGACGCCCTGCTGAGCGCCGGCACG<br>ACCGCCGTTGCGTACGAGAC<br>GGTGCAGCTCGACGACCGCAGCCTGCCGCTGCTCACGCCCATGAGTGAGG<br>TCGCGGGCCGCCTGAGCGTG<br>CAGGCCGGCGCGTACCACCTGCAAAAGCCCATCGGCGGGCGCGGCGTGCT<br>GCTCGGCGGCGTGCCGGGCG<br>TGCAGGCGGGCCACGTCGTCGTGATTGGCGGCGGCGTCGTCGGCACGAAC<br>GCCGCGAAAATGGCCATGGG<br>CCTCGGCGCGAAGGTCACGGTGCTGGACGTGAACCACGGGGCCCTCTCGT<br>ACCTCGACGACGTGTTCTTC<br>GGGAAGCTCACCACCATGATGAGCAACGAGGCGAACATCCGCTCCATCCT<br>GCCCGAAGCGGACCTCGTGA | YP_004171395.1<br>ADV67730.1<br>ADY25885.1<br>ADV48359.1<br>AFZ35471.1<br>AFZ05172.1<br>AEW05285.1<br>AEW04533.1<br>AEM70054.1<br>YP_005256957.1<br>YP_005256205.1<br>YP_004450492.1<br>YP_004368103.1<br>YP_004340432.1<br>YP_004261609.1<br>YP_004255502.1<br>YP_004163857.1<br>YP_004787476.1<br>YP_007132437.1<br>YP_007113588.1 |

TABLE 2-continued

| Enzyme | Gene Sequence | Accession Numbers |
|---|---|---|
| | TCGGCGGCGTGCTGATCCCCGGGGCGAAGGCGCCGCACCTTGTCACGCGC<br>GACATGCTGGCGACCATGCA<br>GGAAGGCAGCGTCATCGTCGACGTGGCGGTGGACCAGGGCGGATGCGTGG<br>AGACCATTCACGCGACGACG<br>CACGACGATCCCACGTACATCGTGGACGGCGTGATCCACTACGGCGTGGC<br>GAACATGCCGGGCGCGGTGC<br>CGCGCACCAGCACGTTCGCGCTCACGAACCAGACCATTGGGTACGTGCTG<br>CAGCTCGCGGACAAGGGCGT<br>GGAGGCACTCAGCGCCAGCAAGCCGCTGCTGCGTGGCCTGAACACCATCG<br>GCGGGAAGCTGACGTACGCG<br>GGCGTCGCGGAAGCGTTCGGCCTGACGTACACCGCGCCTGAAGTGGCGCT<br>GGCGTAA (SEQ ID NO: 16) | |
| Proline Dehydrogenase | ATGGAGCCCACTATGAGCCAATTCGAACAGCTGTACCGCCAGGTGGCCCT<br>CAGTGTCGCCGGCAACCCGG<br>TCGTGGAAAAAGTCTTGAGCAAGCAGGGCTGGGCGCTGGCGCAGCGTTTT<br>GTATCGGGCGAGACGGCGCA<br>GGACGCCATCAAGGCCATCAAGCGGCTGGAAGCCCAGGGCATCTCCGGCA<br>ACCTCGACCTGCTGGGCGAG<br>TTCGTGAACACCCCGGAACCCGCCAATGCCAACACCGAGATGATTCTGGC<br>GACCATTGACCAGGTGCACG<br>CGGCGGGCCTCACGCCCTACAACAGCGTGAAAATGTCGGCGCTGGGCCAA<br>GGGCAGACCGCGCCGGACGG<br>CCAGGACCTCGGCTACGTCAACACCCGCCGCGTCGTGGAGCGGGCCAAGC<br>GCTACGGCGGCTTCGTCAAT<br>CTGGACATGGAAGACCACACCCGCGTGGACTCGACTCTGCAGATTTTCCG<br>CCGCCTGGTCAAGGAGTTCG<br>GCCACCAGCATGTGGGAACGGTGTTGCAGGCCTACCTGCACCGCTCGGAA<br>GACGACCGCCGCAGCCTGGA<br>CGACCTGCGCCCCAACCTCCGCATGGTGAAGGGCGCCTACCTGGAGCCCG<br>CCTCCGTCGCCCTGCAGAGC<br>AAAACCGACATTGACGCCGCCTACCGCCGCCTGGTCTACGAGCACCTCAA<br>GGCCGGCAACTACTGCAACG<br>TGGCCACCCACGACCACCACATCATCTACGACGTGATGCACTTTGCGCTG<br>GCCCACGGCATCCCTAAGGA<br>CCAGTTCGAATTCCAGCTGCTGTACGGCATCCGCGAGGACCTGCAGCGCG<br>AATTGGCCGAGGCCGGCTAC<br>ACGGTGCGCTCGTACATTCCTTTCGGCAAGGACTGGTACGGCTACTACTC<br>GCGCCGCATCGCCGAGCGCC<br>CGCAGAACGTGATGTTCGTGCTGCGCGGCCTGCTGTAA<br>(SEQ ID NO: 17) | ADY26965.1<br>ADI14996.1<br>YP_004437470.1<br>YP_004368974.1<br>YP_004345744.1<br>YP_004340684.1<br>YP_004256582.1<br>YP_004170680.1<br>YP_003705539.1<br>AEA44906.1<br>AEB12864.1<br>ADV67015.1<br>AEE14339.1<br>AEA34625.1<br>EFH87253.1<br>NP_868270.1<br>ADQ16526.1<br>AEL26370.1<br>AFK04422.1<br>AEM71761.1 |
| Lysine Dehydrogenase | ATGAAAAACATTGTGGTTATCGGCGCGGGCAATATCGGTTCGGCAATCGC<br>CTGGATGCTGGCCGCATCAG<br>GCGATTATCGCATCACGGTTGCCGATCGTTCAGCCGATCAGCTGGCCAAT<br>GTGCCGGCGCATGAACGGGT<br>CGACATCGTCGACATTACCGACCGTCCCGCTCTGGAAGCACTGCTAAAAG<br>GCAAATTCGCCGTGCTCTCC<br>GCCGCCCCCACCGAATTCCACCTGACGGCGGGTATTGCCGAAGCGGCCGT<br>TGCCGTCGGCACGCATTATC<br>TCGATCTCACCGAAGACGTGGAATCCACCCGCAAGGTCAAGGCGCTGGCG<br>GAAACGGCCGAAACCGCGCT<br>CATTCCGCAATGCGGCCTCGCCCCCGGCTTCATCTCCATCGTCGCTGCCG<br>ATCTCGCCGTCAAGTTCGAC<br>AAGCTGGACAGCGTGCGCATGCGCGTCGGCGCTCTGCCGCAATATCCGTC<br>CAATGCGCTCAACTACAACC<br>TCACCTGGAGTACCGACGGGCTGATCAACGAATATATCGAGCCCTGCGAA<br>GGATTCGTCGAAGGCCGCCT<br>CACCGCCGTTCCGGCCCTTGAGGAGCGCGAGGAGTTCTCGCTCGATGGCA<br>TCACCTACGAGGCGTTCAAC<br>ACCTCGGGCGGTCTCGGTACGCTTTGCGCGACGCTGGAAGGCAAGGTGCG<br>GACCATGAACTACCGCACTA<br>TCCGTTATCCCGGCCATGTGGCGATCATGAAGGCGCTTTTGAACGACCTC<br>AACCTGCGCAACCGCCGCGA<br>TGTGCTGAAGGACCTGTTCGAAAACGCCCTGCCCGGCACCATGCAGGATG<br>TGGTCATCGTCTTCGTCACC<br>GTCTGCGGCACCCGCAACGGCCGCTTCCTGCAGGAAACCTATGCCAACAA<br>GGTCTATGCCGGCCCGGTTT<br>CCGGCCGGATGATGAGCGCCATCCAGATCACTACCGCCGCCGGCATCTGC<br>ACGGTTCTCGACCTGCTCGC<br>GGAAGGCGCCCTGCCGCAGAAGGGCTTCGTTCGACAGGAGGAAGTGGCGC<br>TGCCGAAGTTCCTCGAAAAC<br>CGGTTTGGCCGGTATTATGGCTCGCATGAGCCGCTGGCGCGGGTTGGGTG<br>A (SEQ ID NO: 18) | BAH80102.1<br>AAV93559.1<br>YP_165503.1<br>AIA01810.1<br>AIA03878.1<br>AIA03381.1<br>AIA00889.1<br>EXU92064.1<br>EOT00338.1<br>NP_882461.1<br>EIJ80893.1<br>AIA06975.1<br>AIA05885.1<br>EXU88317.1<br>EOT04629.1<br>AIA07859.1<br>AIA04644.1<br>AIA04440.1<br>AIA03522.1<br>AIA02686.1 |

The disclosure relates to an ammonia or ammonium ion biosensor for measuring a total concentration of ammonia in blood. The ammonia biosensor may comprise, in some embodiments, a measuring electrode which include as components, a mediator and an enzyme, which selectively act on the plurality of specific amino acids each serving as a substrate, and a counter electrode. In the amino-acid biosensor, the enzyme has a substrate affinity to each of the plurality of specific amino acids. The enzyme is operable to catalyze a reaction in each of the plurality of specific amino acids as a substrate so as to form a reaction product. The mediator is operable, during amino-acid concentration measurement, to carry electrons between the reaction product and the measuring electrode. Further, the amino-acid biosensor is designed to apply a voltage between the measuring electrode and the counter electrode at a measurement point in such a manner that, in an analytical curve representing a relationship between an applied voltage and a current value in a specific concentration for each of the plurality of specific amino acids, the applied voltage is a voltage allowing the variety of the current values for the amino acids in the same concentration and at the same applied voltage.

In some embodiments, the measuring electrode (at least a first electrode) further comprises a a hydrogel that comprises a coenzyme or reduction agent as a component. In some embodiments, the enzyme consists of a dehydrogenase. Further, the reaction product consists of a reduced coenzyme derived by reduction of the coenzyme, and the mediator is operable, during the amino-acid concentration measurement, to carry electrons from the reduced coenzyme to the measuring electrode.

The disclosure also relates to a system comprising the biosensors disclosed herein and a computer processor and a display. In some embodiments, the disclosure relates to a computer-implemented method of quantifying ammonia concentration in a sample, for example, a light detector such as a CMOS camera as disclosed in PCT/US2015/026546, which is included herein by reference in its entirety.

In some embodiments, a biosensor or system disclosed herein is used in conjunction with one or a combination of the following:

1. a power source in electrical connection with the electrodes and capable of supplying an electrical potential difference between the electrodes sufficient to cause diffusion limited electro-oxidation of the reduced form of the mediator at the surface of the working electrode; and 2. at least one meter, (such as a spectrophoteomter, voltmeter and/or amperometer) in electrical connection with the electrodes and capable of measuring the diffusion limited current produced by of the reduced form of the mediator with the above-stated electrical potential difference is applied.

The meter will normally be adapted to apply an algorithm to the current measurement, whereby an ammonia or ammonium ion concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby expressly incorporated by reference.

Ammonia or ammonium ion concentrations from a plurality of samples may be analyzed in parallel. For example, human and non-human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured by placing multiple test strips in a device disclosed herein at one time. Fluid preparations of tissues from humans and non-human animals can also be assayed, along with foods, water samples, fermentation products and environmental substances, which potentially contain environmental contaminants. In some embodiments, human serum is assayed with the disclosed biosensor. In some embodiments, the biosensor comprises or is configured to assay whole blood. In some embodiments, the term sample specifically excludes samples from a subject and refers to foods, water samples, fermentation products and environmental substances, which potentially contain environmental contaminants.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the at least one mediator at the surface of the working electrode. In some embodiments, the working electrode comprises a hydrogel disclosed herein. A current measuring meter (not shown) measures the diffusion-limited current generated by the oxidation of the reduced form of the mediator at the surface of the working electrode. The measured current may be accurately correlated to the concentration of ammonia or ammonium ion and/or one or more amino acids in sample when the following requirements are satisfied:

1. The rate of the indophenol reaction based upon the concentration of indophenol reagents is governed by the rate of diffusion of the ammonia from the sample in a first vessel to the second vessel comprising a surface of the working electrode.

To manufacture biosensor a roll of metallized film is fed through guide rolls into an ablation/washing and drying station. A laser system capable of ablating bottom plate element 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in a pre-determined pattern, to form a ribbon of isolated electrode sets. The metallized film is further ablated, after the isolated electrode sets are formed to create recesses positioned adjacent the electrochemical area. The ribbon is then passed through more guide rolls, with a tension loop and through an optional inspection camera. The camera is used for quality control in order to check for defects.

Reagent is compounded and may be applied in a liquid form to the center of one or more vessels or electrochemical area at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to the biosensor, chip, test strip, or solid support disclosed herein in a liquid or other form and dried or semi-dried onto the center of the electrochemical area in accordance with this disclosure. If using liquid reagents, the liquid reagent may be stored in a sealed or unsealed storage vessel such that volume of reagents (anywhere from about 1 microliter to about 100 microliters) may be attached or part of the surface of the biosensor, chip, test strip, or solid support. If sealed, the seal prevent mixing of any of the indophenol reagent prior to introduction of the sample to the biosensor, chip, test strip, or solid support. If sealed, the biosensor, chip, test strip, or solid support may comprises a means to break or puncture or otherwise disrupt the seal so that fluid contents of the storage vessel can use a fluid path to the first or second vessel (a part of the reaction vessel). In some embodiments, the sealed storage vessels are blisterpacks. In some embodiments, the sealed storage vessels are blisterpacks with a portion of the seal adjacent to or substantially proximate to a conduit through which liquid phase reagents may flow to the reaction vessel upon breaking the seal. In some embodiments, reagents in solid phase may be placed in a regent storage vessel or in the reagent conduit itself, whereby by liquid phase indophenol reagents may be mixed with solid phase indophenol reagents upon rupture, breakage or disruption of any seals holding back fluid flow in the fluid circuit.

In some embodiments, the biosensor, system, chip, test strip, or solid support disclosed herein comprises the following indophenol reagents in solid or liquid form: a hyophalite, an alkali buffer, a phenolic reagent, and a catalyst. In some embodiments, the biosensor, chip, test strip, or solid support may comprise two alkali buffers sodium acetate and sodium hydroxide in liquid phase (at concentrations from about 1 µM to about 1 M each) in individual reagent storage vessels. In some embodiments, the biosensor, chip, test strip, or solid support may comprise the hypohalite in liquid phase within a reagent storage vessel.

In some embodiments, the indophenol reagents, such as the phenolic reagent and the catalyst are stored in solid phase. The disclosure relates to the placement of solid phase indophenol reagents in vessels or conduits with in the fluid circuit so that the biosensor, chip, test strip, or solid support may stored for long periods of time. If some solid phase reagents are used, the biosensor, chip, test strip, or solid support may be stored for no fewer than about 50, 75, 100, 125, 150, 175, 200, 225, or about 245 days at room temperature or below. In some embodiments, room temperature is from about 60 to about 80 degrees Fahrenheit. In some embodiments, room temperature is about 70 degrees Fahrenheit. In some embodiments, storage of the reagents in solid phase allows for longterm storage of the biosensor, chip, test strip, or solid support for no fewer than about 50, 75, 100, 125, 150, 175, 200, 225, or about 245 days at or below 0 degrees Celsius.

In addition, a roll or top plate element material is fed into an assembly station along with a roll of spacer material. Liners on either side of the spacer material are removed in that station and the top plate element or surface scaffold is applied to one side of the spacer material to form a top plate element/spacer subassembly. The top plate element/spacer subassembly is slit into the appropriate width for a row of biosensors. Next, a new release liner is added to the side of the spacer material opposite the cover and the subassembly is wound into a roll.

The ribbon of the reagent-coated bottom plate element is unwound and fed into a sensor assembly station along with the top plate element/spacer subassembly. The liner is removed from the spacer and the subassembly is placed on bottom plate element to cover reagent. Next, the assembled material is cut to form individual biosensors, which are sorted and packed into vials, each closed with a stopper, to give packaged sensor test strips.

Although ablating recesses is described herein, it is appreciated that the method of forming recesses in bottom plate element is also not limited. For example, the recesses may be formed by etching (e.g., using photoligographic methods) or otherwise removing a portion of the surface of top plate element. The nearest electrode edge is approximately about 10 µm to about 500 µm from the recess, or about 100 µm to about 400 µm from the recess, or from about 200 µm to about 300 µm from the recess. Biosensors that are formed with recesses in accordance with this disclosure yield a reagent profile with generally uniform thickness of chemistry. A generally uniform thickness of chemistry allows for more accurate sample analysis.

The processes and products described above include a disposable biosensor, especially for use individually as a diagnostic device or in combination with other components such as a pump system or spectrophotometer configured to diagnose hyperammonemia, abnormal function, or abnormally high or low amounts of ammonia in a sample. in some embodiments, the system disclosed herein comprises a unit configured to receive the biosensor, chip, test strip, or solid support disclosed herein such that insertion of the biosensor, chip, test strip, or solid support into the unit aligns the microfluidic pathways to channels on the unit, whereby a sample may be introduced to the biosensor, chip, test strip, or solid support while nested in the unit and readings from detection equipment, such as a spectrophotometer, may be positioned at near or substantially near a detection vessel such that measurements within the detection vessel may be taken and sent digitally to a display that provides an operator with a reading of how much ammonia is in the sample. In such embodiments, an operator may engage a microneedles or other means of breaking seals of reagent storage vessels so that liquid phase and solid phase indophenol reagents may mix with a sample in the fluid circuit for a sufficient time to complete an indophenol reaction. After the reaction is complete and a reading is sent to a display for the operator, the biosensor, chip, test strip, or solid support may be removed from the detection unit and disposed of. The unit may be re-used as necessary to accept a plurality of biosensor, chip, test strip, or solid supports disclosed herein.

Variations on the Indophenol Reaction

The disclosure relates to contacting a sample with one or a plurality of reagents in independently variable phases of dried, powdered or aqueous phases. The reaction has four major components: a compound comprising a phenyl group (or phenolic reagent), a hypohalite, a catalyst and an alkali buffer. When these reagents are exposed to ammonia, an indophenol compound is produced that, when exposed to a light source at a particular wavelength, absorbs and/or emits a particular wavelength of light. In some embodiments, any of the methods disclosed herein make comprise a step of detecting the presence, absence, or quantity of ammonia or ammonium ion by measuring the absorbance of the contents of indophenol reaction products at the first vessel or the second vessel, or the detection vessel.

Family of Phenols or Phenolic Reagents

Different compounds comprising a phenyl group can be used as long as the compound comprises a 4, 5, or 6-membered ring with at least one carbon atom and a unsubstituted 'para-position.'

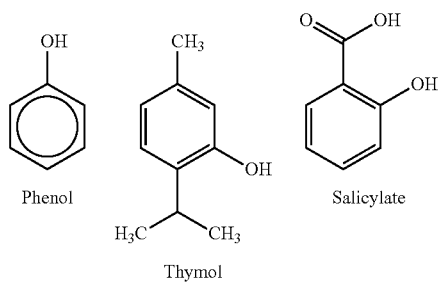

Phenol     Thymol     Salicylate

-continued

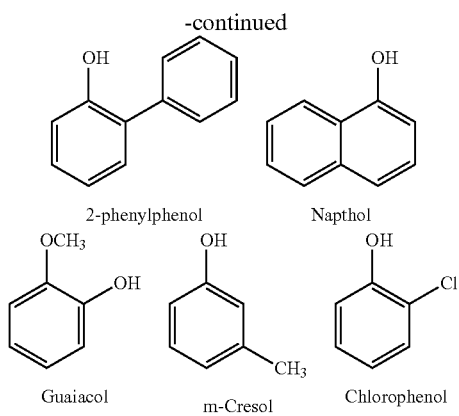

2-phenylphenol
Napthol
Guaiacol
m-Cresol
Chlorophenol

Family of Hypohalites

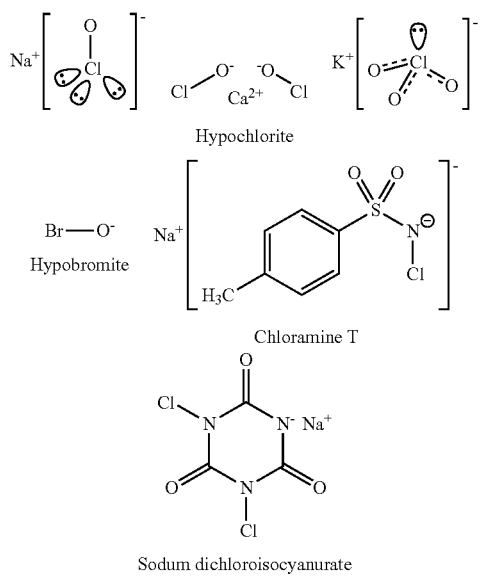

Hypochlorite

Hypobromite

Chloramine T

Sodum dichloroisocyanurate

Family of Catalysts/Coupling Agents

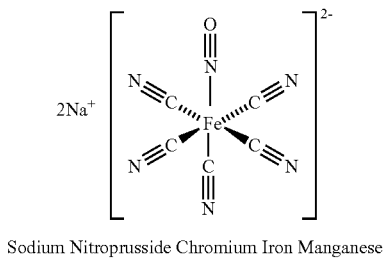

Sodium Nitroprusside Chromium Iron Manganese

Alkali Conditions

Any buffer capable of creating an alkali microenvironment for the reaction to take place with ammonia from a sample may be used. In some embodiments, a vessel comprising an alkali buffer with pH from about 8.5 to about 13 can be used in the biosensor, test strip, or system disclosed herein. Any compound that can create these alkali conditions can be used including sodium and potassium hydroxide, or sodium or potassium acetate. In some embodiments, the alkali buffer is in a powdered form, lyophilized, or aqueous solution in a vessel located within the biosensor or kit disclosed herein.

Electrode

In some embodiments, the biosensor, system or test strip disclosed herein comprise one or more electrodes. In some embodiments, the one or more electrodes transmit current variation generated by the reaction between the indophenol reagents and ammonia or ammonium ion from a sample and/or transmit current variation generated by a battery source to the light source or other equipment necessary to provide a readout of the levels of ammonia in a sample, for instance, in the case of a spectrophotometer to measure absorbance of a reactant vessel in the biosensor. In some embodiments, the electrodes comprise metal. In some embodiments, the electrodes comprise a carbon scaffold upon which a metal is deposited. In some embodiments, the electrodes comprise a carbon scaffold of carbon nanotubes.

Electrode structures which are suitable for the present disclosure and methods for the production of such structures have already been suggested in biosensor technology for other purposes. In this regard, reference is made to U.S. Pat. No. 6,645,359 and its content is incorporated herein by reference in its entirety. Electrodes or Electrically conductive tracks are created or isolated on first surface. Tracks represent the electrodes of biosensor. As used herein, the phrase "electrode set" is a set of at least two electrodes, for example 2 to 200, or 3 to 20, electrodes. These electrodes may, for example, be a working (or measuring) electrode and an auxiliary electrode. In some embodiments, tracks cooperate to form an interdigitated electrode array positioned within the periphery of recesses and leads that extend from array and between recesses toward end.

Tracks are constructed from electrically conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. In some embodiments, the track is a working electrode made of silver and/or silver chloride, and track is an auxiliary electrode that is also made of silver and/or silver chloride and is substantially the same size as the working electrode.

Tracks are isolated from the rest of the electrically conductive surface by laser ablation. Techniques for forming electrodes on a surface using laser ablation are known. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks are preferably created by removing the electrically conductive material from an area extending around the electrodes. Therefore, tracks are isolated from the rest of the electrically-conductive material on a surface by a gap having a width of about 5 µm to about 500 µm, preferably the gap has a width of about 100 µm to about 200 µm. Alternatively, it is appreciated that tracks may be created by laser ablation alone on bottom substrate. Further, tracks may be laminated, screen-printed, or formed by photolithography.

Multi-electrode arrangements are also possible in accordance with this disclosure. For example, it is contemplated that a biosensor may be formed that includes an additional electrically conductive track. In a three-electrode arrangement, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode. It is appreciated that the number of tracks, as well as the spacing between tracks in array may vary in accordance with this disclosure and that a number of arrays may be formed as will be appreciated by one of skill in the art. in some embodiments, the electrodes are embedded on or attached to a solid support, such as a test strip comprising a plastic and/or paper material.

Micro-electrode arrays are structures generally having two electrodes of very small dimensions, typically with each electrode having a common element and electrode elements or micro-electrodes. If "interdigitated" the arrays are arranged in an alternating, finger-like fashion (See, e.g., U.S. Pat. No. 5,670,031). These are a sub-class of micro-electrodes in general. Interdigitated arrays of micro-electrodes, or IDAs, can exhibit desired performance characteristics; for example, due to their small dimensions, IDAs can exhibit excellent signal to noise ratios.

Interdigitated arrays have been disposed on non-flexible substrates such as silicon or glass substrates, using integrated circuit photolithography methods. IDAs have been used on non-flexible substrates because IDAs have been considered to offer superior performance properties when used at very small dimensions, e.g., with feature dimensions in the 1-3 micrometer range. At such small dimensions, the surface structure of a substrate (e.g., the flatness or roughness) becomes significant in the performance of the IDA. Because non-flexible substrates, especially silicon, can be processed to an exceptionally smooth, flat, surface, these have been used with IDAs. In some embodiments, the at least one electrode is a component of any IDA disclosed herein.

Membrane

In some embodiments, the membrane positioned at a fluid exchange opening comprises an ionomer. In some embodiments, the membrane comprises one or a combination of the following polymers:

1.

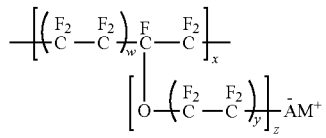

2.

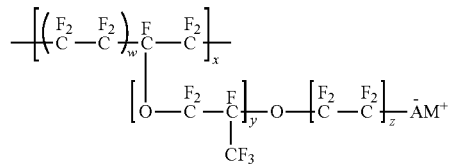

3.

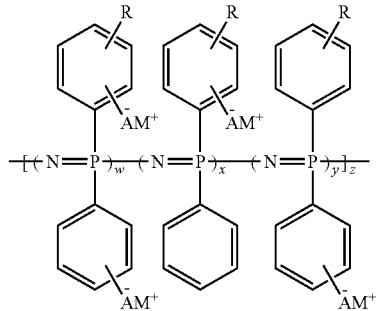

4.

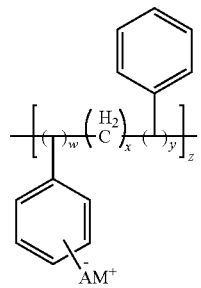

5.

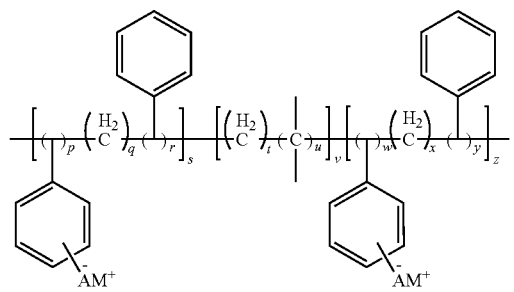

6.

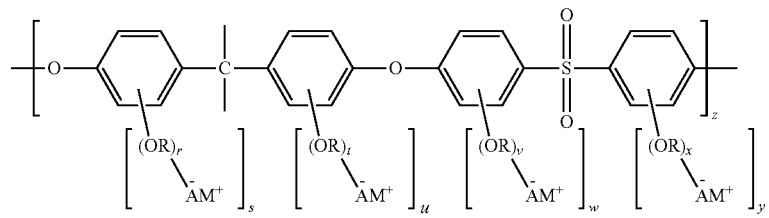

wherein each of the variables p, q, r, s, t, u, v, w, x, y, and z are independently variable and are 0 or any positive integers; and wherein R is independently selected from an amine, hydroxy, hydroxyl, carbonyl, H, =O, —OH, —COOH, —N, —CH$_3$, —CH$_2$—X, halo, aryl, arylalkoxy, arylalkyl, alkynyl, alkenyl, alkylene, alkyl, akyl-halo, arylamido, alkylheterocycle, alkylamino, alkylguanidino, alkanol, alkylcarboxy, cyclo alkyl, heteroaryl, heteroarylalkyl, heteroarylalkoxy, or heterocyclyl; or any salt thereof. In some embodiments, the variables p, q, r, s, t, u, v, w, x, y, and z are independently variable and are 0 or about 100, 1000, 10000, or 100000 or more whereby, optionally, a manufacturer may form long micrometer width sheets of polymer that can sover a width of a vessel from about 1 to about 1000 microliters in diameter.

In some embodiments, the R group is acidic or an electronegative substituent. In some embodiments, the variables p, q, r, s, t, u, v, w, x, y, z are independently variable and are 0 or positive integers from about 1 to about 200. In some embodiments, the variables p, q, r, s, t, u, v, w, x, y, z are independently variable and are 0 or positive integers from about 10 to about 100. In some embodiments, the variables p, q, r, s, t, u, v, w, x, y, z are independently variable and are 0 or positive integers from about 10 to about 100 across many species within a matrix of material comprising many species of polymer. A– represents the anionic or acidic groups that can include sulfonate, carboxylate, or other similar functional group. M+ represents the counter ion and may include H+, Li+, Na+, or similar cation. Letters (p-z) accompanied by parenthesis or brackets represent repeat units that can range from 0 to any integer value. Any polymer containing any combination of Carbon (C), Fluorine (F), Sulfur (S), Oxygen (O), Hydrogen (H), Nitrogen (N), Phosphorous (P), or any similar element, which may be used to create an ionic exchange membrane may also be utilized.

Ion exchange membranes can be constructed from polymers including perfluorinated ionomers (1&2), polyphosphazene based ionomers (3), polystyrene based ionomers (4), polystyrene based block-co-polymer ionomers (5), and poly(arylene ether sulfone) based ionomers (6).

Total acid content for ionic exchange membranes may range from about 0.57 to about 3.5 meq/g. In some embodiments, the total acid content for ionic exchange is from about 0.57 to about 4.0 meq/g. In some embodiments, the total acid content for ionic exchange is from about 0.57 to about 3.0 meq/g. In some embodiments, the total acid content for ionic exchange is from about 0.57 to about 2.9 meq/g. In some embodiments, the total acid content for ionic exchange is from about 0.57 to about 2.8 meq/g. In some embodiments, the total acid content for ionic exchange is from about 0.57 to about 2.7 meq/g. In some embodiments, the total acid content for ionic exchange is from about 0.57 to about 2.6 meq/g. In some embodiments, the total acid content for ionic exchange is from about 0.57 to about 2.5 meq/g. In some embodiments, the total acid content for ionic exchange is from about 0.57 to about 2.4 meq/g. In some embodiments, the total acid content for ionic exchange is from about 0.57 to about 2.3 meq/g. In some embodiments, the total acid content for ionic exchange is from about 0.57 to about 2.2 meq/g. In some embodiments, the total acid content for ionic exchange is from about 0.57 to about 2.1 meq/g. In some embodiments, the total acid content for ionic exchange is from about 0.57 to about 2.0 meq/g.

Membranes constructed from these ionomers may range in thickness from about 0.025 to about 0.69 mm in thickness. In some embodiments the membrane is from about 0.001 to about 069 mm in thickness. In some embodiments the membrane is from about 0.001 to about 068 mm in thickness. In some embodiments the membrane is from about 0.001 to about 067 mm in thickness.

In some embodiments the membrane is from about 0.001 to about 066 mm in thickness. In some embodiments the membrane is from about 0.001 to about 065 mm in thickness. In some embodiments the membrane is from about 0.001 to about 064 mm in thickness. In some embodiments the membrane is from about 0.001 to about 063 mm in thickness. In some embodiments the membrane is from about 0.001 to about 062 mm in thickness. In some embodiments the membrane is from about 0.001 to about 061 mm in thickness. In some embodiments the membrane is from about 0.001 to about 060 mm in thickness. In some embodiments the membrane is from about 0.001 to about 059 mm in thickness. In some embodiments the membrane is from about 0.001 to about 058 mm in thickness. In some embodiments the membrane is from about 0.001 to about 050 mm in thickness. In some embodiments the membrane is from about 0.001 to about 040 mm in thickness. In some embodiments the membrane is from about 0.001 to about 030 mm in thickness. In some embodiments the membrane is from about 0.001 to about 020 mm in thickness. In some embodiments the membrane is from about 0.001 to about 010 mm in thickness. In some embodiments the membrane is from about 0.025 to about 065 mm in thickness. In some embodiments the membrane is from about 0.025 to about 064 mm in thickness. In some embodiments the membrane is from about 0.025 to about 063 mm in thickness. In some embodiments the membrane is from about 0.025 to about 062 mm in thickness. In some embodiments the membrane is from about 0.025 to about 061 mm in thickness. In some embodiments the membrane is from about 0.025 to about 060 mm in thickness. In some embodiments the membrane is from about 0.025 to about 059 mm in thickness. In some embodiments the membrane is from about 0.025 to about 058 mm in thickness. In some embodiments the membrane is from about 0.025 to about 050 mm in thickness. In some embodiments the membrane is from about 0.025 to about 040 mm in thickness. In some embodiments the membrane is from about 0.025 to about 030 mm in thickness. In some embodiments the membrane is from about 0.025 to about 020 mm in thickness. In some embodiments the membrane is from about 0.025 to about 010 mm in thickness.

Higher total acid content and smaller membrane thickness leads to faster diffusion times. Membranes may be formed through extrusion casting, drop casting, hot pressing, or similar method.

Cartridges and Disposable Devices

The biosensor, device, system, and or test strip may be or comprise a cartridge. In some embodiments, the cartridge is disposable after one use or can be used more than once per ammonia or ammonium ion detection event. In some embodiments, the cartridge comprises a plurality of microfluidic conduits in fluid communication with a storage portion, a mixing portion and a readout portion of the cartridge. The storage portion comprises a plurality of compartments that store one or a combination of indophenol reagents either crystallized, dried, lyophilized or in solution. In some embodiments, the compartments may be partitioned from an adjacent conduit by plastic wall or other inert material. The mixing portion of the cartridge comprises a trunk-shaped conduit where one or more reagents being stored mix after they are released from the storage portion of the device. The reagents may mix with a sample and/or each other at different points in the microfluidic channels adjacent to the storage portion of the device. In some embodiments of the device the readout portion of the microfluidic conduits is adjacent to the mixing portion of the device. In some embodiments of the device, the cartridge comprises only a storage portion and a readout portion, wherein the readout portion comprises a microfluidic conduit configured to align to an instrument that measures the amount of ammonia or ammonium in a sample but also allows mixing of samples prior to any detection or quantification step takes place through the instrument. In some embodiments, the cartridge does not comprise an instrument for detection of the amount of ammonia or ammonium ion in an sample (spectrophotometer), but is configured to align the readout portion of the cartridge to a instrument capable of determining the amount of ammonia or ammonium ion in a sample. In some embodiments, the cartridge comprises an instrument for detection of the amount of ammonia or ammonium ion in an sample, such as a photodiode. In some embodiments, the cartridge comprises readout portion comprising microfluidic conduits for detection or quantification adjacent to the mixing portion of the device. In some embodiments, the cartridge comprises an instrument for detection of the amount of ammonia or ammonium ion in an sample, such as a photodiode, such instrument comprising a light source aligned to or with the readout portion of the device such that light from the light source may penetrate the readout portion and such instrument may detect the presence, absence or absorbance of wavelength of light in the readout portion.

In some embodiments, the cartridge comprises a microfluidic circuit comprising a storage portion in fluid communication with a mixing portion which is also in fluid communication with a readout portion. Fluid in such an embodiment is designed to flow from the storage portion to the mixing portion, and from the mixing portion to the readout portion of the cartridge. In some embodiments the storage portion comprises one compartment or vessel for each indophenol reagent. In some embodiments, the storage portion comprises a first compartment comprising a hypohalite (such as hypochlorite), a second compartment comprising an basic buffer (such as NaOH), and a third compartment comprising at least one indophenol reagent or indophenol related compound (such as 2-phenylphenol). In some embodiments, the storage portion comprises a fourth compartment comprising a catalyst or coupling reagent (such as Sodium Nitroprusside). In some embodiments, the storage portion comprises a fifth compartment comprising an alkali buffer (such as sodium acetate or calcium acetate or zinc acetate). In some embodiments, the cartridge comprises a fluid exchange opening between a microfluidic conduit the compartment comprising a an alkali buffer (such as sodium acetate or calcium acetate or zinc acetate). In some embodiments, a membrane disclosed herein is positioned over at least a portion of the fluid exchange opening such that when a sample comes in contact with the alkali buffer, ammonia can be transported from the first vessel across the membrane into the second vessel or adjacent microfluidic conduit.

In some embodiments, the storage portion comprises a compartment optionally comprising an electrode. In some embodiments the compartment optionally comprising an electrode is adjacent to a compartment comprising the alkali buffer in solid or liquid phase, such compartment having an opening through which a sample may be deposited into the cartridge from a point exterior to the cartridge. In some embodiments, the cartridge comprises a sixth compartment comprising an opening and optionally comprising an electrode, such compartment having an opening through which a sample may be deposited into the cartridge from a point exterior to the cartridge. In some embodiments, the cartridge comprises a sixth compartment comprising an opening and optionally comprising an electrode, such compartment having an opening through which a sample may be deposited into the cartridge from a point exterior to the cartridge; wherein the cartridge further comprises a a compartment comprising an alkali buffer that is positioned at or substantially near the compartment comprising the opening, such that, upon inserting a sample into the compartment with an opening, the alkali buffer is transported to the compartment comprising the opening and mixes with the sample.

In some embodiments, a compartment has a volume of no more than about 100 microliters of fluid. In some embodiments, one or more compartments in the cartridge has a volume of no more than about 100 microliters of fluid. In some embodiments, one or more compartments in the cartridge has a volume of no more than about 90 microliters of fluid. In some embodiments, one or more compartments in the cartridge has a volume of no more than about 80 microliters of fluid. In some embodiments, one or more compartments in the cartridge has a volume of no more than about 70 microliters of fluid. In some embodiments, one or more compartments in the cartridge has a volume of no more than about 60 microliters of fluid. In some embodiments, one or more compartments in the cartridge has a volume of no more than about 50 microliters of fluid. In some embodiments, one or more compartments in the cartridge has a volume of no more than about 40 microliters of fluid. In some embodiments, one or more compartments in the cartridge has a volume of no more than about 30 microliters of fluid. In some embodiments, one or more compartments in the cartridge has a volume of no more than about 20 microliters of fluid. In some embodiments, one or more compartments in the cartridge has a volume of no more than about 10 microliters of fluid.

FIG. 1 depicts a photograph of 3D printed modular pieces snapped together around Nafion to form a bisected well. A bisected well containing blood in one section and a concentrated alkali solution in the other would provide a means for cation exchange of the whole blood to occur, yielding a strong recovery of the ammonium. A computer-aided design of the well that is both reusable and modular was 3D printed. As seen in FIG. 1, two modular pieces were 3D printed from acrylonitrile-butadiene-styrene thermoplastic. The pieces will snap together with the membrane in the middle, forming a Nafion bisected well. This design was chosen to provide a uniform platform for all future experiments involving this sensing mechanism. Silicone gasketing material, at a 1/64" thickness, was glued to the inner face of each well-half to ensure a water tight seal. The wells were then back-filled with polydimethylsiloxane to improve their mechanical properties.

Figure 2:
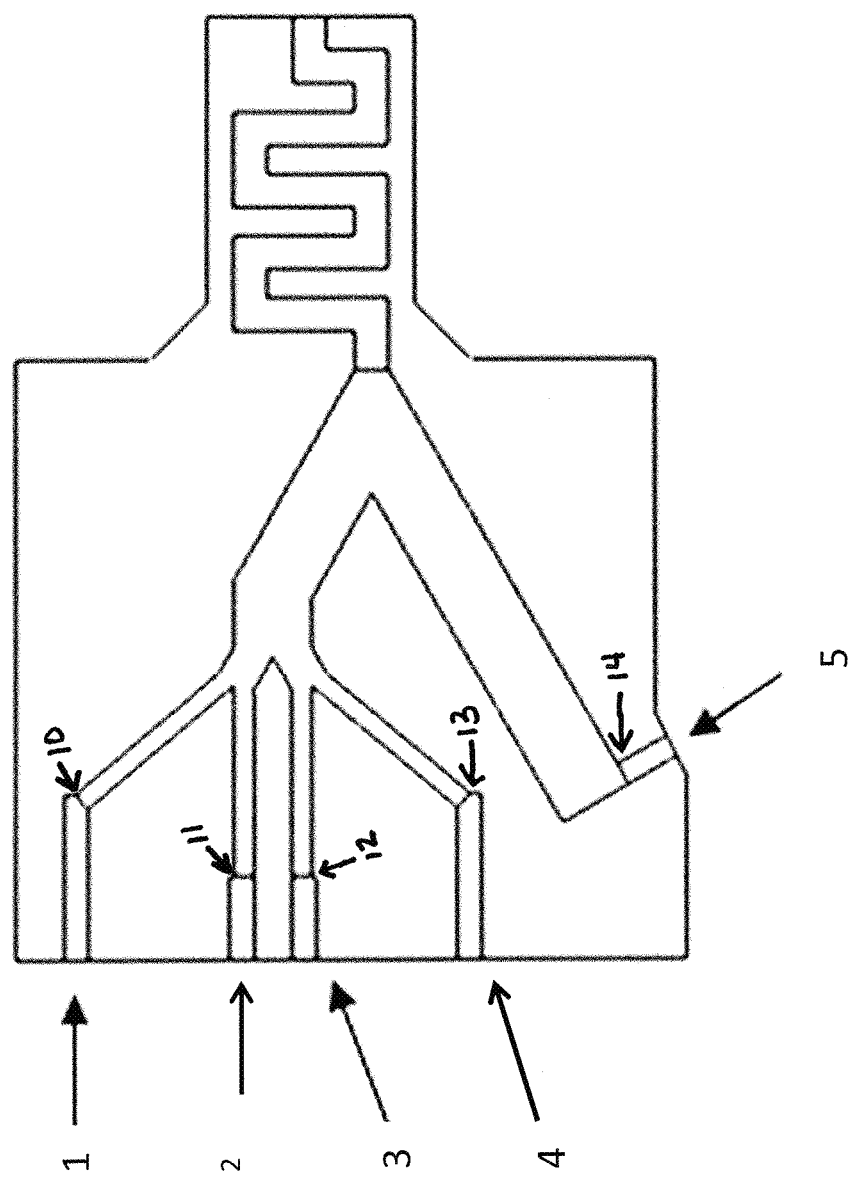
FIG. 2 depicts a CAD sketch of the top piece of a disposable cartridge, with dimensions in mm. Channels 1 through 5 are labeled.
Figure 3:
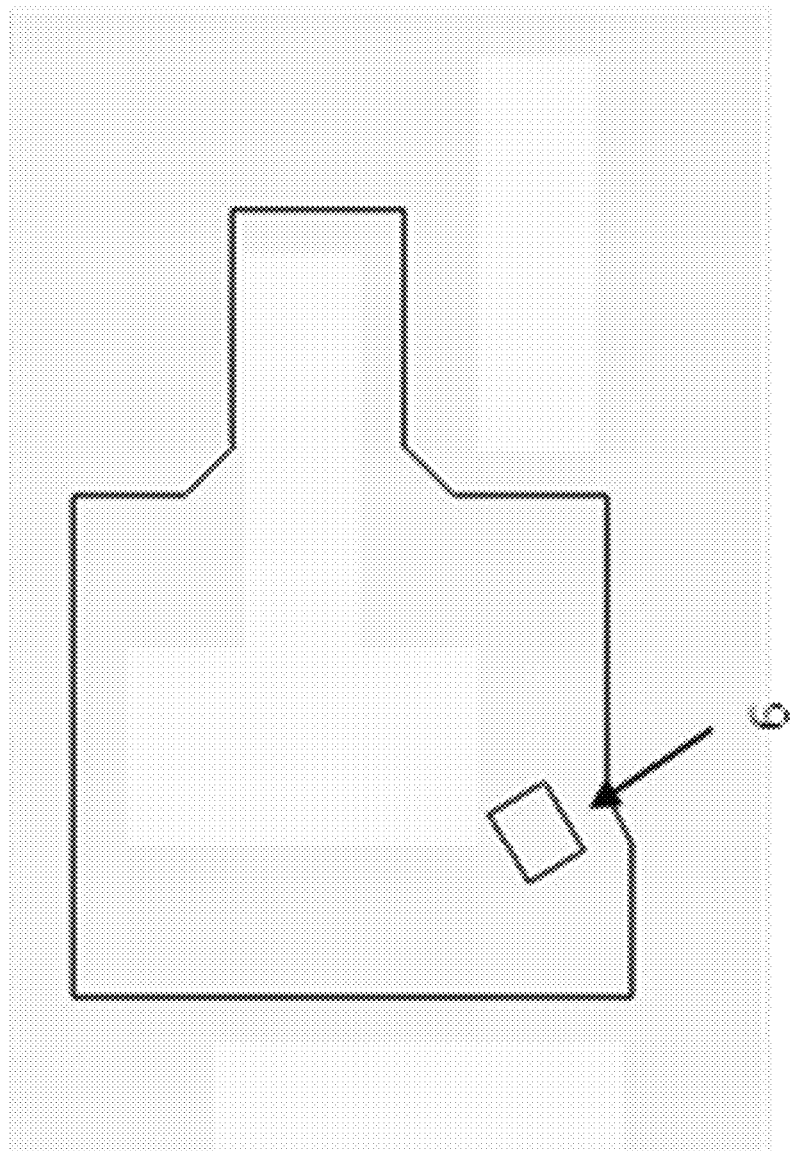
FIG. 3: CAD sketch of the bottom piece of the chip with channel 6 labeled.
Figure 4:
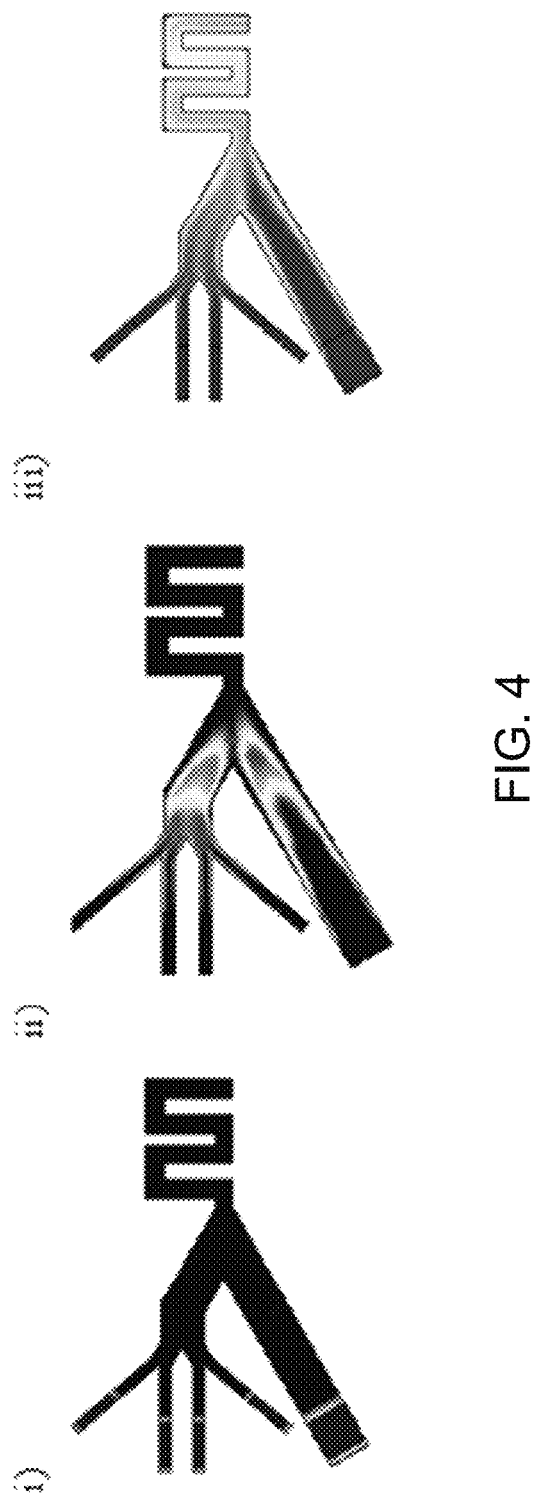
FIG. 4: depicts the representations of a concentration profile at i) t=0 seconds (s); ii) t=13 s, and iii) t=24 s after a whole blood sample in 40 microliters is loaded into well number 6.

FIGS. 2 through 4 depict an embodiment of the disclosure that is a cartridge. One half of the cartridge is depicted in FIG. 2 while the opposite facing half of the cartridge is depicted in FIG. 3. The two halves of the cartridge may be secured together by one or a plurality of micrscrews, dowels or fasteners. The two halves of the cartridge may be made out of one or a plurality of inert materials such as a plastic and/or glass.

The cartridge half disclosed in FIG. 2 comprises a first, second, third, fourth and fifth storage compartment. FIG. 2 depicts a first, second, third, fourth and fifth compartment (labeled 1, 2, 3, 4, and 5 respectively) that define a volume immediately adjacent to, but partitioned from, a microfluidic conduit on a bottom half of the cartridge. The partition is delineated by the small solid dash bisecting the space between the compartment and the microfluidic conduit (labeled 10, 11, 12, 13, and 14 for each of the compartments 1, 2, 3, 4, and 5 respectively. In this embodiment, the first compartment comprises hypohalite, the second compartment comprises an basic buffer, the third compartment comprises a catalyst, the fourth compartment comprises a indophenol reagent (such as a phenolic compound), and the fifth compartment comprises an alkali buffer, which, if in aqueous solution, may be at a concentration from about 500 mM to about 1 M sodium acetate. The storage portion of the microfluidic circuit comprises the storage points 1, 2, 3, 4, 5, and 6. Any membrane disclosed herein may be placed at or near position 14 such that, upon introduction of a sample such as whole blood in the compartment 6 of FIG. 3, mixing of the reagents can occur. Fluid from compartment 5 is mixed with the sample and ammonia ions in solution may be transferred from 5 and 6 into the mixing portion of the device 20 across the membrane. The reagents in compartments 1 through 4 are also released such that after a period of about 4-5 seconds, all reagents have entered the mixing portion of the device 20. The upper branched portion of the mixing portion 20 mixes the indophenol reagents contained in the compartments 1, 2, 3 and 4 while the ammonia from the sample and to buffer in 5 and 6 mix in the lower trunk of the cartridge. Once in use, FIG. 4 depicts the anticipated flow of fluid from each compartment to the mixing portion of the cartridge. Lighter shades of grey show the bolus of reagents from each compartment as they travel at 0 seconds (i); at 13 second (ii); and 24 seconds (iii) through the microfluid circuit. After mixing is complete in the mixing portion of the device, all reagents mix in the portion of the mixing portion closest proximate to the readout portion 25 of the circuit. At the readout portion of the device, the cartridge may have an opening though which light may travel and expose the fluid to a certain measurable wavelength of light. An instrument such as a photodiode may be present near or adjacent to the readout portion of the device so that measurements of absorbance may be taken.

Figure 5A:
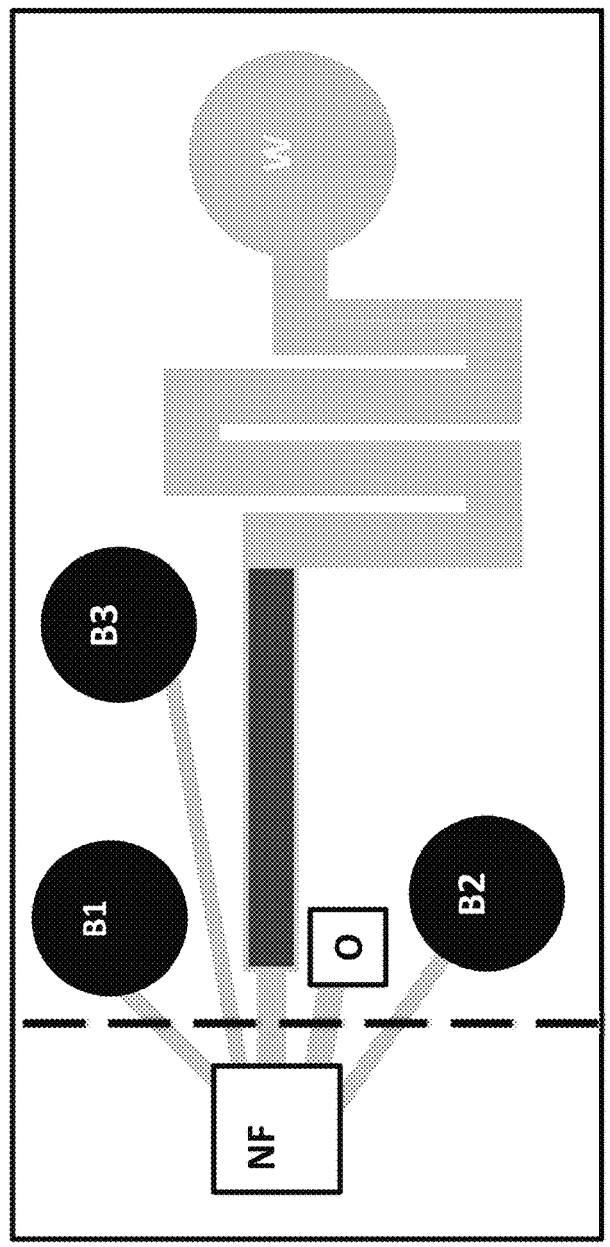
FIGS. 5A and 5B depict a disposable cartridge with reagents contained in blister packs and a reader.
Figure 5B:
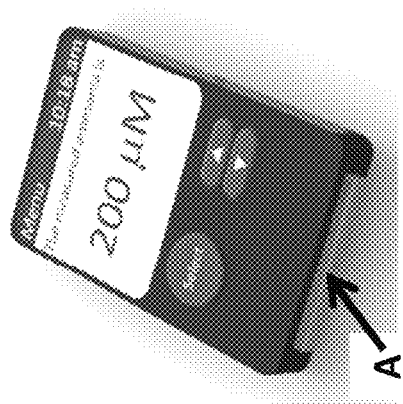

FIGS. 5A and 5B depict an embodiment of the disclosure that is another type of cartridge. As shown in FIG. 5A, the cartridge will comprise 2-3 blister packs of reagents, with B1, B2, and B3 indicating blister pack placement. The chamber labeled NF is the Nafion membrane and chamber that will take in the blood sample. The chamber labeled O is the overflow chamber for excess sample. The light grey regions are channels by which the liquid reagents can move, with the circle W being the read-out well. The dark grey region indicates placement of dried reagents, for example, sodium nitroprusside and 2-phenylphenol, which are more stable as dried powered then in liquid or suspended form.

The cartridge in FIG. 5A comprises 2-3 blister packs. The blister pack for sodium hypochlorite and sodium hydroxide could be combined into one blister pack. The blister packs can have a volume ranging from 5-50 microliters. The region on the chip to the left of the dotted line would sit outside the measurement device once inserted while the region to the right would sit inside the measurement device. A blood sample of a volume of 5-100 microliters would be inserted into the a container on the device by either pipette, capillary action or mechanical action. The Nafion membrane would subdivide the container. One side of the subdivision would contain the freshly added blood sample. On the other side of the membrane would be an empty subdivision that would be filled with the sodium acetate solution from Blister 1. The blister would be depressed using a passive device or a motor such as a stepper motor. Depressing the blister pack would inject sodium acetate solution into the empty subdivision. This would initiate the process of extracting ammonia from the whole blood sample into the sodium acetate solution. From this point, Blister 2/Blister 3 would be depressed injecting the sodium hypochlorite and sodium hydroxide into the Nafion subdivision. This would mix these two reagents with the now ammonium containing sodium acetate solution and push the aggregate mixture into the dark, long channel containing the dried 2-phenylphenol and sodium nitroprusside. This action would reconstitute and dissolve these two reagents so that the final solution contains the sodium acetate, ammonium, sodium hypochlorite, sodium hydroxide, sodium nitroprusside and 2-phenylphenol. This solution would then be pushed by further depression of the blisters through the 'mixing region' of the fluidic chip until it reaches the measurement well of the device. The colorimetric reaction would then proceed and the resultant color measured by a device. For example, the cartridge could be inserted into slot A of the chip reader shown in FIG. 5B.

In some embodiments, the cartridge comprises at least one electrode that detects the presence or absence of ammonia or ammonium ion in a sample in a vessel configured to receive a sample from a point external to the cartridge. Once the electrode is activated by the presence of a sample, the storage portion of the cartridge open and release their contents such that a solution from each compartment is released into the mixing portion of the microfluidic conduits. The microfluidic conduits are of a length sufficient to mix all of the reagents from each compartment such that, by the time total fluid volume of reactants reach the readout portion of the cartridge, an indophenol reaction has taken place and an indophenol reaction product (such as indophenol or an indophenol related compound) have formed in the microfluidic conduits.

TABLE 3

Examples of Indophenol Reagent Concentration Ranges

| Reagent | Range |
| --- | --- |
| 2-phenylphenol | From about 50 to about 70 mmol/liter |
| Sodium Nitroprusside | More than about 7 micromoles/liter to about 9 millimoles/liter |
| Sodium Hydroxide | From about 50 to about 500 mmol/liter |
| Sodium Hypochlorite | From about 50 to about 120 mmol/liter |
| Sodium/Calcium Acetate | From about 0.5 to about 1 mol/liter |

Hydrogel

The biosensor comprises a hydrogel in some embodiments. The hydrogel may be a cross-linked polymeric material that swells in water but does not dissolve. It is envisioned that the hydrogel may be capable of absorbing at least about 1 to about 10 times, and in one embodiment at least about 100 times, its own weight of a liquid. The hydrogel chosen for use in the biosensor should depend directly on the method of functionalization. It is envisioned that the hydrogel may be biocompatible. In some embodiments, the hydrogel comprises sodium alginate. In some embodiments, the hydrogel comprises from about 0.1% to about 5% alginate weight/volume. In some embodiments, the hydrogel comprises from about 0.1% to about 4% alginate weight/volume. In some embodiments, the hydrogel comprises from about 0.1% to about 3% alginate weight/volume. In some embodiments, the hydrogel comprises from about 0.1% to about 2% alginate weight/volume. In some embodiments, the hydrogel comprises from about 0.1% to about 1% alginate weight/volume. In some embodiments, the hydrogel comprises from about 0.1% to about 1% alginate weight/volume. In some embodiments, the hydrogel comprises from about 0.2% to about 1% alginate weight/volume. In some embodiments, the hydrogel comprises sodium alginate. In some embodiments, the hydrogel comprises from about 0.3% to about 1% alginate weight/volume. In some embodiments, the hydrogel comprises from about 0.4% to about 1% alginate weight/volume In some embodiments, the hydrogel comprises from about 0.5% to about 1% alginate weight/volume. In some embodiments, the hydrogel comprises from about 0.6% to about 1% alginate weight/volume. In some embodiments, the hydrogel comprises from about 0.7% to about 1% alginate weight/volume. In some embodiments, the hydrogel comprises from about 0.8% to about 1% alginate weight/volume. In some embodiments, the hydrogel comprises from about 0.9% to about 1% alginate weight/volume. In some embodiments, the hydrogel comprises from about 1.0% to about 3.0% alginate weight/volume. In some embodiments, the hydrogel comprises from about 1.0% to about 2.0% alginate weight/volume. In some embodiments, the hydrogel comprises from about 1.0% to about 1.5% alginate weight/volume. In some embodiments, the hydrogel comprises about 1%, about 2%, or about 3% alginate weight/volume. In some embodiments, the hydrogel comprises sodium alginate. The aliginate may be any individual polymer of alginate used in bulk form or repetitive pattern of monomers, G blocks, M blocks, and/or GM blocks. In some embodiments the alginate comprises the formula:

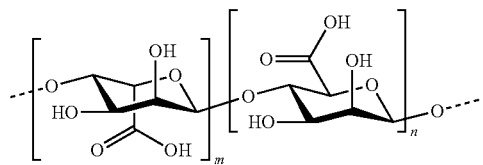

where m and n are any positive integer. In some embodiments m and n are independently variable and any positive integer from about 1 to about 1000. In some embodiments, the hydrogel may be polymerized from acrylic monomers. The acrylic monomer may be one or a combination of the following: acrylamido-glycolic acid, acrylamido-methyl-propa-ne-sulfonic acid, acrylamido-ethylphosphate, diethyl-aminoethyl-acrylamide-, trimethyl-amino-propyl-methacrylamide, N-octylacrylamide, N-phenyl-acrylamide and tert-butyl-acrylamide. In embodiments in which the device contains a cross-linking agent, exemplary cross-linking agents may be N,N'-methylene-bis-acrylamide, N,N'-methylene-bismethacrylamide, diallyltatardiamide and poly(ethylene glycol)dimethacrylate. Examples of suitable hydrogels may also include silicon wafers, borosilicate glass substrates, 2-hydroxyethyl methacrylate (HEMA), N-Iso-propylacrylamide (NIPAAm), and polyethylene glycol (PEG).

The hydrogel may include any number of molecules. For example, the hydrogel may include a polymerized monomer or hydrogel a cross linking agent and optionally a chemical or UV-light activated inducer agent. Examples of such monomers or dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycol-dimethacrylate, N,N'-methylenebisacrylamide, polyethyleneglycoldiacrylate (PEGDA), polyethyleneglycoldimethacrylate (PEGDMA), polyethyleneglycoldiacrylate (PEGDA), polyethyleneglycoldimethacrylate (PEGDMA), poly(vinyliden fluoride) (PVdF) based polymer, a polyacrylonitrile (PAN) based polymer, a polymethylmethacrylate (PMMA) based polymer, a polyvinyl chloride (PVC) based polymer, and a mixture of the poly(vinyliden fluoride) (PVdF) based polymer, polyacrylonitrile (PAN) based polymer, polymethylmethacrylate (PMMA) based polymer, and polyvinyl chloride (PVC) based polymer, and mixtures of any two or more thereof. IN some embodiments, the hydrogel does not comprise 3,4-dihydroxybenzoic acid (3, 4-DHB) or an analog thereof.

Cross linking agents and optionally the chemical or UV-light activated inducer agent may include N,N'-methylenebisacrylamide, methylenebismethacrylamide ethyleneglycol-dimethacrylate and agent N,N'-methylenebisacrylamide. Irgacure 2959 (Ciba); 2,2-dimethoxy-2-phenylacetophenone, 2-methoxy-2-phenylacetone, benzyldimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1,1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyltioxantone, chloro tioxantone, 2,2-chlorobenzophenone, benzyl benzoate, and benzoyl benzoate, TEMED, and ammonium persulfate (APS). In some embodiments, hydrogel comprises a protein, peptide, glycoprotein, proteoglycans, glycosaminoglycans, and/or carbohydrate that is secreted by cells into the extracellular environment. In some embodiments, the secreted protein, peptide, glycoprotein, proteoglycans, glycosamainoglycans, and/or carbohydrate, or structures composed thereof.

In some embodiments, the disclosure relates to a coated biosensor device comprising at least one coating, wherein the biosensor comprises a metabolic enzyme covalently bound or immobilized to the coating, wherein the metabolic enzyme shares at least 70% sequence identify to SEQ ID NO: 19 or SEQ ID NO: 24 or shares at least 70% sequence identify to functional fragments of SEQ ID NO: 19 or SEQ ID NO: 24. In some embodiments, the disclosure relates to a coated biosensor device comprising at least one coating, wherein the biosensor comprises a metabolic enzyme covalently bound or immobilized within the coating, wherein the coating comprises a composition comprising a hydrogel matrix, said matrix comprising any one or combination of: alginate, trehalose, at least one electron mediator, and at least one reduction agent. In some embodiments, the disclosure relates to a coated biosensor device comprising at least one coating, wherein the biosensor comprises a metabolic enzyme covalently bound or immobilized to the coating, wherein the coating comprises a composition comprising a hydrogel matrix, said matrix comprising any one or combination of: poly(ethylene glycol) dimethyacrylate with a molecular weight of about 1000 (PEGDMA-1000), 2-hydroxy-2 methyl propiophenone (HMPP) and at least one acrylate, wherein the acrylate is selected from the group consisting of methacrylic acid (MAA) and methyl methacrylate (MMA), wherein the ratio of PEGDMA:Acrylate is from about 10:90 mol % to about 70:30 mol %, and said HMPP is at a concentration of from about 0.2% to about 0.6%, total weight.

In some embodiments, the hydrogel solution prior to curing comprises trehalose or an analog thereof at a concentration from about 1 nM to about 999 mM. In some embodiments, the hydrogel solution prior to curing comprises trehalose at a concentration from about 1 μM to about 10 mM. In some embodiments, the hydrogel solution prior to curing comprises trehalose at a concentration from about 1 μM to about 9 mM. In some embodiments, the hydrogel solution prior to curing comprises trehalose at a concentration from about 1 μM to about 8 mM. In some embodiments, the hydrogel solution prior to curing comprises trehalose at a concentration from about 1 μM to about 7 mM. In some embodiments, the hydrogel solution prior to curing comprises trehalose at a concentration from about 1 μM to about 6 mM. In some embodiments, the hydrogel solution prior to curing comprises trehalose at a concentration from about 1 μM to about 5 mM. In some embodiments, the hydrogel solution prior to curing comprises trehalose at a concentration from about 1 μM to about 4 mM. In some embodiments, the hydrogel solution prior to curing comprises trehalose at a concentration from about 1 μM to about 3 mM. In some embodiments, the hydrogel solution prior to curing comprises trehalose at a concentration from about 1 μM to about 2 mM. In some embodiments, the hydrogel solution prior to curing comprises trehalose at a concentration from about 1 μM to about 1 mM. In some embodiments, the hydrogel solution prior to curing comprises trehalose at a concentration from about 10 μM to about 1 mM. In some embodiments, the hydrogel solution prior to curing comprises trehalose at a concentration from about 100 μM to about 1 mM. In some embodiments, the hydrogel solution prior to curing comprises trehalose at a concentration from about 200 μM to about 1 mM. In some embodiments, the hydrogel solution prior to curing comprises trehalose at a concentration from about 300 μM to about 1 mM. In some embodiments, the hydrogel solution prior to curing comprises trehalose at a concentration from about 400 μM to about 1 mM. In some embodiments, the hydrogel solution prior to curing comprises trehalose at a concentration from about 500 μM to about 1 mM. In some embodiments, the hydrogel solution prior to curing comprises trehalose at a concentration from about 600 μM to about 1 mM. In some embodiments, the hydrogel solution prior to curing comprises trehalose at a concentration from about 700 μM to about 1 mM. In some embodiments, the hydrogel solution prior to curing comprises trehalose at a concentration from about 800 μM to about 1 mM. In some embodiments, the hydrogel solution (prior to contacting with the electrode) comprises trehalose at a concentration from about 900 μM to about 1 mM.

Mediators

In some embodiments, the biosensor is free of an electron mediator. in some embodiments, the biosensor is free of at least one or a combination of electron mediators selected from: thionine, o-phenylenediamine, methylene blue, and toluidine blue.

In some embodiments, the reaction surface comprises an electron mediator. The mediator facilitates transport of electrons to the electrode. In some embodiments, the mediator is attached to the electrode. In some embodiments, the mediator is embedded in the hydrogel. In some embodiments, the hydrogel comprises one or a combination of mediators chosen from: mediator 2-Acrylamido-2-methylpropanel, sulfonic acid IV, ethacrylic acid, 2-Sulfoethyl methacrylate, and 2-Propene-1-sulfonic acid. U.S. Pat. No. 4,254,222 (1981; Owen) and U.S. Pat. No. 4,351,899 (1982; Owen) disclose an assay for .beta.-hydroxybutyrate where 3-hydroxybutyrate is oxidized to acetoacetate by .beta.-hydroxybutyrate dehydrogenase (HBDH) in the presence of nicotinamide adenine dinucleatide (NAD.sup.+). The reduced NADH produced from this reaction, in turn, reacts with a tetrazolium dye to form a colored formazan compound. The degree and intensity of the color transition correlates to the concentration of .beta.-hydroxybutyrate in the sample solutions. U.S. Pat. No. 5,510,245 (1996; Magers) and U.S. Pat. No. 5,326,697 (1994; Magers) disclose an improved calorimetric method that utilizes a reductive pathway based on lipoamide dehydrogenase (LADH) and a thiol-sensitive indicator dye such as Ellman's reagent. It was found the NADH, produced from the .beta.-hydroxybutyrate dehydrogenase enzyme reaction, can interact with lipoamide dehydrogenase (LADH) and D,L-lipoamide to form athiol compound (6,8-dimercaptooctamide). The 6,8-dimercaptooctamide then interacts with a thiol-responsive indicator dye such as Ellman's reagent. Upon reaction, the thiol-sensitive indicator dye undergoes a detectable color transition that can be used to measure the level of 3-hydrobutyrate in the blood sample. The colorimetric methods for 3-hydrobutyrate suffer the disadvantages of poor stability, interference from co-existing species such as ascorbate, glutathione etc. in the blood, and insufficient sensitivity and accuracy. NAD- and NADP-dependent enzymes are of great interest insofar as many have substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrode via the mediated oxidation of the reduced co factors NADH and NAD PH. NAD- and NADP-dependent enzymes are generally intracellular oxidoreductases. The oxidoreductases are further classified according to the identity of the donor group of a substrate upon which they act. The category of oxidoreductases is also broken down according to the type of acceptor utilized by the enzyme. The enzymes of relevance have NAD+ or NADP+ as acceptors. These enzymes generally possess sulphydryl groups within their active sites and hence can be irreversibly inhibited by thiol-reactive reagents such as iodoacetate. An irreversible inhibitor forms a stable compound, often through the formation of a covalent bond with a particular amino acid residue that is essential for enzymatic activity. U.S. Pat. No. 6,541,216 (2003; Wilsey et al.) discloses a biosensor and method to test blood ketone bodies using an amperometric meter. The test strip has a reagent that is reactive with β-hydroxybutyrate in sample solution to generate an electrical output signal, which is related to the concentration of .beta.-hydroxybutyrate in the sample solution. The reagent in this method includes ferricyanide salt as mediator, .beta.-hydroxybutyrate dehydrogenase as the first enzyme operative to catalyze the oxidation of .beta.-hydroxybutyrate, NAD+ as a cofactor corresponding to the first enzyme, and diaphorase as the second enzyme operative to catalyze the oxidation of a reduction form of the cofactor (NADH). The oxidation form of the mediator will accept the electron from the second enzyme and generates an electrical signal at the electrode surface, which is related to the concentration level of .beta.-hydroxybutyrate. U.S. Pat. No. 6,736,957 (2004; Forrow et al.) and a research paper (N. J. Forrow et. al, Biosensors & Bioelectronics, 2005, 20, 1617-1625) disclose an amperometric biosensor for .beta.-hydroxybutyrate based on the discovery of NAD+ and NADP- mediator compounds that do not bind irreversibly to thiol groups in the active sites of intracellular dehydrogenase enzymes. These mediator compounds such as 1,10-phenanthroline quinone (1,10-PQ), which is used as an electron mediator in their electrochemical measurement system, can increase the stability and reliability response in amperometric electrodes constructed from NAD- and NADP-dependent enzyme. The dry reagents include 1,10-phenanthroline quinone (1,10-PQ), .beta.-hydroxybutyrate dehydrogenase and NAD+ as the cofactor. This sensor shows reliable and sensitive response to the concentration levels of .beta.-hydroxybutyrate in blood samples. Meldola's Blue (MB) was also studied as a mediator in the system, but it was found that MB did not work well in their electrochemical test system due to the inhibition of .beta.-hydroxybutyrate dehydrogenase enzyme activity by MB and poor long term stability of the test strips.

The dehydrogenase enzymes such as, for example, glucose dehydrogenase, D-3-hydroxybutyrate dehydrogenase (HBDH), and lactate dehydrogenase et. al are known to be common dehydrogenases for construction of biosensors. As disclosed by Forrow et al., there are certain mediators that are considered efficient mediators for NADH but are irreversible enzyme inhibitors such as Meldola's blue, 4-methyl-1,2-benzoquinone (4-MBQ), 1-methoxy phenazine methosulphate (1-Meo-PMS) and 2,6-dichloroindophenol (DCIP), which cause losing the activity of enzymes, insensitive response and poor stability in sensors containing dehydrogenase enzymes. In some embodiments, the biosensor, system, or test strip comprise any one or more of the mediators disclosed herein. In some embodiments, the mediator is chosen from one or a combination of: ortho-quinones, para-quinones and quinoneimines in their basic structural elements. The representative examples of the quinoid structure type include, but are not limited to, benzo-.alpha.-phenazoxonium chloride, Meldola's Blue (MB), 3,4-methyl-1,2-benzoquinone, 1-methoxy phenazine methosulphate, 1,10-phenanthroline quinone (1,10-PQ). In some embodiments, the at least one mediator is selected from one or a mixture of the following compounds:

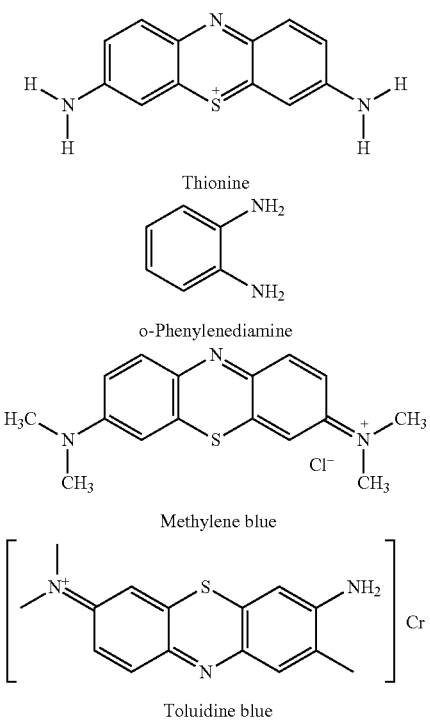

Thionine o-Phenylenediamine

Methylene blue

Toluidine blue

Cofactors/Reduction Agent
NAD+
FAD+
Ascorbic Acid
Flavin mononucleotide
Flavin adenine dinucleotide
Coenzyme F420
Glutathione
Heme
Pyrroloquinoline quinone
Enzymes
Any one or more metabolic enzymes may be chosen to used with the present disclosure. Metabolic enzymes that can be used individually or in combination with the biosensor, system or test strip disclosed herein include: any bacterial clone of phenylalanine dehydrogenase, histidine ammonia lyase, mistidine oxidase. pheylalanine lyase, glutamate dehydrogenase. In some embodiments the enzyme is chosen from any one or combination of enzymes disclosed below or their respective functional fragments that are at least 70%, 80%, 85%, 90%, 95%, 96%, 97%, 98%, or 99% homoglous to the full-length enzyme or nucleic acid encoding such enzyme.

| Organism | Enzyme | GenBank Accession No | Seq ID No |
|---|---|---|---|
| *Thermoactinomyces intermedius* | phenylalanine dehydrogenase | D00631.1 | 19 |
| *Solanum lycopersicum* | phenylalanine ammonia-lyase | XM_004246602 | 20 |
| *Thermoactinomyces intermedius* | phenylalanine dehydrogenase | DD421709.1 | 21 |
| *Caenorhabditis remanei* | phenylalanine dehydrogenase | XM_003102740 | 22 |
| *Arabidopsis thaliana* | glutamate dehydrogenase | NM_121822.3 | 23 |
| *Spirochaeta africana* | Hisitidine ammonia lyase | NC_017098.1 | 24 |

SEQ ID NO: 19

MRDVFEMMDRYGHEQVIFCRHPQTGLKAIIALHNTTAGPALGGCRMIPYASTDEALEDVL

RLSKGMTYKCSLADVDFGGGKMVIIGDPKKDKSPELFRVIGRFVGGLNGRFYTGTDMGTN

PEDFVHAARESKSFAGLPKSYGGKGDTSIPTALGVFHGMRATARFLWGTDQLKGRVVAIQ

GVGKVGERLLQLLVEVGAYCKIADIDSVRCEQLKEKYGDKVQLVDVNRIHKESCDIFSPCA

KGGVVNDDTIDEFRCLAIVGSANNQLVEDRHGALLQKRSICYAPDYLVNAGGLIQVADEL

EGFHEERVLAKTEAIYDMVLDIFHRAKNENITTCEAADRIVMERLKKLTDIRRILLEDPRNS

ARR

SEQ ID NO: 20

MASSIVQNGHVNGEAMDLCKKSINVNDPLNWEMAAESLRGSHLDEVKKMVDEFRKPIVK

LGGETLTVAQVASIANVDNKSNGVKVELSESARAGVKASSDWVMDSMGKGTDSYGVTTG

FGATSHRRTKNGGALQKELIRFLNAGVFGNGTESSHTLPHSATRAAMLVRINTLLQGYSGI

RFEILEAITKLINSNITPCLPLRGTITASGDLVPLSYIAGLLTGRPNSKAVGPNGEKLNAEEAF

RVAGVTSGFFELQPKEGLALVNGTAVGSGMASMVLFESNILAVMSEVLSAIFAEVMNGKP

EFTDYLTHKLKHHPGQIEAAAIMEHILDGSSYVKAAQKLHEMDPLQKPKQDRYALRTSPQ

WLGPQIEVIRAATKMIEREINSVNDNPLIDVSRNKALHGGNFQGTPIGVSMDNTRLALASIG

KLMFAQFSELVNDYYNNGLPSNLTAGRNPSLDYGLKGAEIAMASYCSELQFLANPVTNHV

QSAEQHNQDVNSLGLISARKTAEAVDILKLMSSTYLVALCQAIDLRHLEENLRSAVKNTVS

QVAKRTLTMGANGELHPARFCEKELLRVVDREYVFAYADDPCSSTYPLMQKLRQVLVDH

AMKNGESEKNVNSSIFQKIVAFEDELKAVLPKEVESARAVVESGNPAIPNRITECRSYPLYR

LVRQELGSELLTGEKVRSPGEEIDKVFTAMCNGQIIDPLLECLKSWNGAPLPIC

SEQ ID NO: 21
```
      atgcgcgacg tgtttgaaat gatggaccgc tatggccacg agcaggtcat tttttgccgt
  61  catccgcaaa ccggtctcaa agcgatcatc gccttgcata atacaaccgc ggggccggct
 121  tgggtggat  gccgcatgat cccgtatgct cgacggacg aagccttgga ggatgttttg
 181  cggttgtcca aaggcatgac ctataaatgc agtctggcgg atgtggactt tggcgggga
 241  aaaatggtta tcatcggcga tccgaaaaaa gataaatcgc cggagttgtt tcgcgtgatc
 301  ggccgttttg tgggcgggtt aaacggccgt ttctataccg gaaccgacat gggaaccaat
 361  ccggaagatt ttgtccatgc cgccaggaa tcgaaatctt ttgccggatt gccgaaatcg
 421  tacggcggaa agggggacac atccattccc accgcgctcg ggtgtttca cggaatgcgg
 481  gccaccgccc ggtttttatg ggggacggat cagctgaaag gcgtgtggt tgccatccaa
 541  ggagtcggca aggtgggaga gcgcttgttg cagcttttgg tcgaagtggg ggcttactgc
```

```
601  aaaattgccg  acatcgattc  ggtgcgatgc  gaacagctga  aagaaaagta  tggcgacaag 661  gtccaattgg  tggatgtgaa  ccggattcac  aaggagagtt  gcgatatttt  ctcgccttgc 721  gccaaaggcg  gcgtggtcaa  tgatgacacc  attgacgagt  tccgttgcct  ggccattgtc 781  ggatccgcca  acaaccaact  ggtggaagac  cggcatgggg  cactgcttca  aaaacggagc 841  atttgttatg  cacccgatta  tctggtgaat  gccggcgggc  tgattcaagt  ggctgatgaa 901  ctggaaggct  tccatgaaga  gagagtgctc  gccaaaaccg  aagcgattta  tgacatggtc 961  ctggatattt  ttcaccgggc  gaaaaatgag  aatattacca  cttgtgaggc  agcggaccgg 1021 atcgtgatgg  agcgtttgaa  aaagttaacc  gatattcgcc  ggatcttgtt  ggaggatccc 1081 cgcaacagcg  caaggaggta  a
```

SEQ ID NO: 22
MDFKAKLLAEMAKKRKAVSGLEVKEGGAKFVRGADLESKRTQEYEAKQEELAIKKRKAD

DEILQESTSRAKIVPEVPEAEFDEKTPMPEIHARLRQRGQPILLFGESELSVRKRLHQLEIEQP

ELNEGWENEMQTAMKFIGKEMDKAVVEGTADSATRHDIALPQGYEEDNWKSIEHASTLL

GVGDEMKRDCDIILSICRYILARWARDLNDRPLDVKKTAQGMHEAAHHKQTTMHLKSLM

TSMEKYNVNNDIRHHLAKICRLLVIERNYLEANNAYMEMAIGNAPWPVGVTRSGIHQRPG

SAKAYVSNIAHVLNDETQRKYIQAFKRLMTKLQEYFPTDPSKSVEFVKKSV

SEQ ID NO: 23
MNALAATNRNFKLAARLLGLDSKLEKSLLIPFREIKVECTIPKDDGTLASFVGFRVQHDNA

RGPMKGGIRYHPEVDPDEVNALAQLMTWKTAVAKIPYGGAKGGIGCDPSKLSISELERLTR

VFTQKIHDLIGIHTDVPAPDMGTGPQTMAWILDEYSKFHGYSPAVVTGKPIDLGGSLGRDA

ATGRGVMFGTEALLNEHGKTISGQRFVIQGFGNVGSWAAKLISEKGGKIVAVSDITGAIKN

KDGIDIPALLKHTKEHRGVKGFDGADPIDPNSILVEDCDILVPAALGGVINRENANEIKAKFI

IEAANHPTDPDADEILSKKGVVILPDIYANSGGVTVSYFEWVQNIQGFMWEEEKVNDELKT

YMTRSFKDLKEMCKTHSCDLRMGAFTLGVNRVAQATILRGWGA

SEQ ID NO: 24
MNTVTNQWKAVDIFTQIRDHEQVVFCNDKNTGLKAIIAIHDTTLGPALGGCRMYPYATVE

DALFDVLRLSKGMTYKCLAADVDFGGGKAVIIGDPHKDKTPELFRAFGQFVESLNGRFYT

GTDMGTTPDDFVHAMKETNCIVGVPEEYGGSGDSSVPTALGVIYGIQATNKVIWGSDELH

GKTYAIQGLGKVGRKVAERLLKEGADLYVCDIHPTAIEAIVSYAKKLGANVKVVQGTEIY

RTDADIFVPCAFGNVVNDNTIHVLKVKAIVGSANNQLLDVRHGQLLKEKGILYAPDYIVNA

GGLIQVADELYGLNKERVLQKTKAIYSTLLHIYSRAEADHITTIEAANRFCEERLQQRSRRN

DFFTHRKQPKWDIRR

Solid Support

There are many forms of ammonia- or ammonium ion-measuring devices; one common type is represented by hand-held electronic meters which receive blood samples via enzyme-based test strips. In using these systems, the patient may for example lances a finger or alternate body site to obtain a blood sample, the strip is inserted into a test strip opening in the meter housing, the sample is applied to the test strip and the electronics in the meter convert a current generated by the enzymatic reaction in the test strip to a amino acid concentration value.

Solid supports of the disclosure may be solid state but are a flexible substrate. According to the disclosure, the interdigitated array or at least one electrode is disposed proximal to, e.g., on, a flexible substrate. To act as a flexible substrate, a material must be flexible and also insulating, and is typically relatively thin. The substrate should be capable of adhering components of an IDA, or additional components of a sensor, to its surface. Such thin, insulative, flexible substrates are known in the art of flexible circuits and flex circuit photolithography. "Flexible substrates" according to the present disclosure can be contrasted to non-flexible substrates used in integrated circuit (IC) photolithography but not in flexible circuit photolithography. Examples of non-flexible substrates used in IC photolithography include silicon, aluminum oxide, and other ceramics. These non-flexible substrates are chosen to be processable to a very flat surface. Typical flexible substrates for use in the disclosure are constructed of thin plastic materials, e.g., polyester, especially high temperature polyester materials; polyethylene naphthalate (PEN); and polyimide, or mixtures of two or more of these. Polyimides are available commercially, for example under the trade name Kapton®, from I.E. duPont de Nemours and Company of Wilmington, Del. (duPont). Polyethylene naphthalate is commercially available as Kaladex®, also from duPont. A particularly preferred flexible substrate is 7 mil thick Kaladex® film.

Interdigitated arrays of the disclosure can be used in applications generally known to incorporate electrodes, especially applications known to involve interdigitated arrays of electrodes. Various applications are known in the arts of electronics and electrochemistry, including applications relating to process and flow monitoring or control, and chemical analytical methods. The arrays may be particularly useful as a component of an electrochemical sensor, where there is added value, benefit, or cost efficiency, to the use of a flexible substrate, or where there is value, benefit, or cost efficiency in having an interdigitated array of dimensions relatively larger than the dimensions of interdigitated arrays conventionally disposed on non-flexible substrates.

An interdigitated array of the disclosure can, for example, be included in an electrochemical sensor (sometimes referred to as a "biosensor" or simply "sensor") used in electrochemical detection methods. Electrochemical detection methods operate on principles of electricity and chemistry, or electrochemistry, e.g., on principles of relating the magnitude of a current flowing through a substance, the resistance of a substance, or a voltage across the substance given a known current, to the presence of a chemical species within the substance. Some of these methods can be referred to as potentiometric, chronoamperometric, or impedance, depending on how they are practiced, e.g., whether potential difference or electric current is controlled or measured. The methods and sensors, including sensors of the disclosure, can measure current flowing through a substance due directly or indirectly to the presence of a particular chemical compound (e.g., an analyte or an electroactive compound), such as a compound within blood, serum, interstitial fluid, or another bodily fluid, e.g., to identify levels of amino acids, blood urea, nitrogen, cholesterol, lactate, and the like. Adaptations of some electrochemical methods and electrochemical sensors, and features of their construction, electronics, and electrochemical operations, are described, for example, in U.S. Pat. Nos. 5,698,083, 5,670,031, 5,128,015, and 4,999,582, each of which is incorporated herein by reference.

In some embodiments, any of the above biosensor cartridges, devices, or methods comprise a volume of anticoagulant. In some embodiments, the volume of the anticoagulant disclosed herein in a volume of about 10 microliters. In some embodiments, the volume of the anticoagulant disclosed herein in a volume of about 20 microliters. In some embodiments, the volume of the anticoagulant disclosed herein in a volume of about 30 microliters. In some embodiments, the volume of the anticoagulant disclosed herein in a volume of about 40 microliters. In some embodiments, the volume of the anticoagulant disclosed herein in a volume of about 50 microliters. In some embodiments, the volume of the anticoagulant disclosed herein in a volume of about 100 microliters.

In some embodiments, the methods disclosed herein comprise a step of mixing a sample comprising blood with an anticoagulant such as heparin, Acenocoumarol, phenprocoumon, Atromentin, Brodifacoum, Phenindione, Coumadin or the like. In some embodiments the biosensor, cartridge, device, or test strip comprise a mechanical shaker mechanism configured to shake one or more volumes within the at least one vessel, microfluidic conduit, or mixing portion of the biosensor, cartridge, device, or test strip.

Methods

The disclosure relates to a method of diagnosing or prognosing a clinical outcome of a subject with hyperammonemia or a hyperammonia related disorder, comprising contacting a sensor, system, or test strip disclosed herein with a sample of bodily fluid, and quantifying a level of ammonia or ammonium ion in the sample; and comparing the level of amino acid in the sample to a threshold value of what is considered normal level of amino acid level in the bodily fluid. In some embodiments, the method relates to to a method of diagnosing or prognosing a clinical outcome of a subject suspected of having or having been previously diagnosed with hyerpammonemia or a hyperammonemia-related disorder and/or at least one aminoacidopathy.

In some embodiments, the method relates to to a method of diagnosing or prognosing a clinical outcome of a subject suspected of having or having been previously diagnosed with at least one hyerpammonemia or a hyperammonemia-related disorder. The ranges of what ammonia or ammonium ion levels are considered normal for each age type are below in Table 4. If, after performing the quantification steps provided herein, the amount of ammonia or ammonium ion in the sample solution exceeds or falls below the ranges provided, diet regimen, exercise regimen, and/or medical treatment may be initiated or changed such that ammonia or ammonium ion levels are monitored until the subject's levels have stabilized or fall within what is considered a healthy range.

TABLE 4

Ammonia Ranges

| Case | Range |
| --- | --- |
| Newborn - Healthy | Less than 110 micromoles/liter |
| Newborn - Suspected Metabolic Disorder | Greater than 200 micromoles/liter |
| Older than Newborn - Healthy | 50-80 micromoles/liter |
| Older than Newborn - Suspected Metabolic Disorder | Greater than 100 micromoles/liter |
| Hepatic Encephalopathy | Greater than 70 micromoles/liter |

The disclosure relates to a method of detecting the presence or absence or quantity of ammonia or ammonium related disorder in bodily fluids. The disclosure also relates to a method of quantifying the concentration of ammonia or ammonium ion in bodily fluids of a subject. Quantification can occur at the point-of-care due to the quick enzymatic reaction readout caused by the generation of a detectable current within a circuit after exposure of a sample from a subject to one or a plurality of vessels comprising any one or combination of indophenol reagents disclosed herein. In some embodiments, the device or system described herein may be utilized to detect if a person has abnormally high or low levels of ammonia in the blood, after which an electronic message or display may then be provided to the user of the device or system or activated on a display by one or more processors or microchips that remotely or directly access one or more storage memories comprising one or more concentration values of ammonia or ammonium ion in sample of the subject. In some embodiments, multiple concentration values may be obtained either simultaneously or in series, compared or analyzed by the one or more processors operably connected to the device or system disclosed herein. In some embodiments, multiple concentration values of a subject over a time period may be compared or analyzed by the one or more processors operably connected to the device or system disclosed herein, after which a message comprising the concentration value and/or threshold values are displayed. In some embodiments, the message optionally includes a signal indicating that the subject should seek medical treatment or alter diet to control ammonia or ammonium ion levels in the subject.

The disclosure also relates to a method of diagnosing a subject with a liver dysfunction comprising:

(a) contacting a sample of bodily fluid from a subject to the to the biosensor, system or test strip disclosed herein;

(b) quantifying one or more concentration values of ammonia in the sample;

(c) comparing the one or more concentration values of ammonia in the sample to a threshold value of ammonia concentration identified as being in a healthy range; and (d) identifying the subject as having a metabolic disease if the one or more concentration values of ammonia in the sample exceed or fall below the threshold value. In some embodiments, if the sample is blood or whole blood, the method comprises contacting the sample with an anticoagulant before or simultaneously with step (a).

The disclosure also relates to a method of diagnosing a subject with hyperammonemia comprising:

(a) contacting a sample of bodily fluid from a subject to the to the biosensor, system or test strip disclosed herein;

(b) quantifying one or more concentration values of ammonia in the sample;

(c) comparing the one or more concentration values of ammonia in the sample to a threshold value of ammonia concentration identified as being in a healthy range; and (d) identifying the subject as having a metabolic disease if the one or more concentration values of ammonia in the sample exceed or fall below the threshold value. In some embodiments, if the sample is blood or whole blood, the method comprises contacting the sample with an anticoagulant before or simultaneously with step (a).

The disclosure also relates to a method of quantifying the amount of amino acid in sample comprising:

(a) contacting a sample of bodily fluid from a subject to the to the biosensor, system or test strip disclosed herein;

(b) quantifying one or more concentration values of ammonia in the sample;

(c) comparing the one or more concentration values of ammonia in the sample to a threshold value of ammonia concentration identified correlating to amino acid quantity; and (d) identifying the amino acid levels if the one or more concentration values of ammonia in the sample exceed or fall below the threshold value.

Any amino acid may be detected using wherein the biosensor, system or test strip disclosed herein comprises an enzyme disclosed herein or a functional fragment that has 70, 75, 80, 85, 90, 91, 92, 93, 94, 95, 96, 97, 98, or 99% sequence identity to any enzyme disclosed herein. One of ordinary skill in the art would know, for instance, that to detect the presence, absence, or quantity of amino acids listed on Table 5, one or more recombinant or synthetic enzymes disclosed herein or a functional fragment thereof that has 70, 75, 80, 85, 90, 91, 92, 93, 94, 95, 96, 97, 98, or 99% sequence identity to any sequence (either nucleic acid or encoded amino acid) disclosed herein.

In some embodiments, the phenolic reagent or indophenol reagent is used in a range from about 50 to about 70 mmol/liter. In some embodiments, the phenolic reagent or indophenol reagent is used in a range from about 52 to about 70 mmol/liter. In some embodiments, the phenolic reagent or indophenol reagent is used in a range from about 54 to about 70 mmol/liter. In some embodiments, the phenolic reagent or indophenol reagent is used in a range from about 56 to about 70 mmol/liter. In some embodiments, the phenolic reagent or indophenol reagent is used in a range from about 58 to about 70 mmol/liter. In some embodiments, the phenolic reagent or indophenol reagent is used in a range from about 60 to about 70 mmol/liter. In some embodiments, the phenolic reagent or indophenol reagent is used in a range from about 62 to about 70 mmol/liter. In some embodiments, the phenolic reagent or indophenol reagent is used in a range from about 64 to about 70 mmol/liter. In some embodiments, the phenolic reagent or indophenol reagent is used in a range from about 66 to about 70 mmol/liter. In some embodiments, the phenolic reagent or indophenol reagent is used in a range from about 68 to about 70 mmol/liter. In some embodiments, the phenolic reagent or indophenol reagent is used in a range from about 50 to about 68 mmol/liter. In some embodiments, the phenolic reagent or indophenol reagent is used in a range from about 50 to about 66 mmol/liter. In some embodiments, the phenolic reagent or indophenol reagent is used in a range from about 50 to about 64 mmol/liter. In some embodiments, the phenolic reagent or indophenol reagent is used in a range from about 50 to about 62 mmol/liter. In some embodiments, the phenolic reagent or indophenol reagent is used in a range from about 50 to about 60 mmol/liter. In some embodiments, the phenolic reagent or indophenol reagent is used in a range from about 50 to about 58 mmol/liter. In some embodiments, the phenolic reagent or indophenol reagent is used in a range from about 50 to about 56 mmol/liter. In some embodiments, the phenolic reagent or indophenol reagent is used in a range from about 50 to about 54 mmol/liter. In some embodiments, the phenolic reagent or indophenol reagent is used in a range from about 50 to about 52 mmol/liter. In some embodiments, the phenolic reagent or indophenol reagent is used in concentration about 59 mmol/liter. In some embodiments, the phenolic reagent or indophenol reagent is 2-phenylphenol.

In some embodiments, the basic buffer is used in a range from about 50 to about 500 mmol/liter. In some embodiments, the basic buffer is used in a range from about 120 to about 500 mmol/liter. In some embodiments, the basic buffer is used in a range from about 140 to about 500 mmol/liter. In some embodiments, the basic buffer is used in a range from about 160 to about 500 mmol/liter. In some embodiments, the basic buffer is used in a range from about 180 to about 500 mmol/liter. In some embodiments, the basic buffer is used in a range from about 200 to about 500 mmol/liter. In some embodiments, the basic buffer is used in a range from about 220 to about 500 mmol/liter. In some embodiments, the basic buffer is used in a range from about 240 to about 500 mmol/liter. In some embodiments, the basic buffer is used in a range from about 260 to about 500 mmol/liter. In some embodiments, the basic buffer is used in a range from about 280 to about 500 mmol/liter. In some embodiments, the basic buffer is used in a range from about 300 to about 500 mmol/liter. In some embodiments, the basic buffer is used in a range from about 320 to about 500 mmol/liter. In some embodiments, the basic buffer is used in a range from about 340 to about 500 mmol/liter. In some embodiments, the basic buffer is used in a range from about 360 to about 500 mmol/liter. In some embodiments, the basic buffer is used in a range from about 380 to about 500 mmol/liter. In some embodiments, the basic buffer is used in a range from about 400 to about 500 mmol/liter. In some embodiments, the basic buffer is used in a range from about 420 to about 500 mmol/liter. In some embodiments, the basic buffer is used in a range from about 440 to about 500 mmol/liter.

In some embodiments, the basic buffer is used in a range from about 460 to about 500 mmol/liter. In some embodiments, the basic buffer is used in a range from about 480 to about 500 mmol/liter. In some embodiments, the basic buffer is used in a range from about 100 to about 480 mmol/liter. In some embodiments, the basic buffer is used in a range from about 100 to about 460 mmol/liter. In some embodiments, the basic buffer is used in a range from about 100 to about 440 mmol/liter. In some embodiments, the basic buffer is used in a range from about 100 to about 420 mmol/liter. In some embodiments, the basic buffer is used in a range from about 100 to about 400 mmol/liter. In some embodiments, the basic buffer is used in a range from about 100 to about 380 mmol/liter. In some embodiments, the basic buffer is used in a range from about 100 to about 360 mmol/liter. In some embodiments, the basic buffer is used in a range from about 100 to about 340 mmol/liter. In some embodiments, the basic buffer is used in a range from about 100 to about 320 mmol/liter. In some embodiments, the basic buffer is used in a range from about 100 to about 300 mmol/liter. In some embodiments, the basic buffer is used in a range from about 100 to about 280 mmol/liter. In some embodiments, the basic buffer is used in a range from about 100 to about 260 mmol/liter. In some embodiments, the basic buffer is used in a range from about 100 to about 240 mmol/liter. In some embodiments, the basic buffer is used in a range from about 100 to about 220 mmol/liter. In some embodiments, the basic buffer is used in a range from about 100 to about 200 mmol/liter. In some embodiments, the basic buffer is used in a range from about 100 to about 180 mmol/liter. In some embodiments, the basic buffer is used in a range from about 100 to about 160 mmol/liter. In some embodiments, the basic buffer is used in a range from about 100 to about 140 mmol/liter. In some embodiments, the basic buffer is used in a range from about 100 to about 120 mmol/liter. In some embodiments, the basic buffer is used in a concentration about 50 mmol/liter. In some embodiments, the basic buffer is sodium hydroxide. In some embodiments, the basic buffer is used in a concentration about 100 mmol/liter. In some embodiments, the basic buffer is sodium hydroxide. In some embodiments, the basic buffer is used in a concentration about 200 mmol/liter. In some embodiments, the basic buffer is sodium hydroxide. In some embodiments, the basic buffer is used in a concentration about 300 mmol/liter. In some embodiments, the basic buffer is sodium hydroxide. In some embodiments, the basic buffer is used in a concentration about 400 mmol/liter. In some embodiments, the basic buffer is sodium hydroxide. In some embodiments, the basic buffer is used in a concentration about 500 mmol/liter. In some embodiments, the basic buffer is sodium hydroxide.

In some embodiment, the catalyst is sodium nitroprusside or any nitroprusside salt. In some embodiments, the sodium nitroprusside or nitroprusside salt is from about 7.1 micromolar solution to about 9 mM solution in liquid phase. In some embodiments, the catalyst is used in a concentration of about 8 micromoles/liter. In some embodiments, the catalyst is used in a concentration of about 9 micromoles/liter. In some embodiments, the catalyst is used in a concentration of about 10 micromoles/liter. In some embodiments, the catalyst is used in a concentration of about 25 micromoles/liter. In some embodiments, the catalyst is used in a concentration of about 50 micromoles/liter. In some embodiments, the catalyst is used in a concentration of about 75 micromoles/liter. In some embodiments, the catalyst is used in a concentration of about 100 micromoles/liter. In some embodiments, the catalyst is used in a concentration of about 200 micromoles/liter. In some embodiments, the catalyst is used in a concentration of about 300 micromoles/liter. In some embodiments, the catalyst is used in a concentration of about 400 micromoles/liter. In some embodiments, the catalyst is used in a concentration of about 500 micromoles/liter. In some embodiments, the catalyst is used in a concentration of about 600 micromoles/liter. In some embodiments, the catalyst is used in a concentration of about 700 micromoles/liter. In some embodiments, the catalyst is used in a concentration of about 900 micromoles/liter. In some embodiments, the catalyst is used in a concentration of about 1 millimoles/liter. In some embodiments, the catalyst is used in a concentration of about 2 millimoles/liter. In some embodiments, the catalyst is used in a concentration of about 3 millimoles/liter. In some embodiments, the catalyst is used in a concentration of about 4 millimoles/liter. In some embodiments, the catalyst is used in a concentration of about 5 millimoles/liter. In some embodiments, the catalyst is used in a concentration of about 6 millimoles/liter. In some embodiments, the catalyst is used in a concentration of about 7 millimoles/liter. In some embodiments, the catalyst is used in a concentration of about 8 millimoles/liter. In some embodiments, the catalyst is used in a concentration of about 9 millimoles/liter. In some embodiments, the catalyst is used in a concentration of about 10 millimoles/liter. In some embodiments, the catalyst is sodium nitroprusside.

In some embodiments, the hypohalite is used in a range from about 50 to about 120 mmol/liter. In some embodiments, the hypohalite is used in a range from about 52 to about 120 mmol/liter. In some embodiments, the hypohalite is used in a range from about 54 to about 120 mmol/liter. In some embodiments, the hypohalite is used in a range from about 56 to about 120 mmol/liter. In some embodiments, the hypohalite is used in a range from about 58 to about 120 mmol/liter. In some embodiments, the hypohalite is used in a range from about 58 to about 120 mmol/liter. In some embodiments, the hypohalite is used in a range from about 60 to about 120 mmol/liter. In some embodiments, the hypohalite is used in a range from about 62 to about 120 mmol/liter. In some embodiments, the hypohalite is used in a range from about 64 to about 120 mmol/liter. In some embodiments, the hypohalite is used in a range from about 66 to about 120 mmol/liter. In some embodiments, the hypohalite is used in a range from about 68 to about 120 mmol/liter. In some embodiments, the hypohalite is used in a range from about 70 to about 120 mmol/liter. In some embodiments, the hypohalite is used in a range from about 72 to about 120 mmol/liter. In some embodiments, the hypohalite is used in a range from about 74 to about 120 mmol/liter. In some embodiments, the hypohalite is used in a range from about 76 to about 120 mmol/liter. In some embodiments, the hypohalite is used in a range from about 78 to about 120 mmol/liter. In some embodiments, the hypohalite is used in a range from about 80 to about 120 mmol/liter. In some embodiments, the hypohalite is used in a range from about 82 to about 120 mmol/liter. In some embodiments, the hypohalite is used in a range from about 82 to about 120 mmol/liter. In some embodiments, the hypohalite is used in a range from about 84 to about 120 mmol/liter. In some embodiments, the hypohalite is used in a range from about 86 to about 120 mmol/liter. In some embodiments, the hypohalite is used in a range from about 90 to about 120 mmol/liter. In some embodiments, the hypohalite is used in a range from about 92 to about 120 mmol/liter. In some embodiments, the hypohalite is used in a range from about 94 to about 120 mmol/liter. In some embodiments, the hypohalite is used in a range from about 96 to about 120 mmol/liter. In some embodiments, the hypohalite is used in a range from about 98 to about 120 mmol/liter. In some embodiments, the hypohalite is used in a range from about 100 to about 120 mmol/liter. In some embodiments, the hypohalite is used in a range from about 102 to about 120 mmol/liter. In some embodiments, the hypohalite is used in a range from about 104 to about 120 mmol/liter. In some embodiments, the hypohalite is used in a range from about 106 to about 120 mmol/liter. In some embodiments, the hypohalite is used in a range from about 108 to about 120 mmol/liter. In some embodiments, the hypohalite is used in a range from about 110 to about 120 mmol/liter. In some embodiments, the hypohalite is used in a range from about 112 to about 120 mmol/liter. In some embodiments, the hypohalite is used in a range from about 114 to about 120 mmol/liter. In some embodiments, the hypohalite is used in a range from about 116 to about 120 mmol/liter. In some embodiments, the hypohalite is used in a range from about 118 to about 120 mmol/liter. In some embodiments, the hypohalite is used in a range from about 50 to about 118 mmol/liter. In some embodiments, the hypohalite is used in a range from about 50 to about 116 mmol/liter. In some embodiments, the hypohalite is used in a range from about 50 to about 114 mmol/liter. In some embodiments, the hypohalite is used in a range from about 50 to about 112 mmol/liter. In some embodiments, the hypohalite is used in a range from about 50 to about 110 mmol/liter. In some embodiments, the hypohalite is used in a range from about 50 to about 108 mmol/liter. In some embodiments, the hypohalite is used in a range from about 50 to about 106 mmol/liter. In some embodiments, the hypohalite is used in a range from about 50 to about 104 mmol/liter. In some embodiments, the hypohalite is used in a range from about 50 to about 102 mmol/liter. In some embodiments, the hypohalite is used in a range from about 50 to about 100 mmol/liter. In some embodiments, the hypohalite is used in a range from about 50 to about 98 mmol/liter. In some embodiments, the hypohalite is used in a range from about 50 to about 96 mmol/liter. In some embodiments, the hypohalite is used in a range from about 50 to about 94 mmol/liter. In some embodiments, the hypohalite is used in a range from about 50 to about 92 mmol/liter. In some embodiments, the hypohalite is used in a range from about 50 to about 90 mmol/liter. In some embodiments, the hypohalite is used in a range from about 50 to about 88 mmol/liter. In some embodiments, the hypohalite is used in a range from about 50 to about 86 mmol/liter. In some embodiments, the hypohalite is used in a range from about 50 to about 84 mmol/liter. In some embodiments, the hypohalite is used in a range from about 50 to about 82 mmol/liter. In some embodiments, the hypohalite is used in a range from about 50 to about 80 mmol/liter. In some embodiments, the hypohalite is used in a range from about 50 to about 78 mmol/liter. In some embodiments, the hypohalite is used in a range from about 50 to about 76 mmol/liter. In some embodiments, the hypohalite is used in a range from about 50 to about 74 mmol/liter. In some embodiments, the hypohalite is used in a range from about 50 to about 72 mmol/liter. In some embodiments, the hypohalite is used in a range from about 50 to about 70 mmol/liter. In some embodiments, the hypohalite is used in a range from about 50 to about 68 mmol/liter. In some embodiments, the hypohalite is used in a range from about 50 to about 66 mmol/liter. In some embodiments, the hypohalite is used in a range from about 50 to about 64 mmol/liter. In some embodiments, the hypohalite is used in a range from about 50 to about 62 mmol/liter. In some embodiments, the hypohalite is used in a range from about 50 to about 60 mmol/liter. In some embodiments, the hypohalite is used in a range from about 50 to about 58 mmol/liter. In some embodiments, the hypohalite is used in a range from about 50 to about 56 mmol/liter. In some embodiments, the hypohalite is used in a range from about 50 to about 54 mmol/liter. In some embodiments, the hypohalite is used in a range from about 50 to about 52 mmol/liter. In some embodiments, the hypohalite is used in a concentration about 100 mmol/liter. In some embodiments, the hypohalite is sodium hypochlorite. In some embodiments, the hypohalite reagent range is + or −50% from the stated value disclosed herein.

In some embodiments, the alkali buffer is used in a range from about 0.5 to about 1.0 mol/liter. In some embodiments, the alkali buffer is used in a range from about 0.6 to about 1.0 mol/liter. In some embodiments, the alkali buffer is used in a range from about 0.7 to about 1.0 mol/liter. In some embodiments, the alkali buffer is used in a range from about 0.8 to about 1.0 mol/liter. In some embodiments, the alkali buffer is used in a range from about 0.9 to about 1.0 mol/liter. In some embodiments, the alkali buffer is used in a range from about 0.5 to about 0.9 mol/liter. In some embodiments, the alkali buffer is used in a range from about 0.5 to about 0.8 mol/liter. In some embodiments, the alkali buffer is used in a range from about 0.5 to about 0.7 mol/liter. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 1.0 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a range from about 0.5 to about 0.6 mol/liter. In some embodiments, the alkali buffer is used in a concentration about 0.5 mol/liter. In some embodiments, the alkali buffer is one or a combination of: calcium acetate, calcium chloride, zinc acetate, zinc chloride, or any equivalent mono, di, or tri, -valent salt thereof. In some embodiments, the alkali buffer is sodium/calcium acetate. In some embodiments, the alkali buffer is used in a concentration about 0.6 mol/liter. In some embodiments, the alkali buffer is used in a concentration about 0.7 mol/liter. In some embodiments, the alkali buffer is used in a concentration about 0.8 mol/liter. In some embodiments, the alkali buffer is used in a concentration about 0.9 mol/liter. In some embodiments, the alkali buffer is used in a concentration about 0.75 mol/liter.

| Indophenol Reagent | Reagent Concentration | Volume | Final Mixed Concentration accounting for sample volume (In Detection Vessel and Reagent Conduit) |
|---|---|---|---|
| Sodium Hypochlorite | About 0.175% | About 7 microliters | About 0.025% |
| Sodium Nitroprusside | About 400 to about 500 micrograms/mL | About 7 microliters | From about 58 to about 72.9 micrograms/mL |
| 2-phenylphenol | About 5 mg/mL | About 7 microliters | About 0.73 mg/mL |
| Sodium Hydroxide | 10 mg/mL | About 7 microliters | About 1.45 mg/mL |

In some embodiments, the ratio of volume of indophenol reagent to final volume of mixed solution should be 1/1.2. As an example, in some embodiments, 5 microliters of whole blood would result in a final reaction solution volume of 6 microliters, 10 microliters of blood would result in a final reaction volume of 12 microliters, and a 20 microliter sample of blood would result in a final reaction volume of 24 microliters.

The disclosure relates to a method of diagnosing liver dysfunction or hyperammonemia in a subject comprising:

(a) contacting a sample of the subject to a system, cartridge, test strip, biosensor or device disclosed herein;

(b) detecting the presence, absence, or quantity of ammonia;

(c) correlating the quantity of ammonia to the levels of amino acid in the sample;

(d) diagnosing the subject as having liver dysfunction or hyperammonemia if the ammonia levels are quantified as above about 100 micromoles/liter of sample.

The disclosure relates to a method of diagnosing liver dysfunction or hyperammonemia in a subject comprising:

(a) contacting a sample of the subject to a system, cartridge, test strip, biosensor or device disclosed herein;

(b) detecting the presence, absence, or quantity of ammonia;

(c) correlating the quantity of ammonia to the levels of amino acid in the sample;

(d) diagnosing the subject as having liver dysfunction or hyperammonemia if the ammonia levels are quantified as above about 90 micromoles/liter of sample.

The disclosure relates to a method of diagnosing liver dysfunction or hyperammonemia in a subject comprising:

(a) contacting a sample of the subject to a system, cartridge, test strip, biosensor or device disclosed herein;

(b) detecting the presence, absence, or quantity of ammonia;

(c) correlating the quantity of ammonia to the levels of amino acid in the sample;

(d) diagnosing the subject as having liver dysfunction or hyperammonemia if the ammonia levels are quantified as above about 80 micromoles/liter of sample.

The disclosure relates to a method of diagnosing liver dysfunction or hyperammonemia in a subject comprising:

(a) contacting a sample of the subject to a system, cartridge, test strip, biosensor or device disclosed herein;

(b) detecting the presence, absence, or quantity of ammonia;

(c) correlating the quantity of ammonia to the levels of amino acid in the sample;

(d) diagnosing the subject as having liver dysfunction or hyperammonemia if the ammonia levels are quantified as above about 70 micromoles/liter of sample.

A method of treating a subject with liver dysfunction or hyperammonemia comprising:

(a) contacting a sample of the subject to a system, cartridge, test strip, biosensor or device disclosed herein;

(b) diagnosing the subject as having liver dysfunction or hyperammonemia if the ammonia levels are quantified as above about 70 micromoles/liter of sample; and (c) treating the subject by administering therapeutically effective amounts of steroids, arginine supplements, sodium benzoate, phenylacetate, and/or a glucose solution.

A method of treating a subject with liver dysfunction or hyperammonemia comprising:

(a) contacting a sample of the subject to a system, cartridge, test strip, biosensor or device disclosed herein;

(b) diagnosing the subject as having liver dysfunction or hyperammonemia if the ammonia levels are quantified as above about 80 micromoles/liter of sample; and (c) treating the subject by administering steroids, arginine supplements, sodium benzoate, phenylacetate, and/or a glucose solution.

A method of treating a subject with liver dysfunction or hyperammonemia comprising:

(a) contacting a sample of the subject to a system, cartridge, test strip, biosensor or device disclosed herein;

(b) diagnosing the subject as having liver dysfunction or hyperammonemia if the ammonia levels are quantified as above about 90 micromoles/liter of sample; and (c) treating the subject by administering steroids, arginine supplements, sodium benzoate, phenylacetate, and/or a glucose solution.

A method of treating a subject with liver dysfunction or hyperammonemia comprising:

(a) contacting a sample of the subject to a system, cartridge, test strip, biosensor or device disclosed herein;

(b) diagnosing the subject as having liver dysfunction or hyperammonemia if the ammonia levels are quantified as above about 100 micromoles/liter of sample; and (c) treating the subject by administering steroids, arginine supplements, sodium benzoate, phenylacetate, and/or a glucose solution.

In any of the above methods, the method comprises detecting the ammonia or ammonium ion levels in whole blood, water, or a sample taken from a microenvironment such as a test solution reconstituted from a swab taken from a microenvironment.

The disclosure relates to a method of diagnosing a metabolic disorder in a subject comprising:

(a) contacting a sample of the subject to a system, cartridge, test strip, biosensor or device disclosed herein;

(b) detecting the presence, absence, or quantity of ammonia;

(c) correlating the quantity of ammonia to the levels of amino acid in the sample;

(d) diagnosing the subject as having a metabolic disorder if the amino acid levels are quantified as above those levels set forth in Table 1.

In some embodiments, any methods disclosed herein comprises taking multiple steps of detecting the presence, absence, or quantity of ammonia in a sample by performing 1, 2, 3, or more tests simultaneously or in series.

In some embodiments, the step of detecting the presence, absence, or quantity of ammonia comprises detecting the wavelength emitted or absorbed by a indophenol reaction product. In any of the above methods, the step of detecting the presence, absence, or quantity of ammonia comprises detecting the wavelength emitted or absorbed by a indophonel reaction product by looking at the visible light in one or more vessels. In some embodiments, the step of detecting the presence, absence, or quantity of ammonia comprises detecting the wavelength absorbed by a indophenol reaction product wherein the wavelength from about 500 nm to about 700 nm.

In some embodiments, any of the above methods, the step of detecting the presence, absence, or quantity of ammonia comprises detecting the wavelength emitted or absorbed by a indophonel reaction product. In some embodiments, any of the above methods, the step of detecting the presence, absence, or quantity of ammonia comprises the step of using a fingerstick to extract blood from a subject wherein the method does not comprise a step of swiping the finger with a swab, wipe, or pad of alcohol, detergent, or iodine. In some embodiments, the methods comprise pre-wiping the subject with a wipe, swab, or pad step of saline solution wiping at the portion of the blood draw prior to extracting blood from the patient an contacting it to the test strip, device, chip or solid support described herein. I would say you can use a ratio of 1.2 for blood to final solution volume.

In some embodiments, any of the above methods do not comprise a step of converting liquid to a gas or any step involving gas chromatography.

In some embodiments, any of the above biosensor cartridges, devices, or methods comprise mixing a volume of any of the reagents disclosed herein in a volume of from about 10 microliters to about 150 microliters. In some embodiments, any of the above biosensor cartridges, devices, or methods comprise comprise mixing a volume of any of the reagents disclosed herein in a volume of from about 10 microliters to about 100 microliters. In some embodiments, any of the above biosensor cartridges, devices, or methods comprise a volume of any of the reagents disclosed herein in a volume of from about 10 microliters to about 150 microliters. In some embodiments, any of the above biosensor cartridges, devices, or methods comprise a volume of any of the reagents disclosed herein in a volume of about 10 microliters. In some embodiments, any of the above biosensor cartridges, devices, or methods comprise a volume of any of the reagents disclosed herein in a volume of about 9 microliters. In some embodiments, any of the above biosensor cartridges, devices, or methods comprise a volume of any of the reagents disclosed herein in a volume of about 8 microliters. In some embodiments, any of the above biosensor cartridges, devices, or methods comprise a volume of any of the reagents disclosed herein in a volume of about 7 microliters. In some embodiments, any of the above biosensor cartridges, devices, or methods comprise a volume of any of the reagents disclosed herein in a volume of about 6 microliters. In some embodiments, any of the above biosensor cartridges, devices, or methods comprise a volume of any of the reagents disclosed herein in a volume of about 20 microliters. In some embodiments, any of the above biosensor cartridges, devices, or methods comprise a volume of any of the reagents disclosed herein in a volume of about 30 microliters. In some embodiments, any of the above biosensor cartridges, devices, or methods comprise a volume of any of the reagents disclosed herein in a volume of about 40 microliters. In some embodiments, any of the above biosensor cartridges, devices, or methods comprise a volume of any of the reagents disclosed herein in a volume of about 50 microliters.

In some embodiments, the disclosure relates to a computer-implemented method of quantifying ammonia or ammonium ions and/or amino acid concentration in a sample.

In some embodiments, the disclosure relates to a system comprising a processor that performs a computer-implemented method of quantifying amino acid concentration in a sample of a subject. In some embodiments, the system comprises a processor optionally located at a remote location and accessible by internet connection, operably connected to a computer storage memory that stores subject's concentration values over time. In some embodiments, the subject or the subject's healthcare provider may accesses the internet to communicate with a server linked to the computer storage memory. Subject data reports may be generated and obtained by the subject after initiating a retrieve command through the processor. In some embodiments, the system comprises a computer program-product that performs a function convert current signals generated by a biosensor disclosed herein to concentration of a particular amino acid and/or ammonia in a sample. In some embodiments, the disclosure relates to a system including at least one processor and a computer readable memory, said computer readable memory having stored thereon program code for quantifying amino acid concentration in a sample of bodily fluid comprising: means for storing data associated with a subject; means for, responsive to receiving a level of current response from a biosensor or its computer storage memory, presenting a concentration value to a user as part of a user interface. In some embodiments, the user is the subject or healthcare provider of the subject. In some embodiments, the disclosure relates to a system that comprises at least one processor, a program storage, such as memory, for storing program code executable on the processor, and one or more input/output devices and/or interfaces, such as data communication and/or peripheral devices and/or interfaces. In some embodiments, the user device and computer system or systems are communicably connected by a data communication network, such as a Local Area Network (LAN), the Internet, or the like, which may also be connected to a number of other client and/or server computer systems. The user device and client and/or server computer systems may further include appropriate operating system software.

The present disclosure relates generally to definition and/or use of concentration values that characterize a subject's modification of behavior. In some embodiments, the concentration values corresponding to the concentration of amino acids in a sample of bodily fluid may characterize the degree to which a subject is advised to modify a diet or seek medical treatment.

In some embodiments, the present disclosure provides biosensors or test strips for use in diagnostic assays. In some embodiments the biosensor and/or test strips are provided as part of a diagnostic or detection kit. In certain embodiments, kits for use in accordance with the present disclosure may include one or more reference samples; instructions (e.g., for processing samples, for performing tests, for interpreting results, etc.); media; and/or other reagents necessary for performing tests.

The disclosure provides a test strip comprising: a solid support, a at least a first vessel in fluid communication with at least one conduit, wherein the test strip comprises a hydrogel disclosed herein. In some embodiments, the solid support is a slide optionally coated with a polymer. In some embodiments, the solid support is coated with a polymer. In some embodiments, the polymer is polyacrylamide. In some embodiments, the solid support is a material chosen from: polysterene (TCPS), glass, quarts, quartz glass, poly(ethylene terephthalate) (PET), polyethylene, polyvinyl difluoride (PVDF), polydimethylsiloxane (PDMS), polytetrafluoroethylene (PTFE), polymethylmethacrylate (PMMA), polycarbonate, polyolefin, ethylene vinyl acetate, polypropylene, polysulfone, polytetrafluoroethylene, silicones, poly(meth)acrylic acid, polyamides, polyvinyl chloride, polyvinylphenol, and copolymers and mixtures thereof. In some embodiments, the test strip is a paper product. In some embodiments, the at least one electrode is attached to the solid support.

According to some embodiments, the disclosure provides a software component or other non-transitory computer program product that is encoded on a computer-readable storage medium, and which optionally includes instructions (such as a programmed script or the like) that, when executed, cause operations related to the calculation of amino acid concentration values. In some embodiments, the computer program product is encoded on a computer-readable storage medium that, when executed: quantifies one or more ammonia or ammonium ion concentration values; normalizes the one or more ammonia or ammonium ion concentration values over a control set of data; creates an amino acid profile or signature of a subject; and displays the profile or signature to a user of the computer program product. In some embodiments, the computer program product is encoded on a computer-readable storage medium that, when executed: calculates one or more ammonia or ammonium ion concentration values, normalizes the one or more ammonia or ammonium ion concentration values, and creates an amino acid signature, wherein the computer program product optionally displays the amino acid signature and/or one or more ammonia or ammonium ion concentration values on a display operated by a user. In some embodiments, the disclosure relates to a non-transitory computer program product encoded on a computer-readable storage medium comprising instructions for: quantifying one or more ammonia or ammonium ion concentration values; and displaying the one or more ammonia or ammonium ion concentration values to a user of the computer program product.

In some embodiments, the step of calculating one or more ammonia or ammonium ion concentration values comprises quantifying an average and standard deviation of counts on replicate trials of contacting the device or test strip with one or more samples of bodily fluids.

In some embodiments, the one or more hydrogel coated electrodes are attached to a solid phase support. In some embodiments, a solid phase support comprises any solid or semi-solid surface. In some embodiments, a solid phase comprises any traditional laboratory material for growing or maintaining cells in culture including petri dishes, beakers, flasks, test tubes, microtitre plates, and/or culture slides. In some embodiments, a solid phase comprises a glass slide, a plastic slide, a paper test strip, or combination thereof.

In some embodiments, the one or more hydrogel coated electrodes are attached to discrete addressable sites on a solid phase support. In some embodiments, a solid phase support comprises polyamides, polyesters, polystyrene, polypropylene, polyacrylates, polyvinyl compounds (e.g. polyvinylchloride), polycarbonate, polytetrafluoroethylene (PTFE), nitrocellulose, cotton, polyglycolic acid (PGA), cellulose, dextran, gelatin, glass, fluoropolymers, fluorinated ethylene propylene, polyvinylidene, polydimethylsiloxane, polystyrene, silicon substrates (such as fused silica, polysilicon, or single silicon crystals) or combinations thereof.

In some embodiments, the disclosure relates to a catalogue of medical records relating to a subject comprising test results from the one or plurality of methods described herein. Such catalogue, in some embodiments, being stored on a computer readable medium being accessible remotely through a wireless internet connection.

As described above, certain embodiments of the present disclosure may be used to distinguish between samples of bodily fluid obtained from a subject who does or is suspected of having an hyperammonemia and a subject who does not have a metabolic disease. This system is potentially useful, for example, when testing whole blood samples of a subject to determine whether disease is present. Diagnosing a patient using one or more ammonia or ammonium ion concentration values would include, for example, comparing one or more ammonia or ammonium ion concentration values of a sample from a subject with the measured reference values or threshold values of a subject.

The disclosure also relates to methods of treating or preventing a metabolic disease comprising:

(a) contacting a sample of bodily fluid to the to the biosensor, system, test strip, chip or solid support disclosed herein;

(b) quantifying one or more concentration values of ammonia in the sample;

(c) comparing the one or more concentration values of ammonia in the sample to a threshold value of ammonia concentration identified as being in a healthy range; and (d) identifying the subject as having a metabolic disease if the one or more concentration values of ammonia in the sample exceed or fall below the threshold value; and (e) administering a therapeutically effective amount of a therapeutic agent to treat metabolic disease.

In some embodiments, the metabolic disease is hyperammonemia. In some embodiments, the therapeutic agent is glycerol phenylbutyrate or a salt thereof. In some embodiments, the therapeutic agent is Ravicti®.

Kits

In some embodiments, kits in accordance with the present disclosure may be used to quantify amino acid concentration is samples of bodily fluid.

The disclosure further provides for a kit comprising one or a plurality of containers that comprise one or a plurality of the polypeptides or fragments disclosed herein. In some embodiments, the kit comprises a test strip and/or a biosensor comprising a test strip, or any animal-based derivative of serum that enhances the culture or proliferation of cells. In some embodiments, the kit comprises: a biosensor disclosed herein, any test strip disclosed herein, and a computer program product disclosed herein optionally comprising instructions to perform any one or more steps of any method disclosed herein. In some embodiments, the kit does not comprise cell media. In some embodiments, the kit comprises a solid support comprising a membrane disclosed herein and/or embedded with at least one electrode disclosed herein optionally comprising any one or combination of a hypohalite, an aqueous basic solution, and at least one compound comprising a phenyl group in one or a a plurality of containers. In some embodiments, the kit comprises a device to affix a hydrogel to a solid support.

The kit may contain two or more containers, packs, or dispensers together with instructions for preparation of an array. In some embodiments, the kit comprises at least one container comprising the biosensor or system described herein and a second container comprising a solution for maintenance, use, and/or storage of the biosensor such as storage buffer. In some embodiments, the kit comprises a composition comprising any molecule disclosed herein in solution or lyophilized or dried and accompanied by a rehydration mixture. In some embodiments, the molecules and rehydration mixture may be in one or more additional containers. In some embodiments, the kit comprises a composition comprising any one or combination of The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

The kit may contain a biosensor described herein and/or a test strip comprising ahypohalite, an aqueous basic solution, and at least one compound comprising a phenyl group. The kit may also contain a sold support such as a test strip comprising any membrane disclosed herein.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The disclosure also provides a kit comprising: a biosensor comprising: a solid support and a plurality of electrodes, wherein at least one electrode comprises a hydrogel disclosed herein. in some embodiments, the hydrogel comprises an immobilized metabolic enzyme or a functional fragment thereof; and optionally comprising at least one vessel comprising a hyohalite, an aqueous basic buffer, in liquid or solid phase, and at least one compound comprising a phenyl group. In some embodiments, the kit further comprises at least one of the following: a sample, and a set of instructions, optionally accessible remotely through an electronic medium.

Generally referring to FIGS. 6-13, a system, method, and apparatus for point of care hyperammonemia sensors may be described. In the exemplary embodiments described by the figures, samples may be tested for ammonia levels, amino acid levels, or other compound levels by being in concert with certain reagents to utilize an indophenol reaction. Color change in the reaction may be measured and correspond to certain concentrations of specific compounds and molecules by manual comparison to an extensive color-matching sheet or automated electronic analysis with the use of calibration curves.

Figure 6:
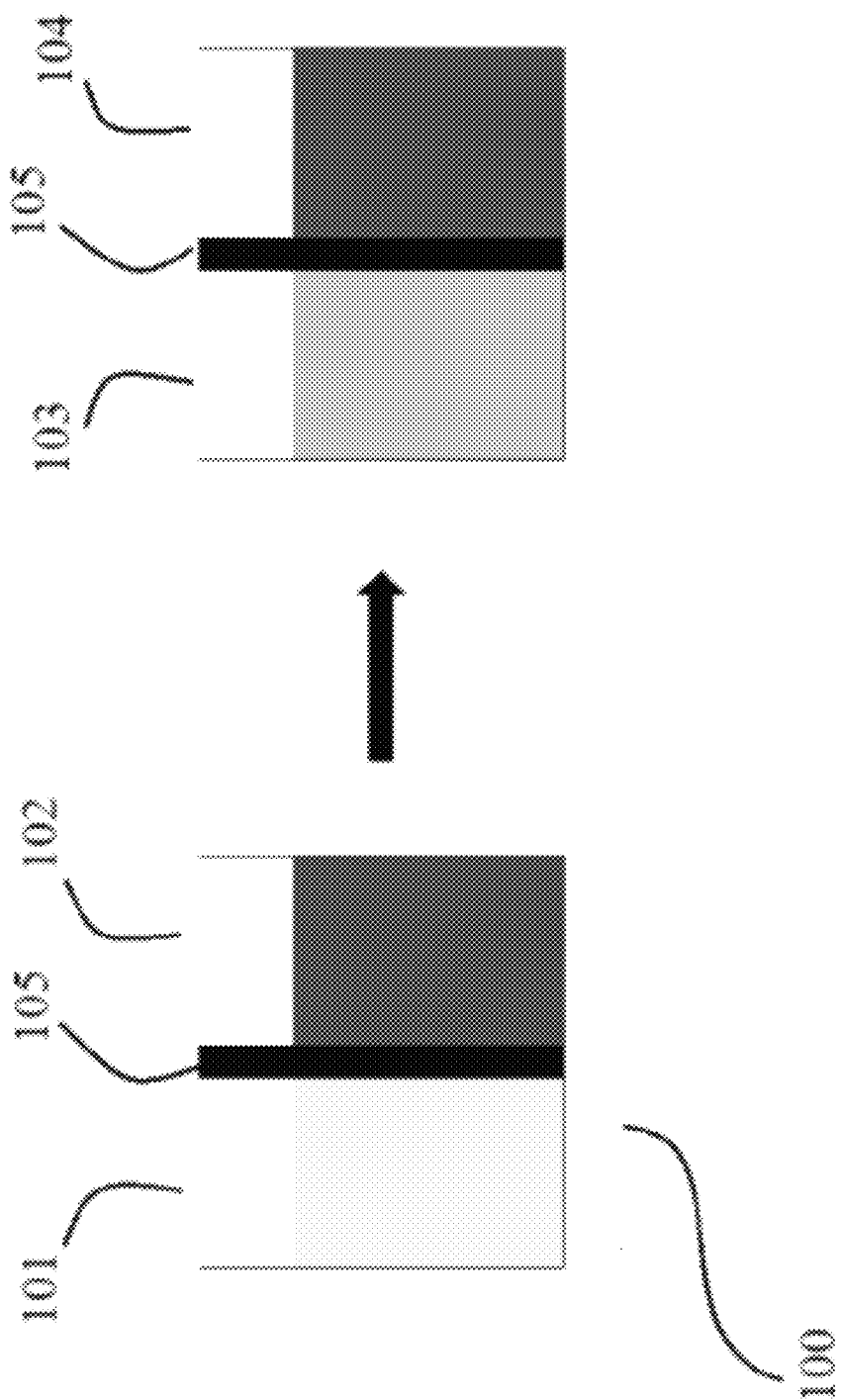
FIG. 6 is an exemplary view of a system having the ability to detect ammonia or ammonium ion levels in a given sample applied to a first and second vessel separated by a membrane positioned at an fluid exchange opening.

FIG. 6 shows one exemplary embodiment of a system demonstrating the ability to detect ammonia levels in various samples. A well 100 may be made of plastic, wood, metal, composite materials, or a combination thereof. Additionally, well 100 may be comprised of synthetic compounds or polymers, such as silicone. Well 100 may further be divided into two or more sections, and may be separated by a membrane filter 105 interposed in or near the center of well 100. Membrane filter 105 may be made of a cation exchange filter such as Nafion, or similar perfluorinated ionomers to allow for only the passage of small positively charged and neutral molecules between sections. Therefore, membrane filter 105 may be selected to allow for the passage of various molecules or biological components based on charge, size, or similar characteristics. Other membrane filters may consequently be used for desired functionality, such as acrylamide, poly(ethylene glycol) diacrylate, poly(2-hydroxylethyl methacrylate), poly(vinyl alcohol), or other similar polymeric hydrogels. The selection of membrane filter 105 for a hyperammonemia sensor may depend on the membranes ability to allow for the passage of molecules such as ammonia, and the ability to limit the passage of proteins, amino acids, and other molecules or compounds.

Still referring to FIG. 6, reagent section 101 may contain reagents such as phenol, 2-phenylphenol, sodium salicylate, other phenolic reagents or polymers, or a combination thereof. Further, reagent section 101 may also contain bleach, hypochlorite, chloramine T, a similar anion, or a combination thereof, catalysts such as nitroprusside, and a basic buffer such sodium hydroxide or potassium hydroxide to maintain alkali conditions. Sample section 102 may contain serum, blood, plasma, or other liquid desired to be tested. Membrane filter 105 may only allow the passage of ammonia from section 102 to section 101. A chemical reaction, described in FIG. 8, may take place upon reception of ammonia or similar molecule into section 101, turning the reagents a blue color, as shown in section 103. Section 104 may describe the tested sample after the reaction takes place. Color sheets may be available for a qualitative comparison between colors representing specific ammonium concentrations.

In order for the cation exchange membrane, such as Nafion, to be useable for this application, a certain washing procedure and method may be disclosed. The membrane may be washed in a hydrogen peroxide aqueous solution, which may be at boiling temperatures. Additionally, the membrane may be washed in deionized water, ethylenediaminetetraacetic acid or other chelating agents, sulfuric acid, and other similar aqueous materials. The membrane may be exposed to extreme temperatures and pressures to further ensure washing.

Figure 7:
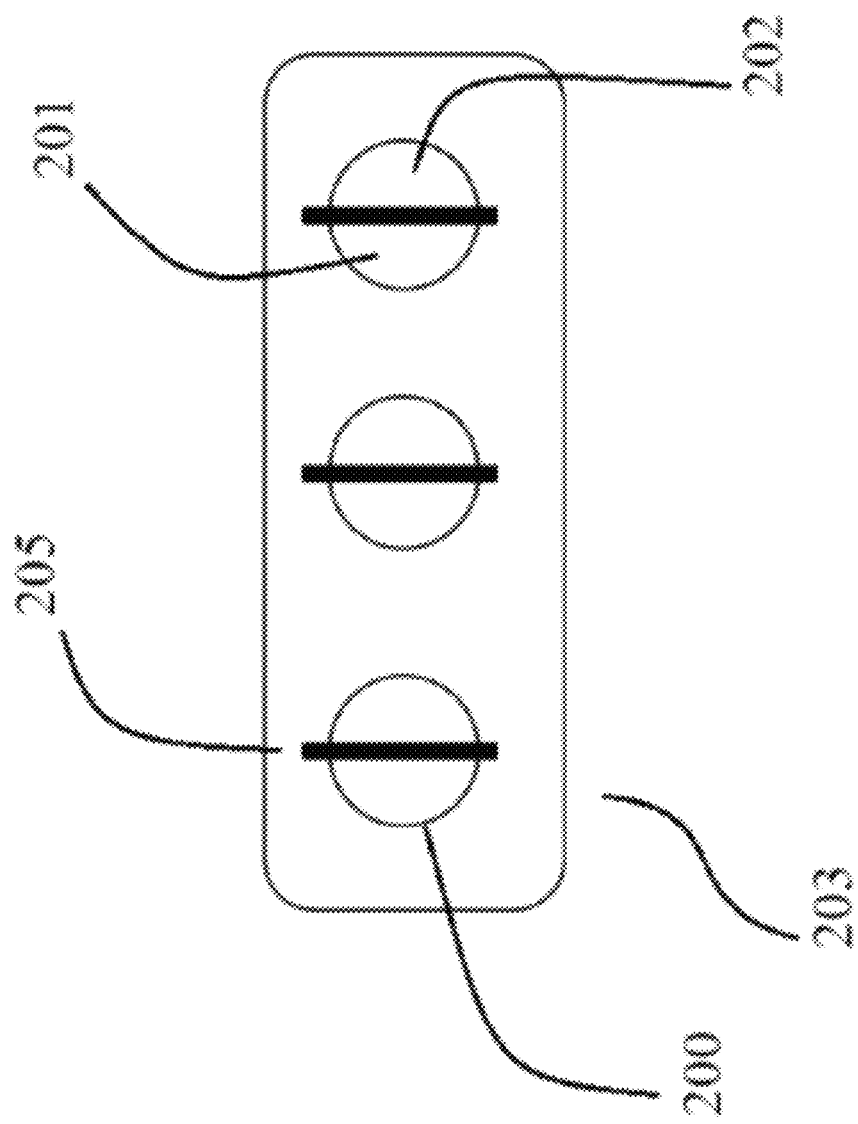
FIG. 7 is an exemplary view of a system comprising multiple vessels within which more than one indophenol reaction mat be performed in parallel.

FIG. 7 shows an embodiment of a device fitted with multiple wells. Wells 200 may be depressions or fossa in a mounting plate 203. Mounting plate 203 may be comprised of plastic, wood, metals, composite materials, or a combination thereof. Additionally, mounting plate 203 may be comprised of synthetic compounds or polymers, such as silicone. As shown, mounting plate 203 carries three wells 200, yet those skilled in the art may appreciate the ability for a mounting plate 203 to carry substantially more or fewer wells as desired. Membrane filter 205 may be made of Nafion or similar membranes, and may be disposed of in any angle, such as a vertical placement as shown in FIG. 7, a horizontal placement, or a different angle as desired. Reagent section 201 may be filled with phenol, 2-phenylphenol, other phenolic reagents, or a combination thereof; bleach, hypochlorite, chloramine T, a similar anion, or a combination thereof; sodium hydroxide, potassium hydroxide, or a similar basic buffer to maintain alkali conditions; and one or more catalysts, such as nitroprusside. Sample section 202 may be filled with serum, blood, plasma, or similar material desired to be tested. The various wells 200 may be interconnected to facilitate the fluid flow between respective sections in order to test samples multiple times to further accuracy, or to test samples with multiple different membrane filters or reagents. Generally, if sample section 202 contains sufficient levels of ammonia, the ammonia may diffuse through membrane filter 205 and into reagent section 202, which may allow the reaction to be described in FIG. 8 to take place.

Figure 8:
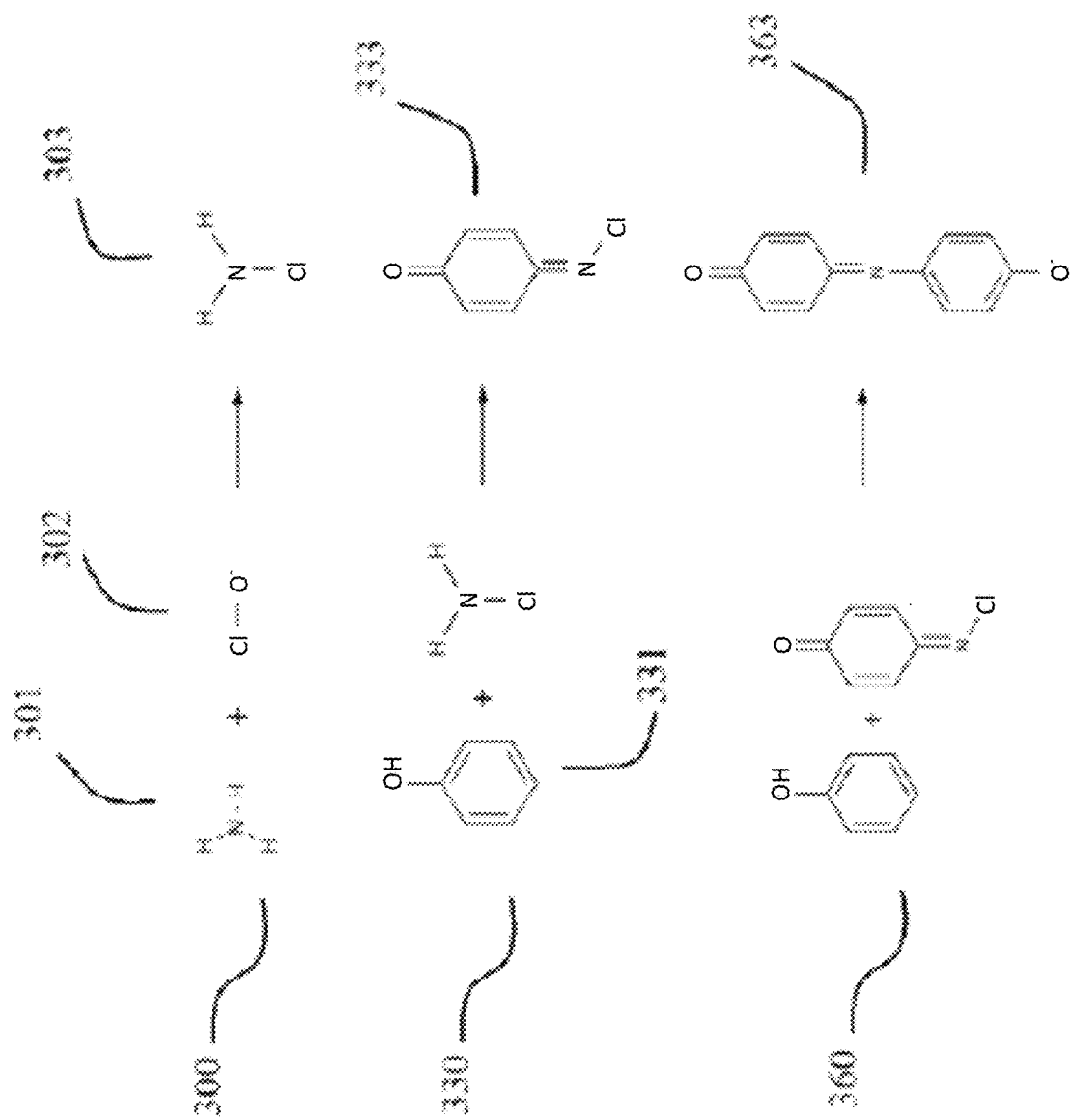
FIG. 8 shows exemplary reaction otherwise known as Berthelot's Reaction or an indophenol reaction.

FIG. 8 shows exemplary reactions that may take place in a point of care hyperammonemia sensor, sometimes known as an indophenol reaction or Berthelot's Reaction. Reactions 300, 330, and 360 may take place upon diffusion of ammonia from one section of a well to another through a membrane filter, as described in FIGS. 6-7. Anion 302 may be hypochlorite, as shown, bleach, calcium hypochlorite, sodium hypochlorite, or other similar anions. Anion 302 may then react with ammonia 301, and produce chloramine 303, or similar ammonia derivative. Chloramine 303 may then react with further reagents, such as phenol 331. A phenol-cholarmine intermediate 333 may further react with additional phenol 331 molecules, producing indophenol 363 which may appear visibly blue in color. Phenol 331 may also be replaced with 2-phenylphenol for further efficacy, with other phenolic reagents such as sodium salicylate, with phenol polymers, or with a combination thereof. The color change in the reagent section of the well or depression may demonstrate the presence of ammonia in the sample section.

Figure 9:
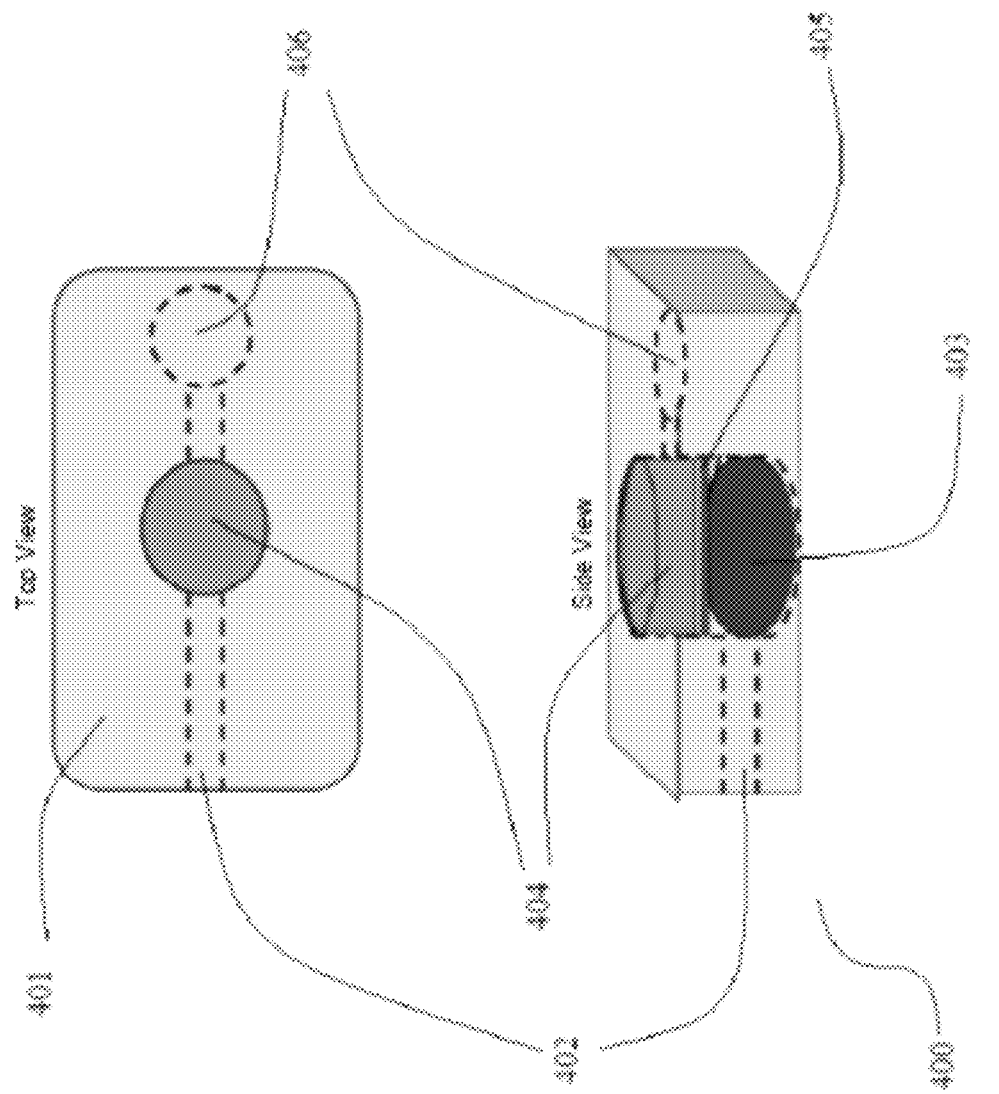
FIG. 9 shows an exemplary embodiment of a microfluidic testing device.

FIG. 9 shows a further exemplary embodiment of a testing device, comprising of a microfluidic. The microfluidic 400 may be suitable for home use in a similar fashion to blood glucose meters to provide ongoing, rapid, reliable testing for hyperammonemia, various aminoacidopathies, and other similar applications. The device 401 may be manufactured of plastic, wood, metal, composites, or a combination thereof, or a synthetic polymer or compound, such as silicone. A user may use a lancet to excrete a small amount of blood from the tip of a finger or other location on the body, and apply a small amount of blood, serum, plasma, or similar component at opening of a conduit channel 402. The sample may be transported through conduit channel 402 by capillary action and reach sample section 403. Sample section 403 may be separated from reagent section 404 by a cation exchange membrane 405, such as Nafion, whereby allowing ammonia to diffuse through membrane 405 into reagent section 404. Prior to the application of a blood sample, a squeezable reservoir 406 containing either dry or liquid bleach, hypochlorite, chloramine T, or similar anion may be manually or electronically stimulated, allowing for the flow of bleach into interposed reagent section 404. The bleach may be separate from reagents in reagent section 404 to ensure accurate and timely chemical reactions. Reagent section 404 may contain liquid or dry components of reagents disclosed in FIGS. 6-8, such as phenol, 2-phenylphenol, other phenolic reagents, or a combination thereof; sodium hydroxide, potassium hydroxide, or a similar basic buffer to maintain alkali conditions; and may also contain one or more catalysts, such as nitroprusside. Upon the presence of a certain level of ammonium in the sample, the reagent section 404 may turn into a blue color, which may be compared to a separate or included color schematic for the user to identify.

Still referring to FIG. 9, the microfluidic 400 may be used multiple times or manufactured to be a single-use device. Additionally, changes may be implemented to the design and range of chemicals used to determine amino acid levels in samples. Those skilled in the art may also appreciate the ability for a device or similar device to conform to various biological or non-biological samples, such as saliva, urine, waste water, or perhaps various chemicals to be used in a laboratory or medical setting.

In addition to the qualitative methods of determining presence or levels of ammonia in applicable samples, a quantitative apparatus, system, and method may be disclosed.

Figure 10:
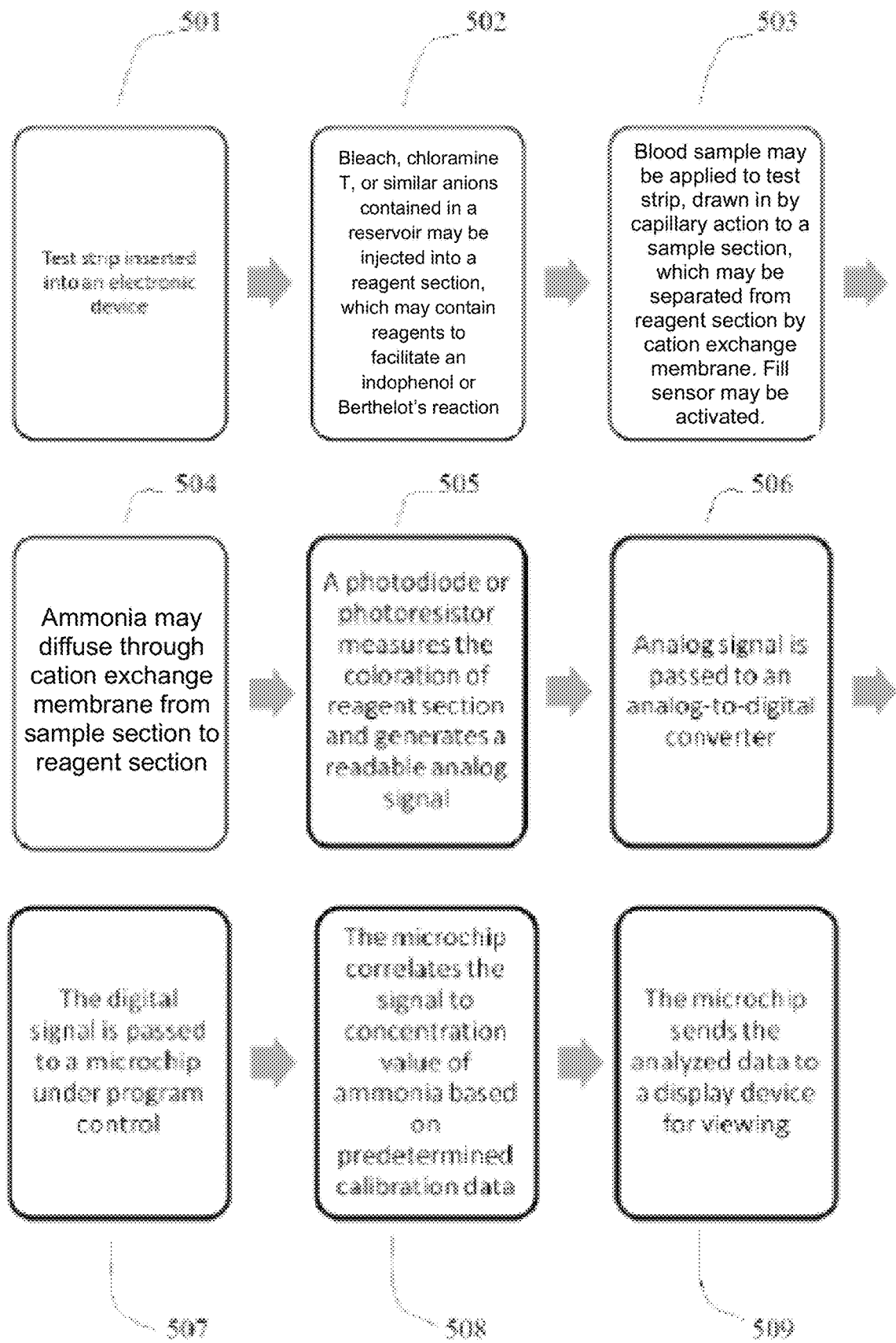
FIG. 10 shows an exemplary flowchart for a method of quantitative point of care hyperammonemia sensing using embodiments of the disclosure.
Figure 11:
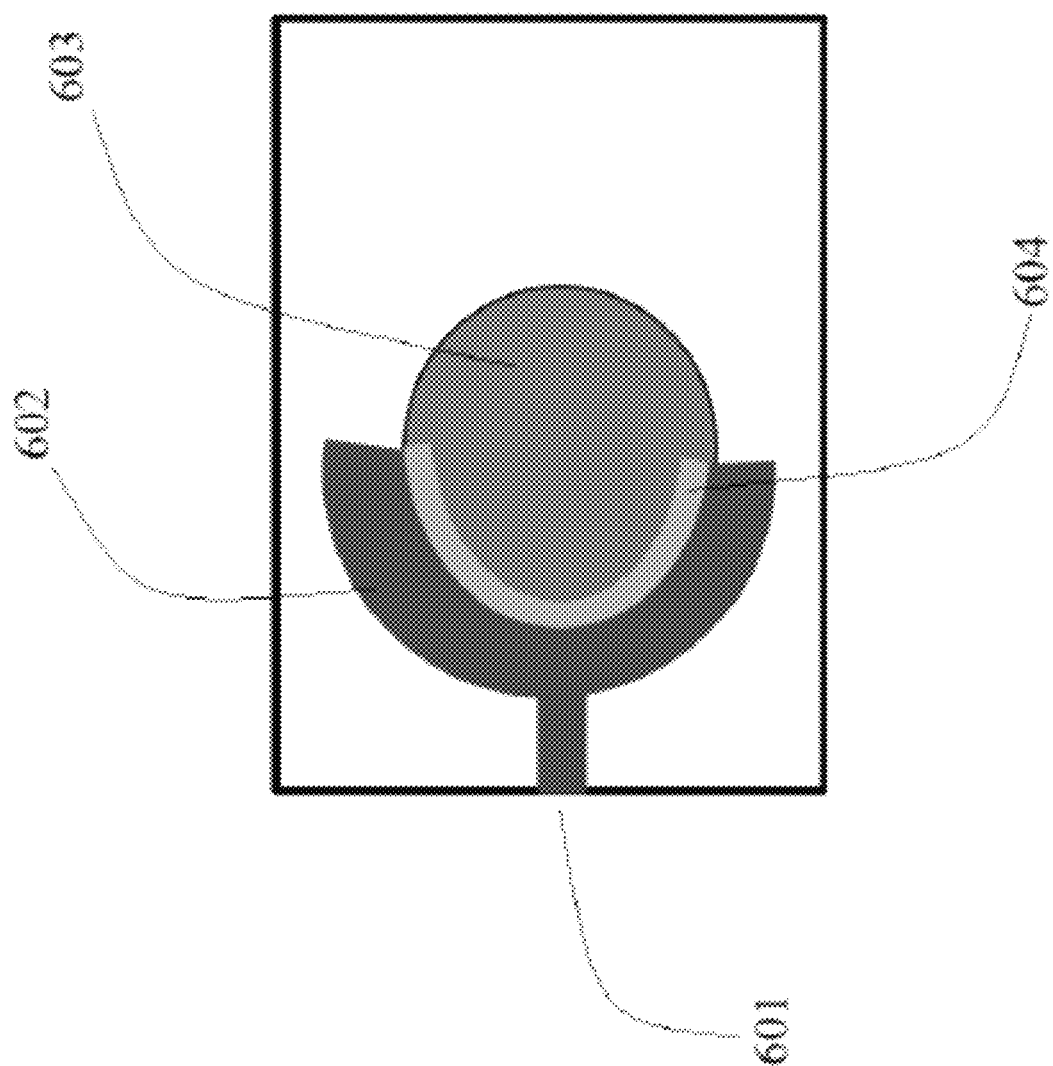
FIG. 11 shows an exemplary embodiment of a blood test strip for use with an electronic testing device.
Figure 12:
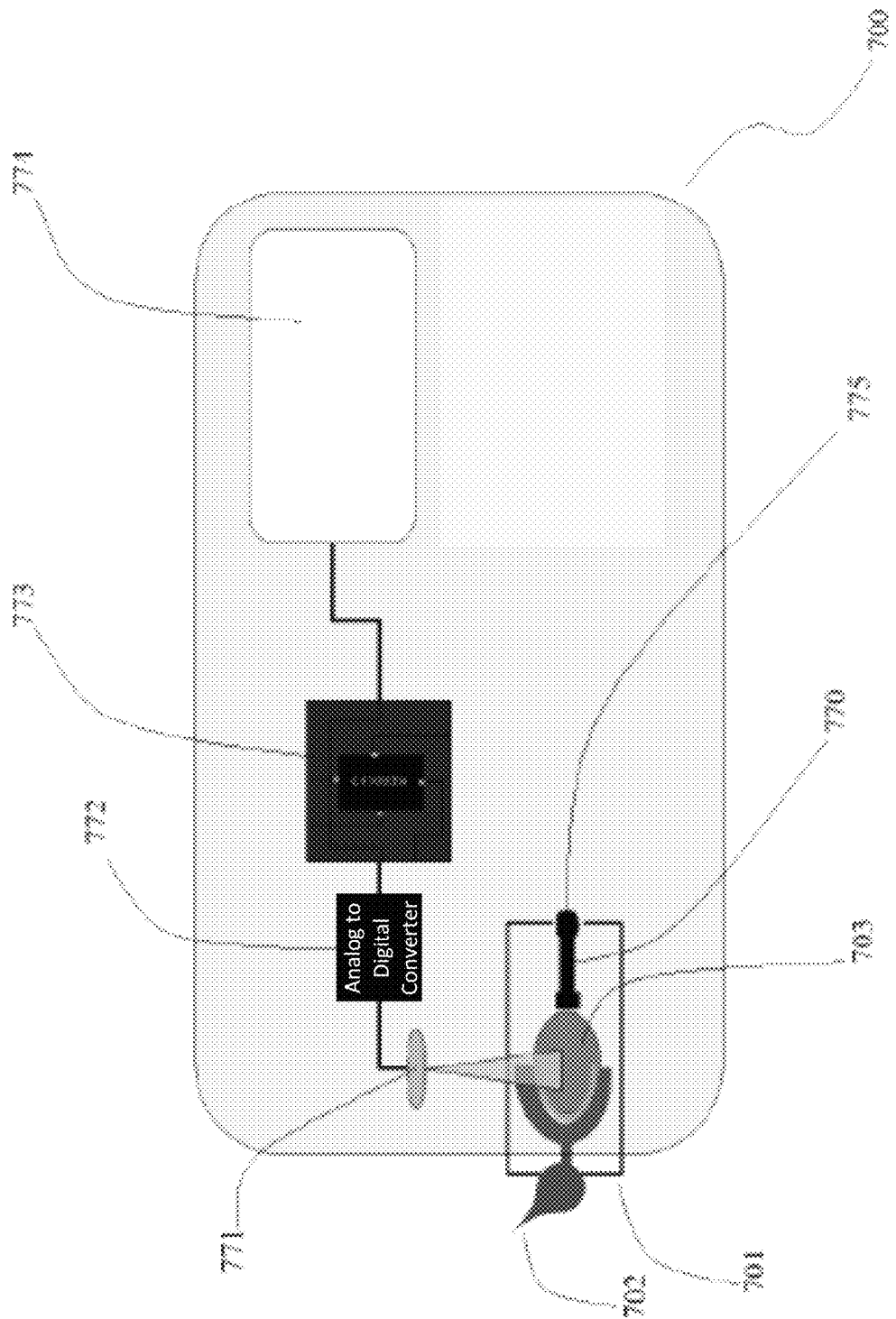
FIG. 12 shows an exemplary embodiment of a device comprising an electronic circuit comprising an electrode exposed to a vessel configured for performance of the indophenol reaction; an analog to digital convertor, a microchip in electronic communication with a display.
Figure 13:
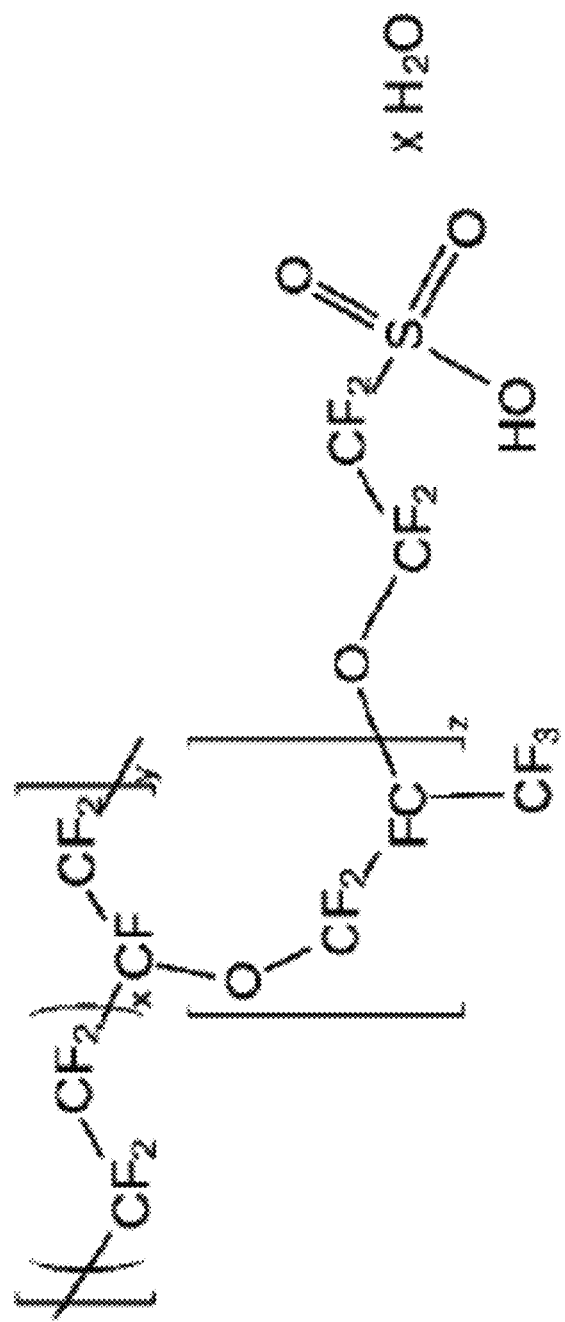
FIG. 13 shows the chemical composition of Nafion.

FIG. 10 shows an exemplary flowchart of a sequence of events that may take place to accurately and quantitatively identify the amount of ammonia in a sample, and is closely related to the exemplary apparatus and system disclosed in FIGS. 11-12. Additionally, those skilled in the art may appreciate that quantitative analysis in this, or a similar fashion, be added to any of the apparatuses or systems disclosed in FIGS. 5-8.

FIG. 10 therefore shows an exemplary flowchart of steps for a quantitative point of care hyperammonemia sensor. It may be appreciated that these steps may be interchangeable chronologically, may be altered significantly, or eliminated while receiving similar results. Block 501 may refer to a test strip of any size, similar to sizing of the testing strips of blood glucose meters. The insertion mechanism block 501 test strip may be manual or automated. Upon insertion into a device, block 502 may further disclose the initiation of a series of events that may take place under program control. A bleach reservoir may be opened, manually or automatically, into a reagent section within the device. The reagent section, sample section, or both may contain reagents necessary for an indophenol reaction, or reagents used for diagnosing aminoacidopathies or similar diseases and conditions. Block 503 may further disclose the application of a blood sample by way of lancet excretion. The blood sample may be substituted for other biological samples, which may then be transported through a conduit channel to a sample section separated by a reagent section by a cation exchange membrane, such as Nafion. Block 503 may further initiate a microchip under program control which may serve as a timing device, allowing for consistent timing between various steps. This microchip may direct a photodiode or photoresistor to remain inactive for a desired duration to allow for an adequate period of time for certain reactions to take place.

Still referring to FIG. 10, Block 504 may further disclose the diffusion of ammonia or similar compound from sample section to reagent section to initiate any reaction. After a determined period of time, the reagent section may turn blue in the presence of ammonia. The degree of coloration may be dependent on the amount of ammonia in the sample section, which will allow for accurate quantitative analysis. Block 505 may further disclose the initiation of a photodiode or photoresistor near the reagent section to measure the degree of coloration. The photodiode or photoresistor may change the current of the system based on the coloration, whereby block 506 may disclose the step of converting photodiode or photoresistor signal from an analog to a digital signal. Block 507 may further disclose the reception of a digital signal to a microchip under program control. Upon reception, a microchip of block 507 may utilize a predetermined calibration curve in order to correlate a signal to an accurate ammonia concentration value, as further disclosed in block 508. Block 509 may further disclose a transmission of data from the microchip to a display device, which may be either physically or wirelessly connected to microchip, for user accessibility. This method may include the use of fewer or significantly more microchips and controllers under additional program control. Further microchips may be useful for various tests, display mechanisms, data analysis, and both visual and auditory aesthetics. Microchips may also facilitate communication between an exemplary device and an at-home computer, cell phone, TV, or other common display and communication devices.

FIG. 11 shows an exemplary embodiment of a blood test strip for use with an electronic device further disclosed in FIG. 12. The testing strip may be large or small in nature, for use in either laboratory settings or personal home use. Conduit channel 601 may be the reception point of a sample to be tested. A blood droplet, excreted by lancet, may be placed on distal edge of conduit channel 601, where capillary action may transport sample into sample section 602. Sample section 602 may be U-shaped to increase surface area with a cation exchange membrane 604, such as Nafion. On the opposing side of membrane 604, a reagent section 603 may be filled with reagents commonly used with an indophenol or Berthelot's reaction. Bleach, or a similar anion, may be located in a separated reservoir either on the testing strip or within the electronic device in order to ensure the reactivity of certain reagents.

FIG. 12 shows an exemplary embodiment of a testing device under program control and a display device for the presentation of quantitative analysis. A blood test strip 701, such as a strip disclosed in FIG. 11, may be inserted into a port or aperture located on testing device 700, and a blood droplet 702 may be dispensed onto a conduit located distally on blood test strip 701. Upon insertion, an injection mechanism 770 may either automatically or manually add bleach or a similar anion to a reagent section 703. Bleach, chloramine T, or similar dry or liquid anion may be stored in reservoir 775, and may be refillable as desired. A photodiode or photoresistor 771 may remain inactive for a predetermined period of time until a fill sensor within microchip 773 directs the photodiode or photoresistor to generate a signal corresponding to the coloration of reagent section 703. Photodiode or photoresistor 771 may then alter the current or voltage of the system with or without the means of an instrumentational amplifier and emit a signal sent to an analog-to-digital converter 772. Upon conversion to a digital signal, this may be sent to microchip 773 for analysis and further program control. Microchip 773 may compute signal and equate to a concentration of ammonium, or specific amino acids, within sample section 702 by means of pre-programmed calibration curves. Microchip 773 may then send data and information to display device 774 for user readability. Display device 774 may be wholly integrated into testing device 700, or may be connected to testing device 700 physically or wirelessly. Additionally, an alternate embodiment of testing device 700 may incorporate multiple microchips for further program control, and may be connected wirelessly or physically to an external display device, such as a computer, cell phone, TV, LCD screen, printer, or similar display and communication devices. Testing device 700 may also be in communication with devices at hospitals or laboratories for ease of information transfer to a user's doctor or medical facility.

FIG. 12 shows the chemical composition of Nafion. Other similar cation exchange membranes or perfluorinated ionomer membranes may also be used interchangeably.

Any and all journal articles, patent applications, issued patents, or other cited references disclosed herein are incorporated by reference in their respective entireties.

PCT Application Serial No. PCT/US2013/065548.

1. J. Zschocke, G. F. Hoffmann, Vademecum Metabolicum (Milupa Metabolics, Friedrichsdorf, Germany, ed. 3rd, 2011).
2. B. C. Lanpher, A. L. Gropman, K. A. Chapman, U. Lichter-Konecki, M. L. Summar, Urea Cycle Disorders Overview (NCBI Bookshelf, 2003).
3. M. L. Summar, S. Koelker, D. Freedenberg, C. Le Mons, J. Haberle, H.-S. Lee, B. Kirmse, The incidence of urea cycle disorders., Mol. Genet. Metab. 110, 179-80 (2013).
4. R. H. Singh, Nutritional management of patients with urea cycle disorders, J. Inherit. Metab. Dis. 30, 880-7 (2007).
5. M. Msall, Neurological Outcome in Children with Inborn Errors of Urea Synthesis.pdf, N. Engl. J. Med. 310, 1500-1505 (1984).
6. A. L. Gropman, M. L. Batshaw, Cognitive outcome in urea cycle disorders, Mol. Genet. Metab. 81 Suppl 1, S58-62 (2004).
7. M. L. Batshaw, S. Brusilow, L. Waber, W. Blom, A. M. Brubakk, B. K. Burton, H. M. Cann, D. Kerr, P. Mamunes, R. Matalon, D. Myerberg, I. A. Schafer, Treatment of Inborn Errors of Urea Synthesis, N. Engl. J. Med. 306, 1387-1392 (1982).
8. F. F. Poordad, Review article: the burden of hepatic encephalopathy, Aliment. Pharmacol. Ther. 25 Suppl 1, 3-9 (2007).
9. R. F. Butterworth, J. F. Giguere, J. Michaud, J. Lavoie, G. P. Layrargues, Ammonia: key factor in the pathogenesis of hepatic encephalopathy, Neurochem Pathol 6, 1-12 (1987).
10. R. F. Butterworth, Pathophysiology of hepatic encephalopathy: a new look at ammonia, Metab. Brain Dis. 17, 221-7 (2002).
11. J. Stahl, Studies of the Blood Ammonia in Liver Disease, Ann. Intern. Med. 58 (1963).
12. I. Eijgelshoven, S. Demirdas, T. A. Smith, J. M. T. van Loon, S. Latour, A. M. Bosch, The time consuming nature of phenylketonuria: A cross-sectional study investigating time burden and costs of phenylketonuria in the Netherlands, Mol. Genet. Metab. 109, 237-242 (2013).
13. P. V. D. Burg, H. W. Mook, A simple and rapid method for the determination of ammonia in blood, Clin. Chim. Acta 8, 162-164 (1962).
14. Y. Murawaki, K. Tanimoto, C. Hirayama, Y. Ikuta, N. Watabe, A simple and rapid microdiffusion method for blood ammonia using a reflectance meter and a reagent plate, and its clinical evaluation for liver diseases, Clin. Chim. Actal 144 (1984).
15. R. J. Barsotti, Measurement of ammonia in blood, J. Pediatr. 138, S11-S20 (2001).
16. J. Buttery, R. Ratnaike, B. Chamberlain, The measurement of erythro-cyte ammonia using the Hyland ammonia kit, J Clin Chem Clin Biochem 20 (1982).
17. S. Dienst, An ion exchange method for plasma ammonia concentration, J. Lab. Clin. Med. 58 (1961).
18. J. Huizenga, C. Gips, Determination of blood ammonia using the Ammonia Checker, Ann Clin Biochem 20 (1983).

19. H. van Anken, M. Schiphorst, A kinetic determination of ammonia in plasma, Clin Chim Acta 56 (1974).
20. L. Rover Junior, J. C. Fernandes, G. de Oliveira Neto, L. T. Kubota, E. Katekawa, S. H. Serrano, Study of NADH stability using ultraviolet-visible spectrophotometric analysis and factorial design, Anal. Biochem. 260, 50-5 (1998).
21. M. Berthelot, B, Repert. Chim. Appl., 254 (1859).
22. E. D. Rhine, G. K. Sims, R. L. Mulvaney, E. J. Pratt, Improving the Berthelot Reaction for Determining Ammonium in Soil Extracts and Water, Soil Sci. Soc. Am. J. 62 (1998).
23. T. T. Ngo, A. P. H. Phan, C. F. Yam, H. M. Lenhoff, Interference in Determination of Ammonia with the Hypochlorite-Alkali Phenol Method of Berthelot, 46-49 (1981).

EXAMPLES

Example 1

The presented work demonstrates how the systematic investigation of previously known technologies yielded the fabrication of an effective blood ammonia sensor. The indophenol reaction, in tandem with a polyelectrolyte membrane, was explored as a means to quantify ammonia concentrations in whole blood.

The ammonia-indophenol standard curve was produced using a range of ammonium chloride concentrations in 1× phosphate buffered saline (PBS) of 0 to 750 µM. The following concentrations were utilized in the indophenol reaction: 59 mM 2-phenylphenol in ethanol, 7 µM sodium nitroprusside in water, 500 mM sodium hydroxide in water, and 0.2-0.25% aqueous hypochlorite. These concentrations were mixed in a 1:1:1:0.5 ratio with an equal volume of the ammonium solution of interest and allowed to react at room temperature for 10 minutes. The absorbance of the resulting solution was measured at a wavelength of 635 nm.

Example 2

The reagents utilized in the indophenol reaction were investigated for long term stability. Aqueous solutions of hypochlorite, sodium nitroprusside, sodium hydroxide and a solution of 2-phenylphenol in ethanol were stored in separate 50 mL falcon tubes, with limited exposure to light. At intervals of 3, 5, 7, 15, 21, 28, 35, 50, 75 and 100 days the hypochlorite, sodium nitroprusside, sodium hydroxide and 2-phenylphenol were utilized to develop a standard curve using ammonia concentrations ranging from 0-750 µM. Significant deviations from the original standard curve indicated the degradation of the stored reagents. It should be noted that fresh ammonia samples were utilized at each test interval.
Response to Amino Acids
Primary amines can also undergo the indophenol reaction. Total amino acid concentrations in blood can be as high as 2.5 mM, therefore the selectivity of 2-phenylphenol was determined in the indophenol reaction. 1 mM solutions of each of the 21 amino acids was prepared in 1×PBS. The same protocol utilized with the indophenol reagents for the ammonia standard curve was utilized with each amino acid solution. 10 minutes after the indophenol reagents and amino acid solution was mixed, its absorbance at 635 nm was measured using a plate reader. The response was directly compared to the response seen from a 1 mM solution of ammonium chloride and expressed as a percentage of the ammonium response.
Sensor Design
While the following tests and experiments can be used with any of the cartridges disclosed herein, the specific data shown below came from the blister-pack and dried reagent cartridge as disclosed in FIG. 5A.
Hypochlorite Concentrations Effect on Indophenol Response to Blood Ammonia
To reduce interference from reducing species in blood, higher concentrations of hypochlorite than conventionally utilized were employed in the indophenol reaction with ammonia extracted from whole sheep's blood. 1, 2, 3, 5, and 10× concentrations of hypochlorite were utilized and the resulting absorbance at 635 nm was recorded.
Proper Reagent Concentrations
In order to correctly state the concentrations, it is easier to provide them in terms of final concentration after mixed together and with ammonium. Ideally, any starting concentration should work as long as the final concentration is the same as what is listed below. For convenience, I have also listed the concentrations of reagents used to produce these final concentrations. Table 5 below assumes an ammonia solution of a volume of 20 microliters was added. A general 20% swing of concentrations would be valid for each reagent other than sodium nitroprusside, but the listed values are optimal.

TABLE 5

| Reagent | Reagent Concentration | Volume | Final Mixed Concentration |
| --- | --- | --- | --- |
| Sodium Hypochlorite | 0.175% | 7 microliters | 0.025% |
| Sodium Nitroprusside | 400-500 micrograms/mL | 7 microliters | 58-72.9 micrograms/mL |
| 2-phenylphenol | 5 mg/mL | 7 microliters | 0.73 mg/mL |
| Sodium Hydroxide | 10 mg/mL | 7 microliters | 1.45 mg/mL |

Figure 14:
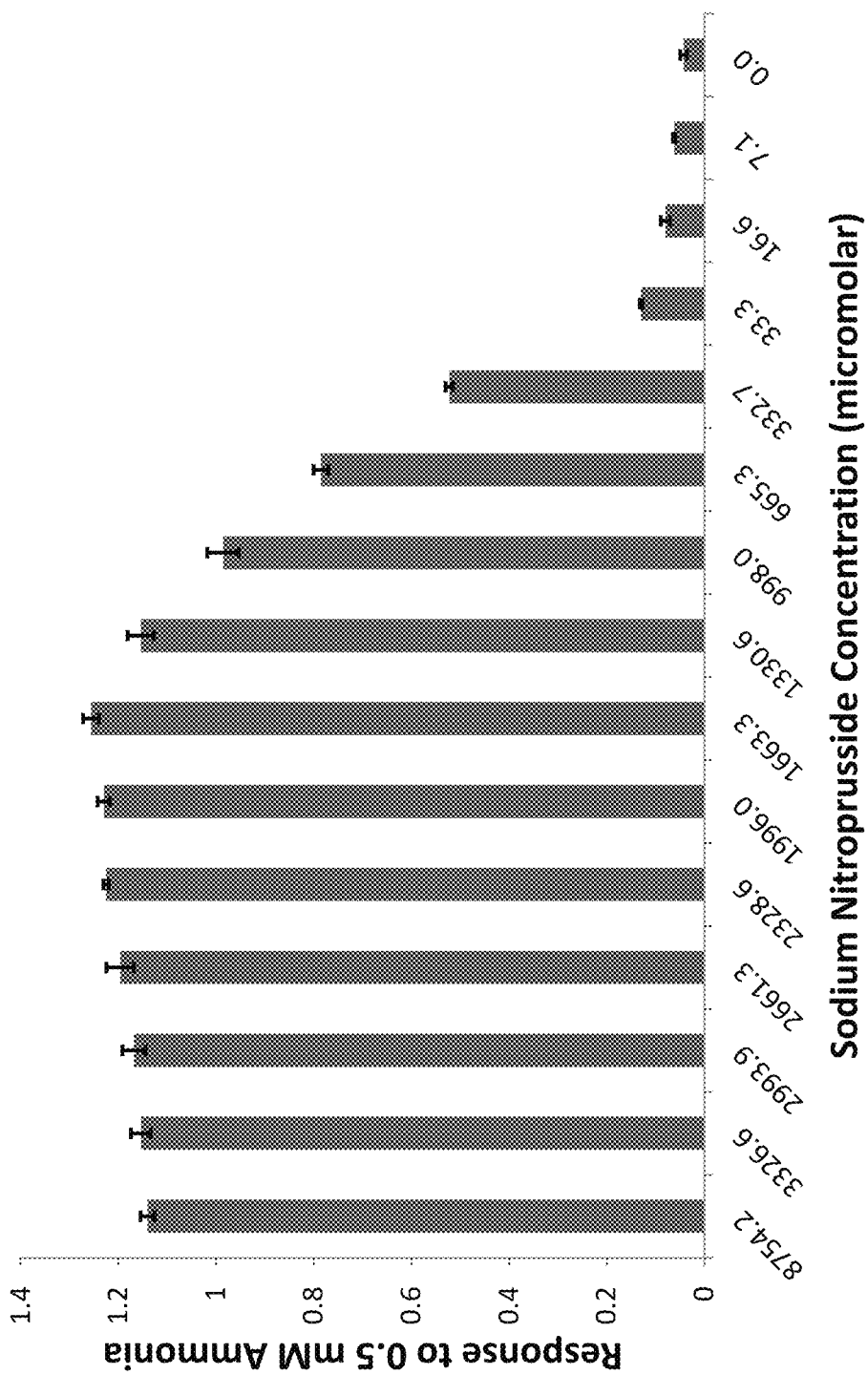
FIG. 14 depicts the detection of 500 micromolar ammonia solutions using various concentrations of sodium nitroprusside and the indophenol reaction. Appropriate amounts of the other reagents were used in this optimization. A concentration range of 1330-1996 micromolar sodium nitroprusside is optimal for detection of ammonia.
Figure 15:
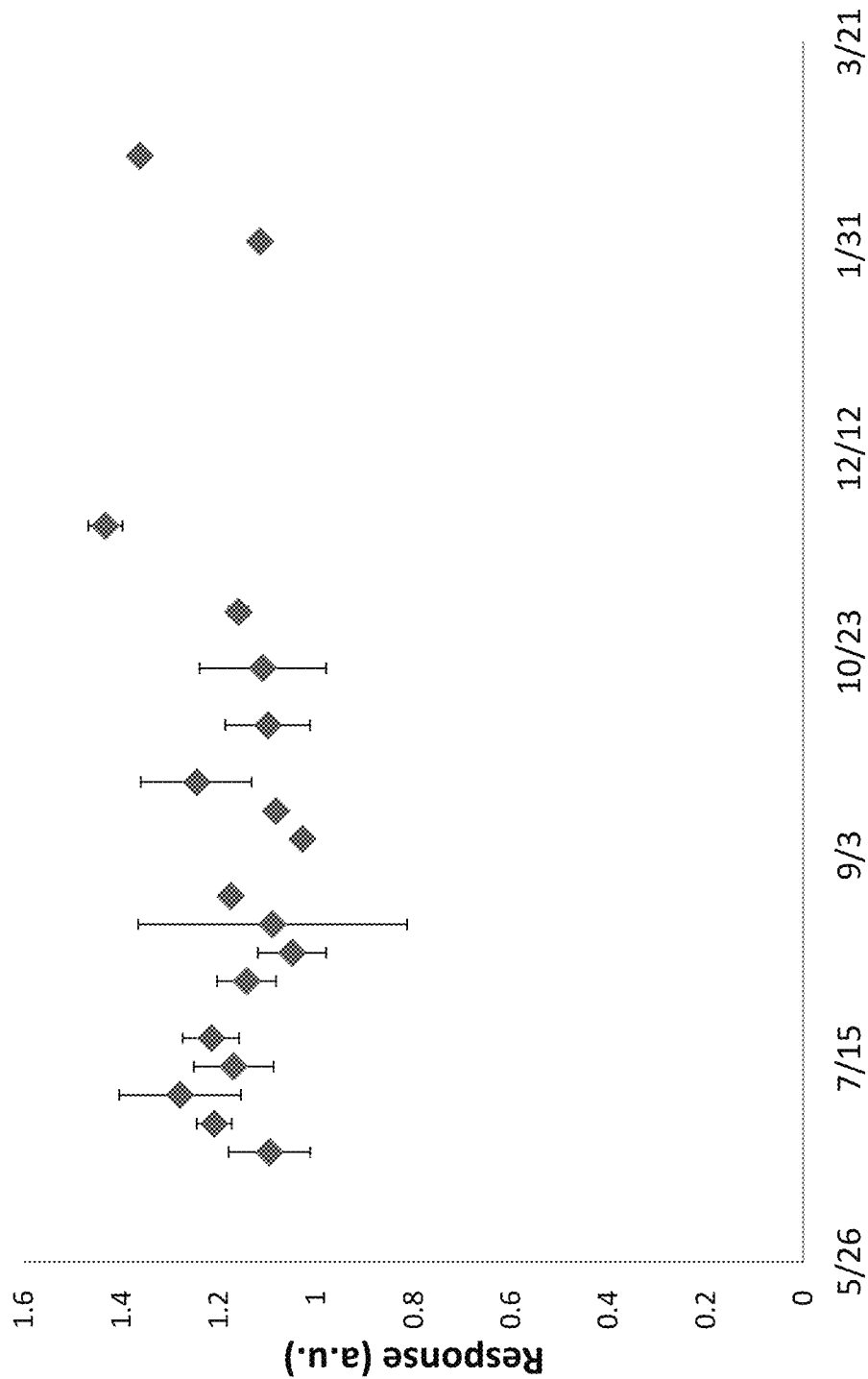
FIG. 15 depicts the response of solutions used for the indophenol reaction to 500 micromolar ammonium chloride over the course of 245 days at room temperature. The response to the ammonia chloride was stable for the entire experiment.

Optimized Sodium Nitroprusside
As shown in FIG. 14, concentrations of 7-8754 micromolar sodium nitroprusside solution was utilized to detect 500 micromolar ammonia solutions using the indophenol reaction. Appropriate amounts of the other reagents were used in this optimization. It is evident from the above figure that a concentration of 1330-1996 micromolar were optimal for detection of ammonia.
Stability
As shown in FIG. 15, One major advantage of using the indophenol reaction for determining ammonia concentrations is that it does not require any biological components such as enzymes, which are high in cost and prone to stability issues. The shelf life of the solutions used for the indophenol reaction was evaluated over the course of 245 days. The response to the range of ammonia chloride concentrations was stable for the entire course of the current study. As seen in FIG. 15, the response to 500 µM ammonium chloride did not change significantly over the course of 245 days. It should be noted that this was not performed using the laboratory prototype test cassette, which significantly lowers the day-to-day variability of the measurements as seen in the following sections.

Calibration Curve and Sensitivity

Figure 16:
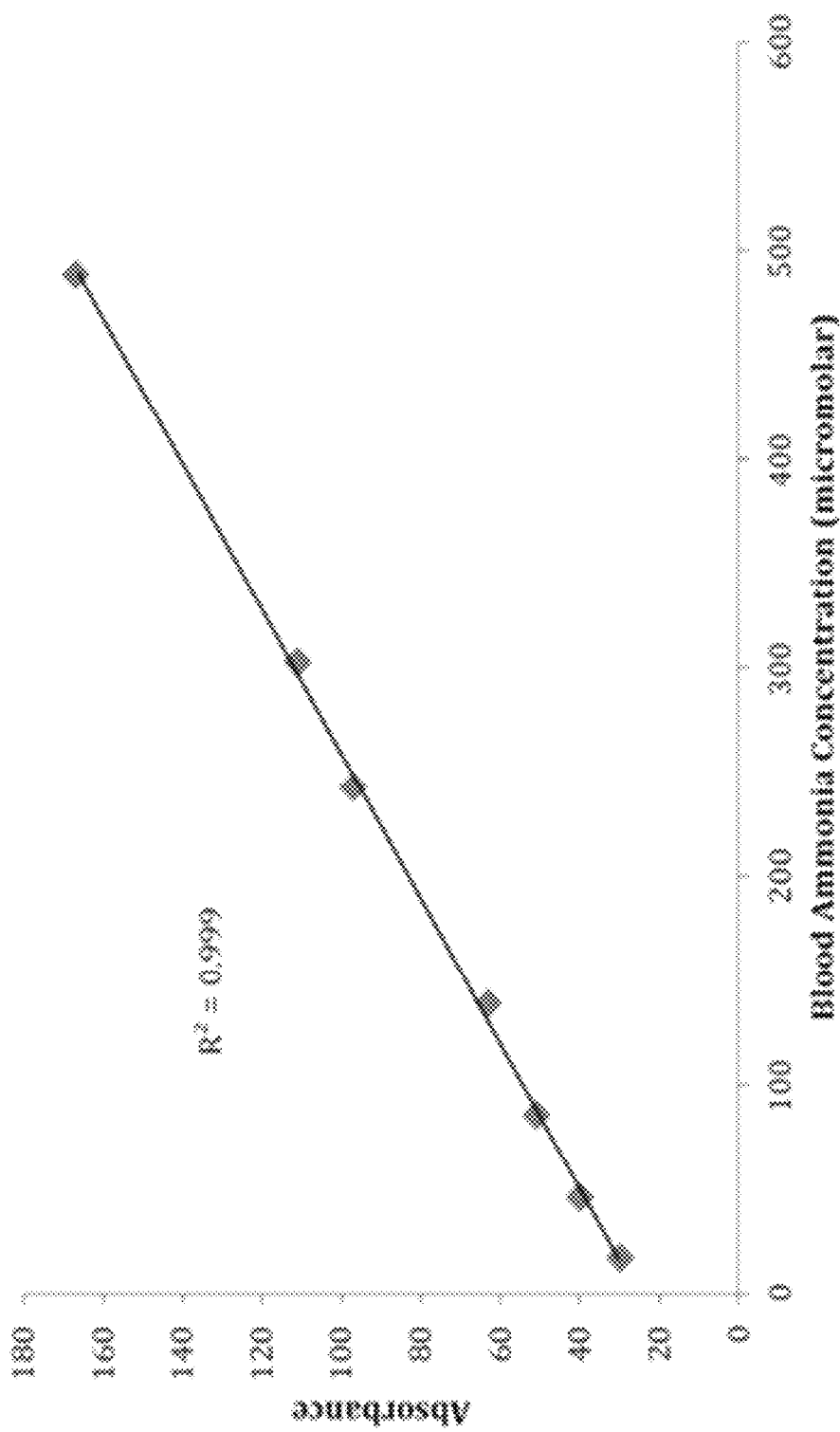
FIG. 16 depicts a calibration curve for detecting blood ammonia concentrations using a cartridge of the disclosure. Concentrations of blood ammonia were generated by either spiking whole blood samples or allowing them to hydrolyze at room temperature. The calibration curve has an R2 of 0.999 and a measured sensitivity of 0.288 a.u./µM of ammonia. The calibration curve covers concentrations of blood ammonia ranging from 20 to 500 µM of ammonia and thus cover the entire physiologically normal to highly elevated range. This calibration curve was utilized to determine the limit of detection and limit of quantification, which were 8 µM and 27 µM respectively.

A calibration curve was generated using the laboratory prototype test cassettes as seen in FIG. 16. Concentrations of blood ammonia were generated by either spiking whole blood samples or allowing them hydrolyze at room temperature. Seven measurement points produced the curve, which fall within the FDA guideline for pre-validation of a bioanalytical method. The calibration curve has an excellent $R^2$ of 0.998. Additionally the measured sensitivity was 0.288 a.u./μM of ammonia. This sensitivity will allow for high-resolution measurements. It should be noted that the calibration curve covers concentrations of blood ammonia ranging from 20-500 μM and thus covers the entire physiologically normal to highly elevated range. This calibration curve was utilized to determine the limit of detection and limit of quantification, which were 8 μM and 27 μM respectively.

The investigated system for evaluating blood ammonia levels demonstrated a high degree of correlation between blood ammonia and sensor response. In the range of 2S-1SO)lM, the most clinically critical concentrations, the relative standard deviation was just 12.23%. The method could discern levels of SO and 100)lM with a p=O.OOO 1, indicating the system is extremely reliable in differentiating these concentrations.

The sensor has a 30 minute response time, and the interference from other small molecules and proteins was greatly reduced. The components used are stable at room temperature for up SO days and inexpensive. This presented method could lead the way for PoC devices for whole blood ammonia detection. Ultimately, such a device would assist in the rapid diagnosis of urea cycle disorders, which are not included in newborn screening programs. Due to their exclusion from newborn screening, UCDs are often misdiagnosed and treated after severe hyperammonemic episodes. Additionally, measured blood ammonia levels can often result in false positives due to the difficulty in sample processing, which can involve several preparative steps and logistical hurdles. The future development of a point-of-care device would provide an attending physician with the option for rapid diagnosis, especially in the intensive care unit setting. This is particularly imperative as high ammonia levels can be indicative of many disorders outside of UCDs, such as organic acidemias, fatty acid oxidation disorders and other rare inborn errors of metabolism. At home testing is another option for such a point-of-care device in the management of UCDs. Dietary adjustments could be made more readily, however, due to parental expectations and use, this option should be examined carefully and approached strategically to ensure the patient's best interest is taken into account.

Variability

The Clinical Laboratory Standards Institute guideline for measuring variability was utilized to determine the test cassette variability. Low, medium and high concentrations of ammonia were measured twice a day for 5 days, as shown on Table 6 below. The variability displayed in the above table is the standard deviation of each measurement divided by the average measurement. For each concentration, the variability was less than 15%, which falls within the FDA guidelines for required variability limits for a bioanalytical method. This translates to 2.5 μM resolution at low concentrations, ~10 μM resolution at medium concentrations and 25 μM resolution at high concentrations.

TABLE 6

| | Ammonia Concentration (μM) | | |
|---|---|---|---|
| | 25 | 125 | 500 |
| Variability | 10% | 11.5% | 5% |

Correlation with Clinical Test

Figure 17:
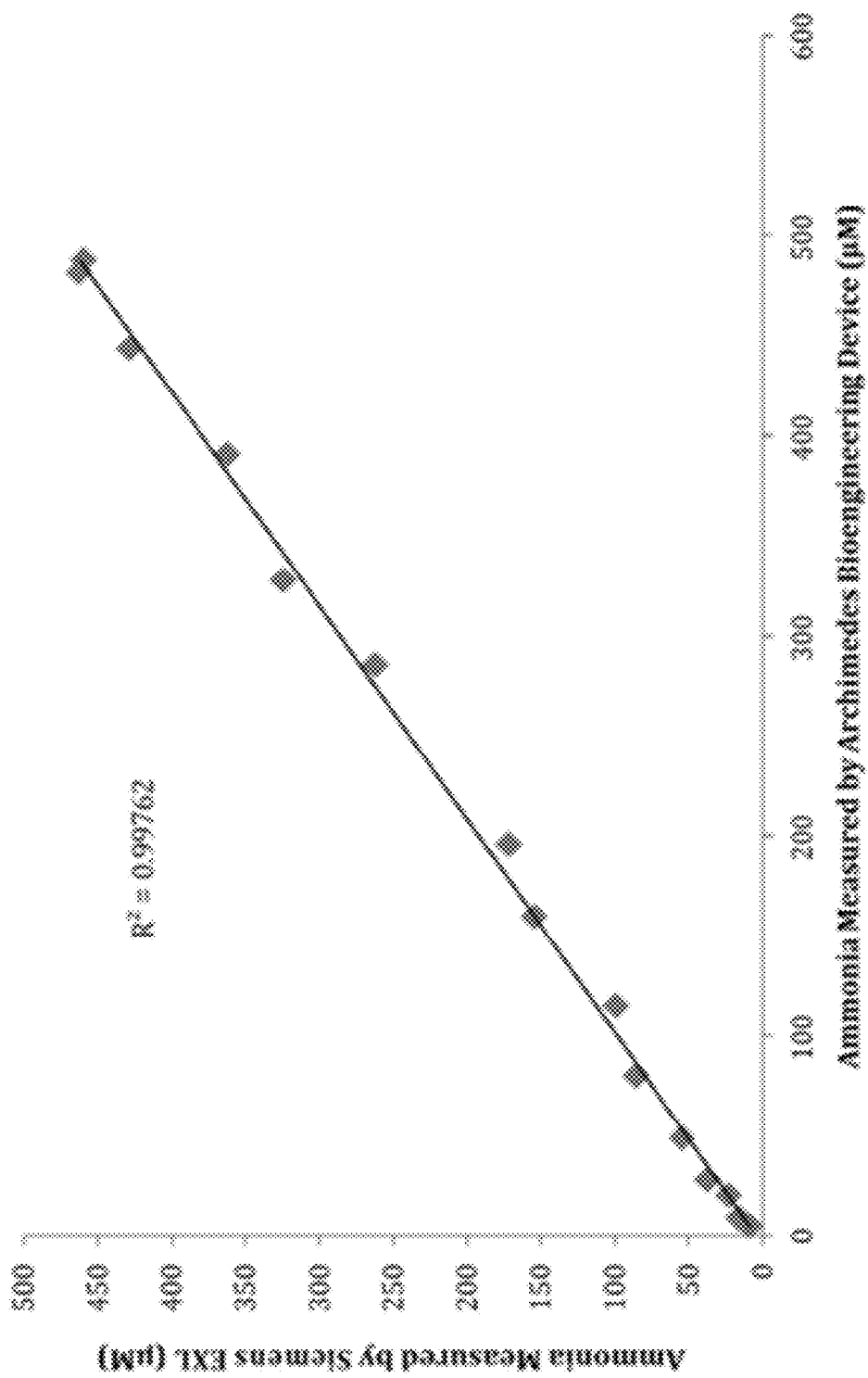
FIG. 17 depicts a calibration curve for comparing the detection of blood ammonia concentrations using the Siemens EXL, a clinical chemical analyzer, versus a cartridge of the disclosure.

The cartridge's ability to accurately measure blood ammonia was directly correlated with measurements taken by the Siemens EXL, a clinical chemical analyzer currently used in hospital laboratories around the nation. Measurements taken were converted into blood ammonia values by use of the calibration curve seen in FIG. 17. Blood ammonia samples were split into 40 μL and 200 μL aliquots. The 40 μL aliquot was utilized for the sample cartridge and the 200 μL aliquot for the Siemens EXL. The aliquot for the Archimedes meter was used immediately within the device, which produced a measurement in 25 minutes. The aliquot for the Siemens EXL was centrifuged in a 4° C. centrifuge for 10 minutes to yield the plasma fraction. This plasma fraction was then inserted into the Siemens EXL and a result was obtained 10 minutes later. The two measured values were then plotted against each other as seen in FIG. 17 blood ammonia measurements were utilized to generate the correlational curve. As seen, the cartridge blood ammonia meter produced results that correlated tightly with the Siemens EXL with an r2 of 0.997.

Calibration Curve with Dried Reagents

Figure 18:
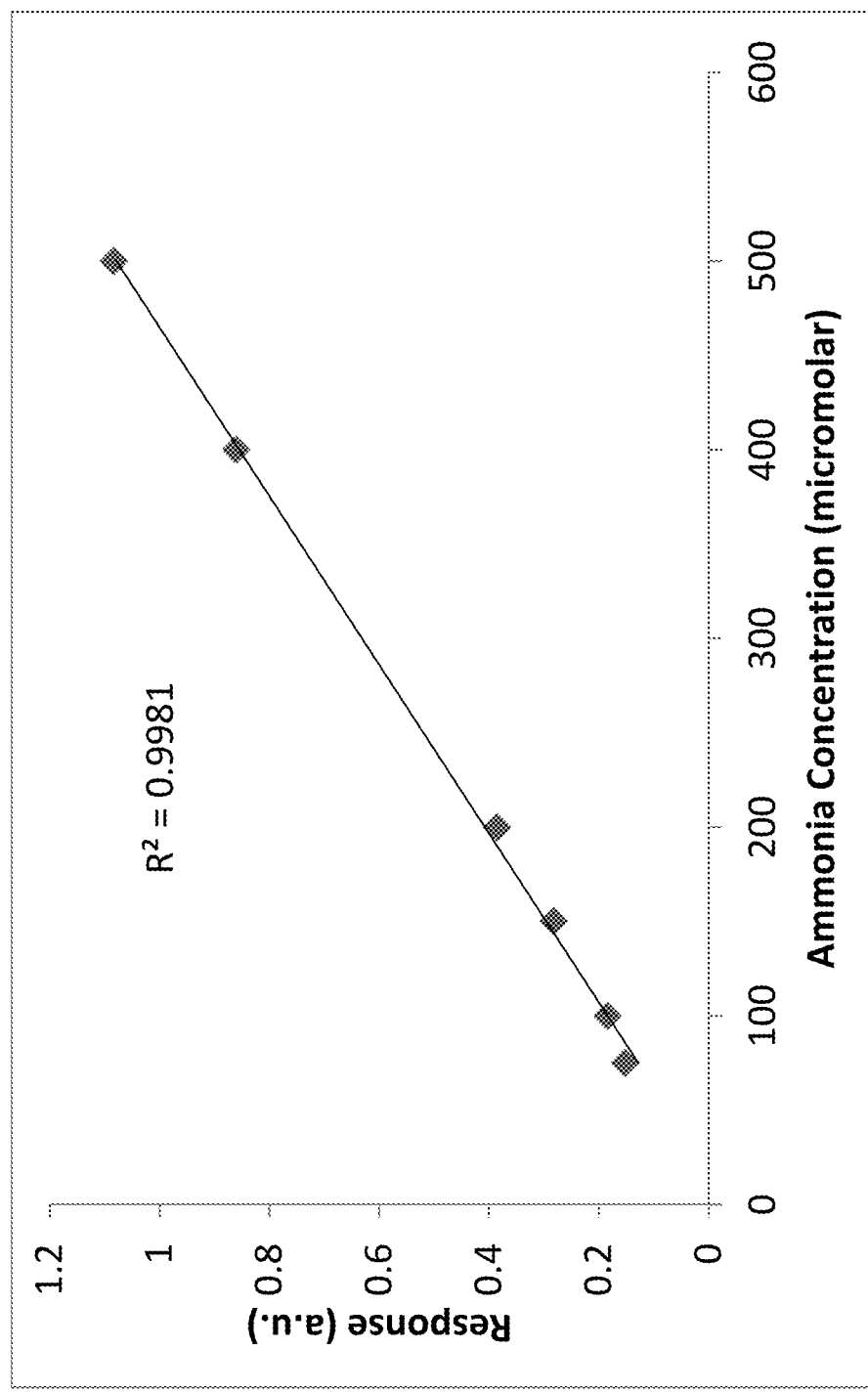
FIG. 18 depicts a calibration curve produced through the use of dried 2-phenylphenol and sodium nitroprusside reconstituted using sodium hypochlorite, sodium hydroxide and ammonium solution. The produced curve was linear from concentrations of 0-500 micromolar ammonium.

To demonstrate the viability of drying reagents used in the indophenol reaction, two components of reaction, namely the sodium nitroprusside and the 2-phenylphenol were drop casted and air-dried prior to use. The two reagents would be reconstituted using the other two reagents used in the colorimetric indophenol reaction, specifically sodium hypochlorite and sodium hydroxide. Subsequently to reconstitution the ammonium sample would be added and the developed color measured. As seen in FIG. 18, this approach produced a linear curve for concentration of ammonium ranging from 0-500 micromolar. It should be noted that the resulting 'reacting' solution contained the appropriate concentrations of each reagent.

Example 3: Measuring Ammonia in Whole Blood with a Fluidic Device

Materials 2-phenylphenol, sodium nitroprusside, sodium hydroxide, sodium hypochlorite, sodium acetate, and ammonium chloride were purchased from Sigma-Aldrich. Nafion 111 was purchased from Ion-Power.

Methods

Sensor Design and Construction

A bisected well containing whole human blood in one section and a solution of sodium acetate in the other provide a means for cation exchange of the whole blood to occur, yielding a high recovery of the ammonium. Modular well-halves were 3D printed from acrylonitrilebutadiene-styrene thermoplastic. The pieces snap together with the 1 cm2 Nafion 111 membrane in the middle, forming a Nafion bisected well. This design was chosen to provide a uniform platform for all future experiments involving this sensing method. A silicone gasket, at a 1/64 inch thickness, was glued to the inner face of each well-half to ensure a water tight seal.

Extracting Ammonia

Sodium acetate was utilized to extract ammonia through ion-exchange. Concentrations of 0.1, 0.5 and 1M sodium acetate were prepared. Using fresh Milli-Q water (18.5 MΩ), to ensure no ammonia contaminants were present. Bisected wells were prepared, with 100 μl of 500 μM of ammonium chloride in one section and 45 μl of the sodium acetate solution in the other. Ion-exchange took place for 20 minutes before 35 μl of the now ammonia-enriched sodium acetate was tested.

Reducing Interference from Blood-Borne Small Molecules

Reducing agents in blood such as uric acid can negatively interfere with the indophenol reaction. Increasing concentrations of the hypochlorite were utilized in a modified version of the indophenol reaction to eliminate this negative interference. 500 μM solutions of ammonium chloride were prepared in PBS and in whole human blood. The ammonia was extracted from these samples using previously described ion-exchange protocol. The concentration of hypochlorite was varied between 0.2S-2.S % to examine its effectiveness in reducing interference.

Sensor Response to Ammonia in Whole Blood

The 3D printed wells were constructed with 1 cm2 pieces of Nafion membrane. Whole human blood was spiked using ammonia chloride to generate concentrations of ammonia of 25, 50, 75, 100, 150, 200, 250, 300, 400 and 500 μM. In one section of the well, 100 μl of the ammonia containing blood sample was added. In the opposing section 1 M sodium acetate was added. Ion-exchange of ammonia was allowed to occur for 20 minutes. To a 384 well plate, 3S)lL of ammonia extracted sample, 10)lL of 2-phenylphenol, 10)lL of NaOH, 5 μl of 0.75% hypochlorite and an appropriate amount of sodium nitroprusside were added. The absorbance of the resulting indophenol reaction was measured at 635 nm after 10 minutes using a microplate reader.

Preparation of Sample
  Prepare stock solutions of 59 mM 2-phenylphenol in ethanol, 7 μM sodium nitroprusside in water, 500 mM sodium hydroxide in water and 0.75% sodium hypochlorite in water.
  Prepare a stock solution of 1M sodium acetate in water.
  Molds are produced from a 3D printer for the 2 individual pieces of the device.
  Fill each mold with the PDMS elastomer and heat at 60° C. for one hour.
  Remove each side of the device from the mold with a spatula.
  Remove the 25 μm thick Nafion 111 from plastic backing and cut it into a 1.5×1.5 cm square.
  Glue the square of Nafion over the well in the channel 6 using PDMS.
  Glue the top piece of the device to the bottom piece using PDMS, ensuring channel 6 lines up with channel 5.
  Heat the device to 60° C. for one hour.

Ammonia Exchange
  Insert a needle through the bottom of the device into well 6, and fill with 40 μl of blood.
  Fill channels 1-4 with 5 μl of 2-phenylphenol, sodium nitroprusside, sodium hydroxide and sodium hypochlorite respectively.
  Fill channel 5 with 20 μl of sodium acetate solution.
  Wait 20 minutes for ion exchange to occur.

Collection of Data
  Apply a flow rate of 1 mm/sec to channels 1 through 5 for 24 seconds.
  Wait ten minutes for the indophenol reaction to proceed.
  Insert the device into the custom photo-spectrometer to acquire absorbance data.
  Compare the measured absorbance to a standard curve to determine unknown ammonia concentration.

Figures 20A, 20B:
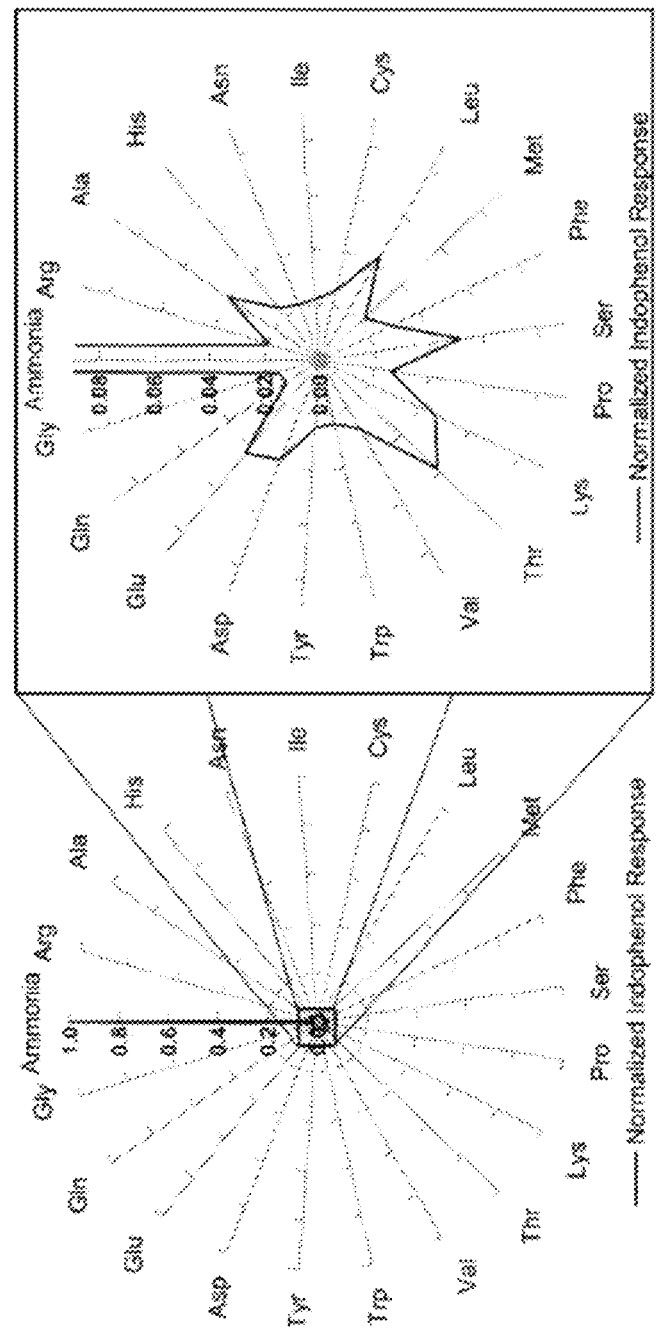
FIGS. 20A and 20B depict a radar graph showing the detection of amino acids.

FIG. 20 depicts the results of amino acid detection using the indophenoal reaction. 1 mM concentrations of each of the 21 amino were tested using the indophenol reaction. The absorbance measured at 635 nm for each amino acid after the indophenol reaction was calculated as percentage of the response from indophenol reaction with 1 mM ammonia chloride. The radar graph displays the percent response as compared to 1 mM ammonia chloride. The highest response was threonine, which produced an absorbance value at just 5% of ammonia's response.

Figures 21A, 21B:
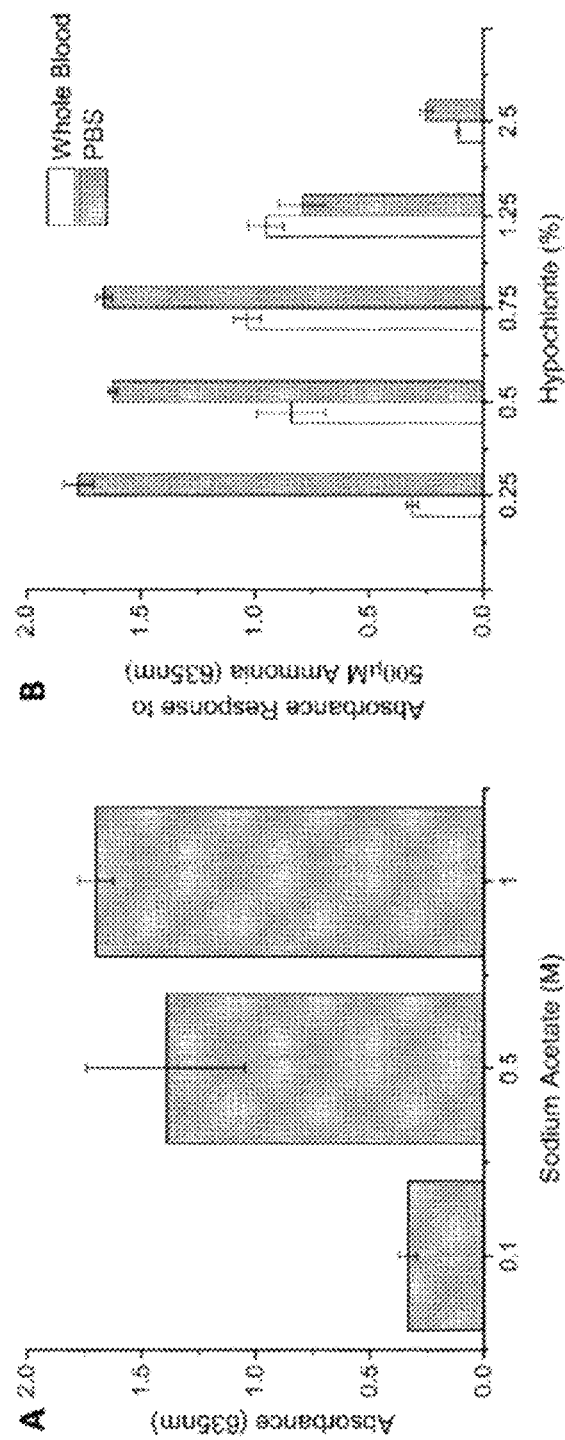
FIGS. 21A and 21B show the review of concentrations of reagents used in the experiments.

FIGS. 21A and 21B show the review of concentrations of reagents used in the experiments. The ion-exchange of ammonia through the use of a Nafion membrane is the mechanism of recovery of the analyte. Sodium salt solutions of different concentrations were tested for their effectiveness in exchanging with the ammonia from a PBS solution. It was expected that higher concentrations of sodium salts would yield larger recoveries of ammonia. Bisected wells were prepared with Nafion membranes. A 500 μM solution of ammonium chloride in PBS was placed on the 'analyte' side of the bisected well and solutions of sodium acetate in the opposing bisection. As seen in FIG. 21A, a concentration of 1 M gave the largest recovery in 20 minutes. This recovery was about 40% from whole blood and about 70% from a 1×PBS solution. The indophenol reaction is also sensitive to the presence of blood-borne reducing agents such as uric and ascorbic acid. These molecules, amongst others, can react with intermediates of the indophenol reaction as well as the hypochlorite. This effect was evident when initially testing serial dilutions of ammonia in whole blood. The response plateaued at higher concentrations of ammonia due to side reactions with indophenol reagents. To circumvent this issue, larger concentrations of hypochlorite were introduced to the reaction when detecting 500 μM ammonia in both whole blood and PBS. As seen in FIG. 21B, with a 0.25% hypochlorite solution, the response to ammonia in whole blood was less than 20% of the response to ammonia in PBS. Increasing the hypochlorite concentration resulted in larger responses to whole blood, with a 50% response as compared to PBS, at an optimum concentration of 0.75%. At larger concentrations the response to both whole blood and PBS began to degrade.

Example 4: Fingerstick Ammonia Measurements

Figure 19:
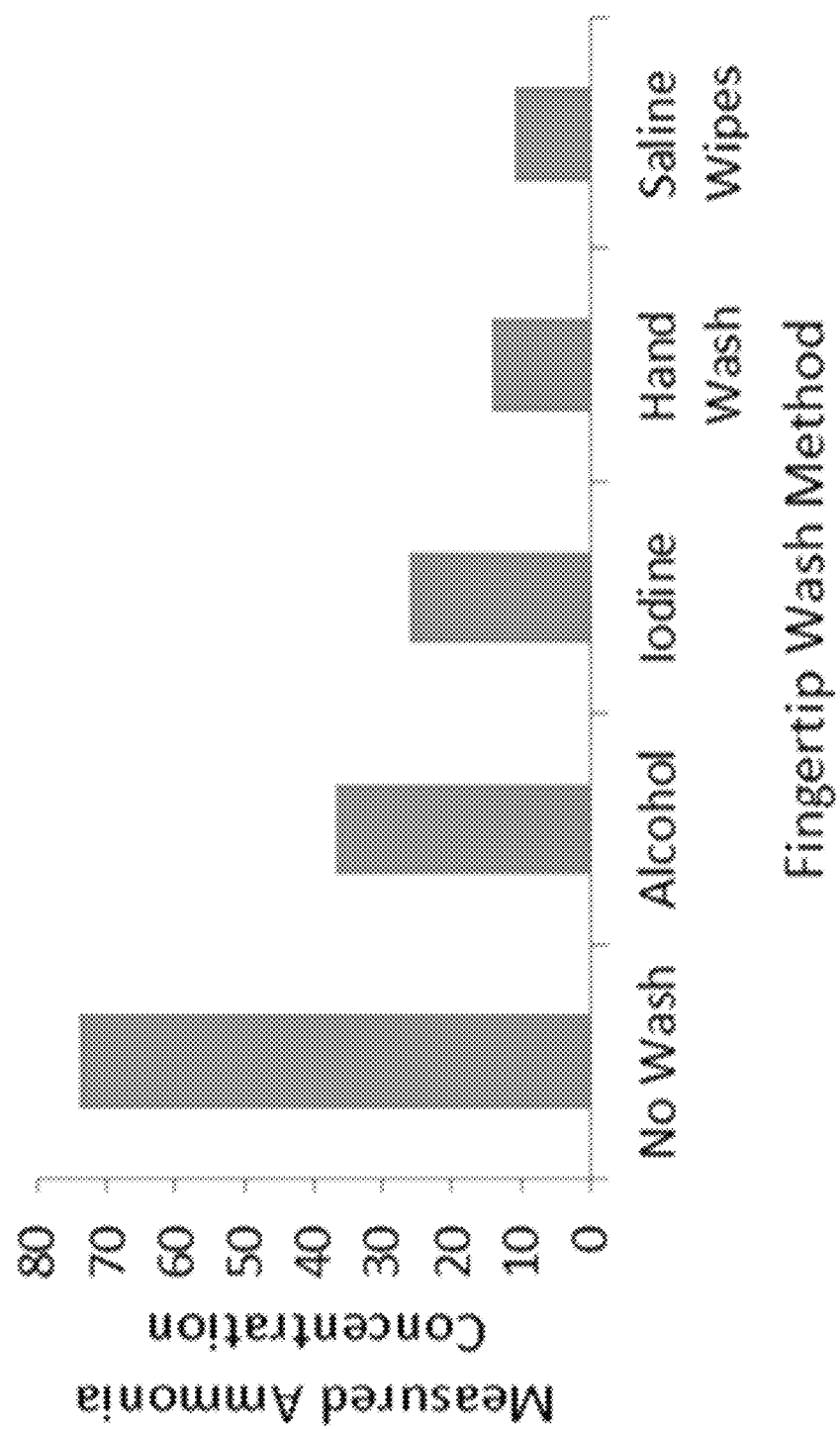
FIG. 19 depicts the measured ammonia concentration from a fingerstick blood draw after various fingertip washing methods.

Fingerstick ammonia measurements are known to produce false positive values. The prevailing theory assumed that hemolysis from shearing forces from the fingerstick contaminated the blood sample with ammonia from tissue. To demonstrate that hemolysis is not the cause for contamination venous draws and fingerstick ammonia were acquired within the same hour. As seen in Table 7 below, fingerstick ammonia values, while varied, did not correlate with the degree of hemolysis observed. This preliminary data, in conjunction with previously reported data, demonstrates that hemolysis is not a predictor of a false positive read in ammonia concentration. Another source of false elevations from fingerstick ammonia likely comes from dried sweat on the fingertip. Sweat ammonia values can be as high as 1000-3000 micromolar, which can easily cause a false positive. This theory was tested by exposing saline solution to a fingertip and then measuring the corresponding ammonia concentration in the saline solution, the results of which can be seen in FIG. 19. For an "unwashed" finger, the measured ammonia concentration was 74 micromolar. Alcohol and iodine swabs, which are the most commonly used swabs for fingertip pre-treatment before a fingerstick, lowered the measured concentration to 37 and 26 micromolar respectively. Handwashing and saline wipes lowered the measured ammonia concentration to 14 and 11 micromolar respectively. This demonstrates the poor cleaning of the fingertip can significantly contribute to false elevations in fingerstick blood ammonia measurements. It also demonstrates that certainly cleansing swabs, primarily those containing saline solution, are more effective than traditional swabs from removing ammonia from the fingertip.

TABLE 7

| Measured NH4+ | Blood Draw Type | Hemolysis Appearance |
|---|---|---|
| 9 | Venous | None |
| 6 | Venous | None |
| 51 | Fingerstick | None |
| 34 | Fingerstick | Pink |
| 25 | Fingerstick | Light Pink |
| 42 | Fingerstick | Light Pink |

The foregoing description and accompanying figures illustrate the principles, preferred embodiments and modes of operation of the disclosure. However, the disclosure should not be construed as being limited to the particular embodiments or applications discussed above. Additional variations, modifications, and applications of the embodiments discussed above will be appreciated by those skilled in the art. Additional variations and modifications may include, but are not limited to, the detection of a variety of different amino acids, such as phenylalnine, histidine, tyrosine, glutamate, threonine, serine, leucine, isoleucine, aspartate, valine, glycine, alanine, tryptophan, proline, lysine, arginine, or others. Detection of these amino acids may involve placing dehydrogenase enzymes or other ammonia lyase enzymes in the sample section of the well, along with the blood, serum, or plasma. Possible applications for the detection of the presence of ammonia or ammonium ion is to diagnose phenylketonuria or other aminoacidopathies.

Therefore, the above-described embodiments should be regarded as illustrative rather than restrictive. Accordingly, it should be appreciated that variations to those embodiments can be made by those skilled in the art without departing from the scope of the disclosure as defined by the following claims.

The invention claimed is:

1. A biosensor comprising:
at least a first and second vessel;
a fluid exchange opening positioned between the first and the second vessel;
a membrane positioned across or over the fluid exchange opening; and
a catalyst in solid phase within the second vessel or within a first conduit in fluid communication with the second vessel, wherein the catalyst is nitroprusside or salt thereof with a mass of from about 5.5 micrograms to about 7.8 micrograms;
wherein the membrane comprises an ionomer.

2. The biosensor of claim 1 further comprising a compound comprising a phenyl group in solid phase within the second vessel or within a conduit in fluid communication with the second vessel.

3. The biosensor of claim 2, wherein the compound comprising a phenyl group has a mass of from about 75 micrograms to about 85 micrograms.

4. The biosensor of claim 1, wherein at least the first conduit is in fluid communication with at least the first vessel, the first conduit configured to receive a fluid from a point external to the biosensor.

5. The biosensor of claim 1, wherein the first vessel or the second vessel: (i) comprises one or a combination of a hypohalite, an alkali buffer, and at least one: phenolic reagent or indophenol related compound; or (ii) are in fluid communication with a second conduit connected to a storage vessel that comprises a fluid comprising individually or in combination: a hypohalite, an alkali buffer, and at least one: phenolic reagent or indophenol related compound.

6. The biosensor of claim 5, wherein the first vessel or the second vessel are in fluid communication with at least one reagent conduit configured to receive a fluid from a reagent storage vessel at a point distal from the first or second vessel.

7. The biosensor of claim 6, wherein the first vessel or the second vessel is in fluid communication with: (i) a first reagent conduit configured to receive a fluid from a first reagent storage vessel comprising a compound comprising a phenyl group in liquid phase; (ii) a second reagent conduit configured to receive a fluid from a second reagent storage vessel comprising a hypohalite in liquid phase; and (iii) a third reagent conduit configured to receive a fluid from a third reagent storage vessel comprising an alkali buffer in liquid phase.

8. The biosensor of claim 6, wherein at least one reagent storage vessel is a blister pack comprising a seal covering the blister pack on a portion of that blister pack adjacent to at least one reagent conduit, wherein the seal is configured for mechanical rupture, such that, upon rupture, a fluid circuit is formed between the first vessel or the second vessel and the reagent storage vessel and fluid contents from the blister pack are capable of fluid flow to the first vessel or the second vessel.

9. The biosensor of claim 1, wherein either the first or the second vessels individually comprise a hypohalite, an alkali buffer, and the catalyst; wherein the first and second vessel are in fluid communication with a detection vessel by at least one reaction conduit, wherein the reaction conduit comprises a first portion positioned proximate to the second vessel, said first portion comprising the catalyst in solid phase, and wherein said first portion comprises the compound comprising a phenyl group in solid phase.

10. The biosensor of claim 9, wherein the alkali buffer comprises from about 0.1 M to about 5 M sodium acetate or sodium chloride.

11. The biosensor of claim 1, wherein the biosensor is free of one or more of the following: (i) uricase or a functional fragment thereof; (ii) a hydrogel comprising dextran or a derivative thereof; (iii) a bacterial cell; (iv) an electronic dipole configured for electrophoresis; (v) 3, 4-DHB, (vi) a vaporizer, gas chromatograph, or a heating element configured for converting liquid ammonia into a gaseous state; and (vii) a membrane comprising cellulose or a derivative thereof.

12. The biosensor of claim 1, wherein the first vessel has a volume from about 5 µl to about 100 µl, and, optionally, the second vessel has a volume from about 5 µl to about 100 µl.

13. The biosensor of claim 1 further comprising: (i) a circuit comprising the at least one wire, and a digital display operably connected to a processor configured to receive digital information from the spectrophotometer and to send digital information to the digital display; and (ii) a test strip comprising the first conduit configured for receiving a volume of bodily fluid.

14. The biosensor of claim 1, further comprising at least one indophenol reagent or indophenol related compound selected from: phenol, 2-phenylphenol, or napthol; wherein the alkali buffer is about 1.0 M sodium chloride, calcium chloride, zinc chloride, sodium acetate, calcium acetate, or zinc acetate; and wherein the membrane comprises Nafion.

15. The biosensor of claim 1, capable of being stored at about room temperature or frozen for no less than 50, 100, 150, 200, or 245 days.

16. The biosensor of claim 1, wherein the membrane comprises Nafion which has not been pre-treated with an acid solution and/or a hydrogen peroxide solution.

17. A system comprising: (i) the biosensor of claim 1 in operable connection to at least one computer storage memory; (ii) a computer processor in operable connection with the at least one computer storage memory; wherein the computer processor is in operable connection with at least one light emitting diode (LED), amplification circuit, battery, and stepper motor.

18. A method of diagnosing a metabolic disease in a subject comprising:
  (a) contacting a sample of bodily fluid to the biosensor of claim 1;
  (b) quantifying one or more concentration values of ammonia in the sample;
  (c) comparing the one or more concentration values of ammonia in the sample to a threshold value of ammonia concentration identified as being in a healthy range; and
  (d) identifying the subject as having a metabolic disease if the one or more concentration values of ammonia in the sample exceed or fall below the threshold value.

19. The method of claim 18, wherein the metabolic disease is hyperammonemia.

20. A method of treating a metabolic disease comprising:
  (a) contacting a sample of bodily fluid to the biosensor of claim 1;
  (b) quantifying one or more concentration values of ammonia in the sample;
  (c) comparing the one or more concentration values of ammonia in the sample to a threshold value of ammonia concentration identified as being in a healthy range; and
  (d) identifying the subject as having a metabolic disease if the one or more concentration values of ammonia in the sample exceed or fall below the threshold value;
  (e) administering a therapeutically effective amount of a therapeutic agent to treat the metabolic disease.

21. The method of claim 20, wherein the metabolic disease is hyperammonemia.

22. A biosensor comprising:
  at least a first and second vessel configured for receiving a sample from a point exterior to the biosensor;
  a fluid exchange opening positioned between the first and the second vessel;
  a membrane positioned across or over the fluid exchange opening; and
  a catalyst in liquid phase or solid phase a hypohalite in liquid phase;
  an alkali buffer in liquid phase;
  a phenolic reagent in liquid phase or solid phase; and
  a fluid circuit comprising, in fluid communication:
    the first and second vessel; a reagent conduit; and a detection vessel positioned distal from the first and second vessel;
  wherein the catalyst is sodium nitroprusside or a salt thereof, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than 8.4 µM.

23. The biosensor of claim 22, wherein the catalyst is sodium nitroprusside in liquid phase at a concentration from about 1.0 mM to about 2.0 mM.

24. The biosensor of claim 22 comprising:
  a first operable condition, in which the first vessel comprises a sample;
  a second operable condition, in which the first vessel comprises a sample and an aqueous buffer;
  a third operable condition, in which the reagent conduit comprises a mixture of the aqueous buffer, the alkali buffer, the hypohalite, the catalyst and the phenolic reagent and the mixture moves toward the detection vessel and the catalyst mixes with the sample for a time period sufficient for the catalyst to catalyze an indophenol reaction; and
  a fourth operable condition, in which the detection vessel comprises the mixture and a light source positioned proximate to the detection vessel capable of emitting light through the detection vessel sufficient to quantify the amount of ammonia in the sample; wherein, in the fourth operable condition, the light source is a photodiode capable of emitting light in the detection vessel and producing an amount of light sufficient to enable absorbance readings detected at a wavelength of light from about 600 to about 650 nm.

25. The biosensor of claim 22, wherein, if the sodium nitroprusside or salt thereof is in liquid phase, the sodium nitroprusside or salt thereof is at a concentration greater than 16.6 µM.

26. The biosensor of claim 22, wherein, if the sodium nitroprusside or salt thereof is in liquid phase, the sodium nitroprusside or salt thereof is at a concentration from 665 to 1996 µM.

27. A kit comprising a solid support that comprises:
  at least a first and second vessel;
  a fluid exchange opening positioned between the first and the second vessel;
  at least a first conduit in fluid communication with at least the first vessel, the first conduit configured to receive a fluid from a point external to the biosensor; and
  a membrane positioned at the fluid exchange opening;
  a catalyst in liquid phase or solid phase;
  a hypohalite in liquid phase;
  an alkali buffer in liquid phase;
  a phenolic reagent in liquid phase or solid phase; and
  a fluid circuit comprising, in fluid communication:
    the first and second vessel; a reagent conduit; and a detection vessel positioned distal from the first and second vessel;
  wherein the catalyst is sodium nitroprusside, and, if the catalyst is in solid phase, the biosensor comprises from about 5.8 to about 7.3 micrograms of sodium nitroprusside or a salt thereof in solid phase; and, if the catalyst is in liquid phase, the sodium nitroprusside or a salt thereof is at a concentration greater than 8.4 µM; and
  wherein the membrane comprises an ionomer.

28. A method of quantifying a concentration of ammonia or ammonium ion in a sample of bodily fluid comprising contacting the sample to the biosensor of claim 1.

29. The method of claim 28, wherein the step of contacting comprises exposing the sample to the biosensor of claim 1 for a period of time sufficient to allow modification of an indophenol reagent or indophenol related compound to an indophenol or indophenol reaction product.

30. The method of claim 28, wherein the method does not comprise exposing the sample of bodily fluid to any external stimuli or reagent prior to contacting the sample to the biosensor.

31. The method of claim 28, wherein the sample of bodily fluid is whole blood from a subject.

* * * * *